(12) United States Patent
Harran et al.

(10) Patent No.: US 7,816,538 B2
(45) Date of Patent: *Oct. 19, 2010

(54) DIMERIC SMALL MOLECULE POTENTIATORS OF APOPTOSIS

(75) Inventors: Patrick G. Harran, Dallas, TX (US); Xiaodong Wang, Dallas, TX (US); Jef K. De Brabander, Dallas, TX (US); Lin Li, Dallas, TX (US); Ranny Mathew Thomas, Waltham, MA (US); Hidetaka Suzuki, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 12 days.

This patent is subject to a terminal disclaimer.

(21) Appl. No.: 12/509,190

(22) Filed: Jul. 24, 2009

(65) Prior Publication Data

US 2009/0312379 A1    Dec. 17, 2009

Related U.S. Application Data

(63) Continuation of application No. 11/958,365, filed on Dec. 17, 2007, which is a continuation of application No. 11/070,733, filed on Mar. 1, 2004, now Pat. No. 7,309,792.

(60) Provisional application No. 60/549,520, filed on Mar. 1, 2004.

(51) Int. Cl.
  C07D 249/04   (2006.01)
  C07D 257/04   (2006.01)
  A61K 31/41    (2006.01)
  A61K 31/42    (2006.01)

(52) U.S. Cl. ........................ 548/237; 548/251; 548/252; 548/253; 548/255; 564/153; 514/359; 514/374; 514/381; 514/616

(58) Field of Classification Search ................. 514/359, 514/374, 381, 616; 548/237, 251, 252, 253, 548/255; 564/153
See application file for complete search history.

(56) References Cited

U.S. PATENT DOCUMENTS 7,309,792 B2 * 12/2007 Harran et al. ................ 548/237

FOREIGN PATENT DOCUMENTS

WO     WO 98/12213     *  3/1998

OTHER PUBLICATIONS

Bockbrader et al, Oncogene, 2005, 7381-7388.*

* cited by examiner

*Primary Examiner*—Shailendra Kumar
(74) *Attorney, Agent, or Firm*—Richard Aron Osman

(57) ABSTRACT

Caspase activity and apoptosis are promoted using active, dimeric Smac peptide mimetics of the general formula M1-L-M2, wherein moieties M1 and M2 are monomeric Smac mimetics and L is a covalent linker. Target cancerous or inflammatory cells are contacted with an effective amount of an active, dimeric Smac mimetic, and a resultant increase in apoptosis of the target cells is detected. The contacting step may be effected by administering to a pharmaceutical composition comprising a therapeutically effective amount of The compoundic mimetic, wherein the individual may be subject to concurrent or antecedent radiation or chemotherapy for treatment of a neoproliferative pathology.

112 Claims, No Drawings

DIMERIC SMALL MOLECULE POTENTIATORS OF APOPTOSIS

This application is a continuation of Ser. No. 11/958,365 filed Dec. 17, 2007, which is a continuation of U.S. Ser. No. 11/070,733, filed Mar. 1, 2005 (U.S. Pat. No. 7,309,792), which is a continuation of U.S. Ser. No. 60/549,520 filed Mar. 1, 2004.

This work was supported by National Institute of Health Grant No. P01 CA9547101. The U.S. government has certain rights in this invention.

INTRODUCTION

1. Field of the Invention

The field of the invention is dimeric small molecule potentiators of apoptosis

2. Background of the Invention

Apoptosis plays a central role in the development and homeostasis of all multi-cellular organisms. Abnormal inhibition of apoptosis is a hallmark of cancer and autoimmune diseases, whereas excessive activation of cell death is implicated in neuro-degenerative disorders such as Alzheimer's disease. Pro-apoptotic chemotherapeutic drugs provide a recent approach to overcoming the clinical problem of drug resistance; see, e.g. Makin et al., Cell Tissue Res 2000 July; 301(1):143-52 ("Apoptosis and cancer chemotherapy").

The mechanism of apoptosis is conserved across species and executed with a cascade of sequential activation of proteases called caspases. Once activated, these caspases are responsible for proteolytic cleavage of a broad spectrum of cellular targets that ultimately lead to cell death. IAPs (inhibitor-of-apoptosis proteins) regulate apoptosis by inhibiting caspases; and a protein called Smac (second mitochondria-derived activator of caspases) binds to and inhibits IAPs, and thereby promotes caspase activation. N-terminal Smac-derived peptides and mimetics have been shown to similarly inhibit IAPs, and promote caspase activation. IAPs are components of TNFR (tumor necrosis factor receptor), so IAP inhibitors can divert TNFR signalling from an NfkB-mediated pro-inflammatory signal, to an anti-inflammatory apoptotic signal.

RELEVANT LITERATURE

Liu et al, Structural basis for binding of Smac/DIABLO to the XIAP BIR3 domain; Nature 2000 Dec. 21-28; 408(6815): 1004-8.

Wu et al., Structural basis of IAP recognition by Smac/DIABLO; Nature 2000 Dec. 21-28; 408(6815): 1008-12.

Fesik, et al., Peptides derived from smac (DIABLO) and methods of using them to screen for apoptosis modulating compounds; WO 2002030959.

McLendon, et al., IAP binding peptides and assays for identifying compounds that bind IAP; WO 2002096930.

Shi, Compositions and methods for regulating apoptosis; WO 2002026775.

Debatin, et al., Smac-peptides as therapeutics against cancer and autoimmune diseases by sensitizing for TRAIL- or anticancer drug-induced apoptosis; WO 2003086470.

Alnemri, Conserved sequence of XIAP-binding motif in human caspase-9 and Smac/DIABLO and therapeutic uses for screening modulators of apoptosis; WO 2003010184.

Arnt et al., Synthetic Smac/DIABLO peptides enhance the effects of chemotherapeutic agents by binding XIAP and cIAP1 in situ; J Biol Chem. 2002 Nov. 15; 277(46):44236-43. Epub 2002 Sep. 5.

IAP binding peptide or polypeptide and methods of using the same; US Pat Publ No. 20020132786.

US Pat Publ No. 20020160975, Conserved XIAP-interaction motif in caspase-9 and Smac/DIABLO for mediating apoptosis.

US Pat Publ No. 20020177557, Compositions and method for regulating apoptosis.

U.S. Pat. No. 6,608,026, Wang, et al., Apoptotic Compounds;

Li et al., Targeting and amplification of immune killing of tumor cells by pro-Smac, Int J Cancer. 2004 Mar. 10; 109(1):85-94.

SUMMARY OF THE INVENTION

We have serendipitously discovered that dimeric versions of pro-apoptotic Smac peptides and peptide mimetics provide vastly improved reagents over the prior art monomers. These dimers similarly bind cytosolic IAPs and relieve their inhibition of caspases; however, they do so with exceptional potency. We believe they bind to adjacent repeats of the BIR (baculoviral inhibitory repeat) domain within IAP proteins, and that this bipartite recognition is crucial to their effectiveness: the corresponding monomers typically have much less activity in cell extracts (e.g. ~10000 times less active). In fact, our data indicate that dimers function catalytically, shunting uncomplexed IAP to the ubiquitin/proteasome degradation pathway. The dimers synergize with TRAIL (TNF-related apoptosis inducing ligand) to induce apoptosis in glioblastoma cell culture, typically at picomolar concentrations. The compounds provide new adjuvant chemotherapeutics for cancers, particularly those that resist programmed cell death by over-expressing IAP proteins.

As a preferred embodiment, we developed novel series of dimeric molecules that also mimic the endogenous function of Smac, and provide vastly enhanced activity over prior Smac mimetics. The compounds are stable, protease resistant, and freely membrane permeant; by themselves, the molecules are not cytotoxic. No similar compounds have been described. Though others have attempted to use Smac-derived peptides and peptide-carrier constructs for similar purposes, these prior art materials are severely limited by their physicochemical properties and their potency is orders of magnitude less than that disclosed here.

Accordingly, the invention provides methods and compositions for enhancing apoptosis of pathogenic cells using pro-apoptotic dimeric Smac peptide mimetics. The general method comprises the step of contacting the cells with an effective amount of an active, dimeric Smac mimetic, typically followed by the step detecting, directly, indirectly or inferentially a resultant increase in apoptosis of the target cells. Dimer activity may be determined by IAP binding, procaspase-3 activation or promotion of apoptosis, etc.

In preferred embodiments, the cells are in situ in an individual and the contacting step is effected by administering to the individual a pharmaceutical composition comprising a therapeutically effective amount of the mimetic, wherein the individual may be subject to concurrent or antecedent radiation or chemotherapy for treatment of a neoproliferative pathology. In particular embodiments, the pathogenic cells are of a tumor, such as a tumor selected from the group consisting of glioblastoma, astrocytoma, breast cancer, prostate cancer, lung cancer, pancreatic cancer, gastric cancer, colon cancer, ovarian cancer, renal cancer, hepatoma, melanoma, lymphoma, and sarcoma. In additional embodiments, the target cells are pro-inflammatory cells or cells of tissue subject to pathogenic inflammation and/or autoimmunity. A wide variety of diseased provide target pathogenic inflammation, including rheumatoid arthritis, diabetes, asthma, lupus, inflammatory bowel disease (Crohn's disease and related conditions), multiple sclerosis, chronic obstructive pulmonary disease, inflammatory bowel and pelvic diseases, allergic rhinitis (hay fever), cardiovascular disease, etc.

The subject compositions encompass pharmaceutical compositions comprising a therapeutically effective amount of an active, dimeric Smac mimetic in dosage form and a pharmaceutically acceptable carrier. In some embodiments, such compositions further comprise an additional therapeutic agent, such as an anti-neoproliferative chemotherapeutic agent, other than the mimetic.

The invention also provides methods for making and screening for active dimeric Smac peptide mimetics. For example, one general assay comprises the steps of generating a dimeric Smac peptide mimetic from a monomeric mimetic, and detecting enhanced activity of the resultant dimer over the monomeric precursor, e.g. as determined by IAP binding, procaspase-3 activation or promotion of apoptosis.

The subject mimetics encompass a wide variety of active, dimeric Smac mimetics of the general formula M1-L-M2, wherein moieties M1 and M2 are monomeric Smac mimetics and L is a linker covalently linking M1 and M2 in the active dimer. M1 and M2 each encompass monomeric Smac mimetics, particularly pro-apoptotic, particularly AVP-type and AV peptoid mimetics; see e.g. WO 2002030959; WO 2002096930; WO 2002026775; WO 2003086470; WO 2003010184; US Pat Publ Nos. 20020177557, 20020132786, 20020160975; U.S. Pat. No. 6,608,026; etc, and include the varied and diverse monomeric mimetic structures disclosed or referenced herein.

The linker L serves to covalently couple M1 and M2 in a dimeric structure that provides enhanced pro-apoptotic activity over the uncoupled monomers, and is otherwise compatible with the disclosed uses of the dimers (e.g. physiological compatibility and stability). A wide variety of linkers may be used, and particular linkers are readily assayed empirically. Generally, L is a contiguous chain of between 2 and 200 atoms, preferably between 4 and 100 atoms, more preferably between 4 and 25 atoms, and a MW between 20 and 2 K D, preferably between 40 and 1 K D, more preferably between 56 and 1 K D. L maybe bisymmmetrical, or nonsymmetrical, and may link different, isometric or identical M1 and M2, typically has spans between about 3 and 3 K A, preferably between about 6 and 2000, more preferably between about 12 and 1000 A, etc. Exemplary, nonlimiting suitable linkers are further described below.

In a particular embodiment, the invention provides a dimeric compound of formula II, formula II

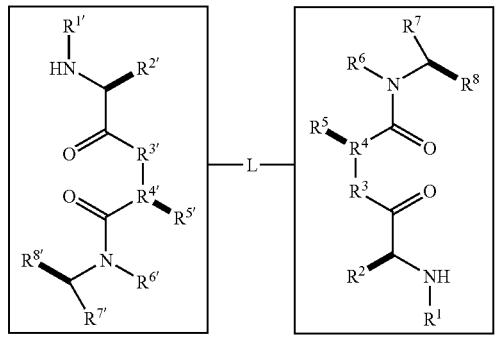

wherein:

R1 and R1' are selected from hydrogen, optionally substituted methyl, and hydroxyl;

R2 and R2' are selected from optionally substituted methyl and optionally substituted ethyl;

R3 and R3' are selected from CH2, NH, O and S;

R4 and R4' are selected from CH and N;

R5-R8, and R5'-R8' are selected from hydrogen, optionally hetero-, optionally substituted alkyl, optionally hetero-, optionally substituted alkenyl, optionally hetero-, optionally substituted alkynyl, optionally hetero-, optionally substituted aryl; and L is a linker covalently linking R2, R5, R6 or R7, with R2', R5', R6' or R7', or a pharmaceutically-acceptable salt thereof.

Various particular embodiments include all combinations wherein:

R1 and R1' are selected from hydrogen and methyl;

R2 and R2' are selected from methyl and ethyl;

R3 and R3' are NH;

R4 and R4' are CH;

R5 and R5' are C1-C3 alkyl; and

R6/R6' and R7/R7', or R7/R7' and R8/R8' are connected in a 5- to 8-membered ring; more particularly wherein R1 and R1' are selected from hydrogen and methyl, R2 and R2' are selected from methyl and ethyl, R3 and R3' are NH, R4 is CH, and R5 and R5' are C1-C3 alkyl, and L covalently links R5, R6 or R7, with R5', R6' or R7', More particular embodiments include all combinations wherein:

R1/R1' and R2/R2' are connected to form a 4-membered ring (azetidine);

R7 and R8 are connected in a 5- or 6-membered ring;

R6 and R7 are connected in a 5- or 6-membered ring, particularly wherein R6 and R7 are connected in a 5-membered ring, and L covalently links the ring with R2', R5', R6' or R7'; and R8 comprises a 5- or 6-membered ring, particularly wherein R8 comprises a 5-membered ring, comprising at least one heteroatom, at least one substitution, and at least one unsaturation.

In particular embodiments, the L is a contiguous chain of between 4 and 100 atoms, and between 40 and 1 kD, and is an optionally hetero-, optionally substituted dialkynyl radical. In particular embodiments, the linker is bisymmetrical about the linker; in particular embodiments, the dimer itself is bisymmetrical.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat a disease associated with undesirably high IAP activity, and/or undesirably low caspase or apoptotic activity, particularly as found in many tumors and inflammation.

Accordingly, the invention provides methods of treating a disease associated with undesirable caspase activity, the method comprising the step of administering an effective dosage of the subject compounds and compositions, which may be followed by the step of detecting a resultant decrease in pathology associated with the disease, and which may be prefaced by the step of diagnosis such disease and/or prescribing such composition. Applicable disease include tumors and inflammation.

The invention also provides methods of inhibiting a caspase, the method comprising the step of contacting a composition comprising a caspase with an effective amount of the subject compounds and compositions, which may be followed by the step of detecting a resultant change in caspase activity.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

As used herein, the term "heteroatom" is meant to include oxygen (O), nitrogen (N), sulfur (S) and silicon (Si).

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH2-CH2-CH2-CH2-. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)2-CH3, —CH=CH—O—CH3, —Si(CH3)3, —CH2-CH=N—OCH3, and —CH=CH—N(CH3)-CH3. Up to two heteroatoms may be consecutive, such as, for example, —CH2-NH—OCH3 and —CH2-O—Si(CH3)3.

Similarly, the term "heteroalkylene," by itself or as part of another substituent means a divalent radical derived from heteroalkyl, as exemplified by —CH2-CH2-S—CH2-CH2- and —CH2-S—CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R''', —OC(O)R', —C(O)R', —CO2R', —CONR'R", —OC(O)NR'R", —NR"C(O)R', —NR'—C(O)NR"R''', —NR'—SO2NR''', —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, in a number ranging from zero to three, with those groups having zero, one or two substituents being particularly preferred. R', R" and R''' each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF3 and —CH2CF3).

Preferred substituents for the alkyl and heteroalkyl radicals are selected from: —OR', =O, —NR'R", —SR', halogen, —SiR'R"R''', —OC(O)R', —C(O)R', —CO2R', —CONR'R", —OC(O)NR'R", —NR"C(O)R', —NR"CO2R', —NR'—SO2NR"R''', —S(O)R', —SO2R', —SO2NR'R", —NR"SO2R, —CN and —NO2, where R' and R" are as defined above. Further preferred substituents are selected from: —OR', =O, —NR'R", halogen, —OC(O)R', —CO2R', —CONR'R", —OC(O)NR'R", —NR"C(O)R', —NR"CO2R', —NR'—SO2NR"R''', —SO2R', —SO2NR'R", —NR"SO2R, —CN and —NO2.

Similarly, substituents for the aryl and heteroaryl groups are varied and selected from: halogen, —OR', —OC(O)R', —NR'R", —SR', —R', —CN, —NO2, —CO2R', —CONR'R", —C(O)R', —OC(O)NR'R", —NR"C(O)R', —NR"CO2R', —NR'—C(O)NR"R''', —NR'—SO2NR"R''', —NH—C(NH2)=NH, —NR'C(NH2)=NH, —NH—C(NH2)=NR', —S(O)R', —SO2R', —SO2NR'R", —NR"SO2R, —N3, —CH(Ph)2, perfluoro(C1-C4)alkoxy and perfluoro(C1-C4)alkyl, in a number ranging from zero to the total number of open valences on the aromatic ring system; and where R', R" and R''' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the present invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO2, —CO2R', —CONR'R", —C(O)R', —OC(O)NR'R", —NR"C(O)R', —S(O)R', —SO2R', —SO2NR'R", —NR"SO2R, —N3, —CH(Ph)2, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO2, —CO2R', —CONR'R", —NR"C(O)R', —SO2R', —SO2NR'R", —NR"SO2R, perfluoro(C1-C4)alkoxy and perfluoro(C1-C4)alkyl.

The substituent —CO2H, as used herein, includes bioisosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH2)q-U—, wherein T and U are independently —NH—, —O—, —CH2- or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH2-, —O—, —NH—, —S—, —S(O)—, —S(O)2-, —S(O)2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t-, where s and t are independently integers of from 0 to 3, and X is —O—, —NR'—, —S—, —S(O)—, —S(O)2-, or —S(O)2NR'—. The substituent R' in —NR'— and —S(O)2NR'— is selected from hydrogen or unsubstituted (C1-C6)alkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) J. Pharm. Sci. 66: 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 (125I) or carbon-14 (14C). All isotopic variations of the compounds of the present invention, whether radioactive or not, are intended to be encompassed within the scope of the present invention.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

In a particular embodiment, the invention provides a dimeric compound M1-L-M2, wherein M1 and M2 are independently a moiety of formula I, and covalently bound through the molecular linker L through R2, R5, R6 or R7:

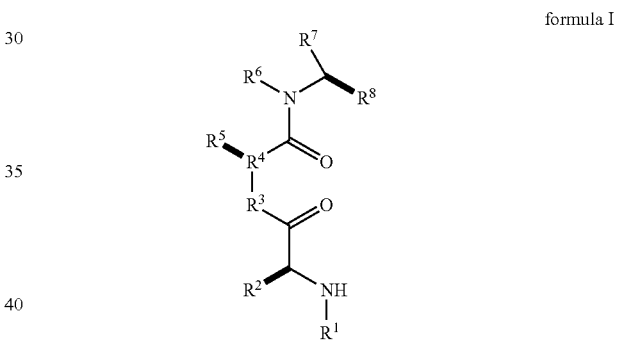

formula I

This particular embodiment may also be characterized as a dimeric compound of formula II,

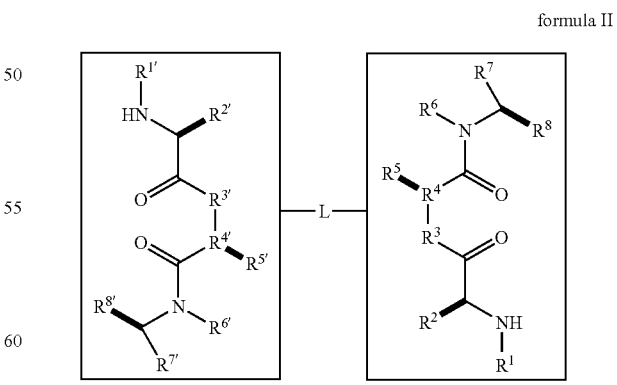

formula II including all combinations wherein:

R1 and R1' are selected from hydrogen, optionally substituted methyl, and hydroxyl;

R2 and R2' are selected from optionally substituted methyl and optionally substituted ethyl;

R3 and R3' are selected from CH2, NH, O and S;

R4 and R4' are selected from CH and N;

R5-R8, and R5'-R8' are selected from hydrogen, optionally hetero-, optionally substituted alkyl, optionally hetero-, optionally substituted alkenyl, optionally hetero-, optionally substituted alkynyl, optionally hetero-, optionally substituted aryl; and L is a linker covalently linking R2, R5, R6 or R7, with R2', R5', R6' or R7', or a pharmaceutically-acceptable salt thereof.

One or more corresponding R and R' groups may be the same or different. Various particular embodiments include all combinations wherein:

R1 and R1' are selected from hydrogen and methyl;

R2 and R2' are selected from ethyl, and preferably methyl;

R3 and R3' are selected from CH2, O, and preferably NH;

R4 and R4' are CH;

R5 and R5' are C1-C3 alkyl; and

R6/R6' and R7/R7', or R7/R7' and R8/R8' are connected in a 5- to 8-membered ring.

In more particular embodiments, R1 and R1' are selected from hydrogen and methyl, R2 and R2' are selected from methyl and ethyl, R3 and R3' are NH, R4 is CH, and R5 and R5' are C1-C3 alkyl, and L covalently links R5, R6 or R7, with R5', R6' or R7'.

Particular embodiments include all combinations wherein:

R1/R1' and R2/R2' are connected to form a 4-membered ring (azetidine);

R7 and R8 are connected in a 5- or 6-membered ring;

R6 and R7 are connected in a 5- or 6-membered ring, particularly wherein R6 and R7 are connected in a 5-membered ring, and L covalently links the ring with R2', R5', R6' or R7'; and R8 comprises a 5- or 6-membered ring, particularly wherein R8 comprises a 5-membered ring, comprising at least one heteroatom, at least one substitution, and at least one unsaturation.

In particular embodiments, the L is a contiguous chain of between 4 and 100 atoms, and between 40 and 1 kD, and is an optionally hetero-, optionally substituted dialkynyl radical. In particular embodiments, the linker is bisymmetrical; and in more particular embodiments, the dimer itself is symmetrical, i.e. the linker is bisymmetrical, and M1 and M2 are isomers (the corresponding R and R' groups are the same).

In a particular embodiment, the L is substituted with or is a contiguous chain incorporating an aminated moiety, particularly an amino acid such as lysine or arginine or its biostere, wherein the amine can be protonated or alykylated to create a positive charge, and to make the compound a triamine with three potential points of contact with a BIR domain (see, e.g. Exemplary Dimers.

These and other embodiments of the invention are found and/or exemplified in the sections entitled Exemplary Dimers, Exemplary Monomers, and Experimental Procedures.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat a disease associated with undesirably high IAP activity, and/or undesirably low caspase or apoptotic activity, particularly as found in many tumors and inflammation.

Accordingly, the invention provides methods of treating a disease associated with undesirable caspase activity, the method comprising the step of administering an effective dosage of the subject compounds and compositions, which may be followed by the step of detecting a resultant decrease in pathology associated with the disease, and which may be prefaced by the step of diagnosis such disease and/or prescribing such composition. Applicable disease include tumors and inflammation.

The invention also provides methods of inhibiting a caspase, the method comprising the step of contacting a composition comprising a caspase with an effective amount of the subject compounds and compositions, which may be followed by the step of detecting a resultant change in caspase activity.

The exemplified mimetics are nonlimiting. Peptide mimetic chemistry is a well-established art wherein skilled practitioners can readily generate a wide variety of mimics using conventional chemistry (see, e.g. Liao et al. (1998) J. Med. Chem 41, 4767-4776; Andrade-Gordon et al. (1999) PNAS USA 96, 12257-12262; Boatman et al. (1999) J. Med. Chem. 42, 1367-1375; Kasher et al. (1999) J. Mol. Biol 292, 421-429; U.S. Pat. No. 5,981,467; etc.) and these other strategies are applicable here, so long as the resultant mimetics are screened for and demonstrated to provide the requisite activity as described herein.

Synthetic methods for producing mimetics are well-known in the art. Some general means for the production of peptides, analogs or derivatives are outlined in *Chemistry and Biochemistry of Amino Acids, Peptides and Proteins, A Survey of Recent Developments*, Weinstein, B. ed., Marcell Dekker, Inc., publ. New York (1983). A wide variety of well-established techniques are available for synthesizing peptide mimetics, see, e.g. submonomer method of R. Zuckermann et al., J. Am. Chem. Soc. (1992) 0114:10646-7. Synthesis by solid phase techniques of heterocyclic organic compounds in which N-substituted glycine monomer units forms a backbone is described in U.S. Pat. No. 5,958,792, wherein combinatorial libraries of mixtures of such heterocyclic organic compounds can then be assayed for the ability to inhibit IAP as described below. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization, also as described in U.S. Pat. No. 5,958,792. General preparative protocols for exemplary mimetic classes are as follows:

Preparation of α-Polyesters Using Chiral α-Hydroxy Acids As Building Blocks. The α-polyester structures can be prepared by using chemical synthesis technology known to those skilled in the art. For details of the reaction, see Brewster, P., et al., Nature, (1990) 166:179. An alternative method for producing similar structures is disclosed in Chan, P. C., and Chong, J. M., Tetrahedron Lett. (1990) 1985. Further, various publications cited within the Chan et al. publication describe techniques for synthesizing chiral α-hydroxy acids.

Preparation of Polythioamides Using Chiral .alpha.-Amino Acids As Building Blocks. Polythioamide structures can be synthesized using techniques such as those described in Clausen, K., et al., J. Chem. Soc. Perkin Trans. I (1984) 785, and Tetrahedron Lett. (1990) 31:23

Preparation of Polyhydroxymates Using Chiral .alpha.-Amino Acids As Building Blocks. Polyhydroxymates can be synthesized using techniques as disclosed in Kolasa, T., and Chimiak, A., Tetrahedron (1977) 33:3285. References cited within Kolasa disclose and describe chemical techniques for synthesizing N-hydroxy amino acids which can be used in mimetic synthesis.

Preparation of β-Polyesters Using Chiral β-Hydroxy Acids As Building Blocks. β-polyesters can be synthesized using a synthesis protocol as described in Elliott, J. D., et al., Tetrahedron Lett. (1985) 26:2535, and Tetrahedron Lett. (1974) 15:1333.

Preparation of Polysulfonamides Using Chiral β-Amino Sulfonic Acids As Building Blocks. Polysulfonamides can be synthesized using the reaction scheme shown in U.S. Pat. No. 6,075,121. The chiral β-amino acids have been described within Kokotos, G., Synthesis (1990) 299.

Preparation of N-Alkylated Polysulfonamides Using Achiral β-Amino Sulfonic Acids As Building Blocks. Similarly, these polysulfonamides can be synthesized using the reaction scheme shown in U.S. Pat. No. 6,075,121.

Preparation of Polyureas Using Achiral β-Amino Acids As Building Blocks. Polyureas can be synthesized using techniques such as those described in Shiori, T., et al., J. Am. Chem. Soc. (1972) 94:6302, and Scholtz, J., and Bartlett, P., Synthesis (1989) 542.

Preparation of Polyurethanes Using Achiral β-Amino Alcohols As Building Blocks. Polyurethanes can be synthesized using the reaction scheme shown in U.S. Pat. No. 6,075, 121. Individual N-substituted glycine analogs are known in the art, and may be prepared by known methods. See, for example, Sempuku et al., JP 58/150,562 (Chem Abs (1984) 100:68019b); Richard et al., U.S. Pat. No. 4,684,483; and Pulwer et al., EPO 187,130.

Several N-substituted glycine derivatives are available from commercial sources. For example, N-benzylglycine is available from Aldrich Chemical Co. (Milwaukee, Wis.) as the ethyl ester. The ester is hydrolyzed in KOH/MeOH, then protonated in HCl to yield N-benzylglycine. This may then be protected with Fmoc (fluorenylmethoxycarbonyl) by treatment with Fmoc-Cl in aqueous dioxane at high pH (about 10).

Other N-substituted glycine analogs are synthesized by simple chemical procedures. N-isobutylglycine may be prepared by reacting excess 2-methylpropylamine with a haloacetic acid.

N-(2-aminoethyl)glycine may be prepared by reacting excess 1,2-diaminoethane with a haloacetic acid and purifying on Dowex-1® (OH form), eluting with acetic acid. The unprotected amine is protected with t-butoxycarbonyl (t-Boc) using conventional techniques at pH 11.2, followed by protection of the secondary amine with Fmoc.

N-(2-hydroxyethyl)glycine may be prepared by reacting excess 2-aminoethanol with haloacetic acid and purifying on Dowex-1® (OH form), eluting with acetic acid. The amine nitrogen is then protected with Fmoc. Next, the acid group is esterified with methanol under acidic conditions. The methyl ester is then treated with isobutylene to form the t-butyl ether. Then, the methyl ester is hydrolyzed using porcine liver esterase in phosphate buffer at pH 8.0, to provide a protected N-substituted glycine analog in a form suitable for mimetic synthesis. As an alternative to the above, the Fmoc-hydroxyethylglycine is treated with t-butyldiphenylsilylchloride in DMF and imidazole to give a silyl-protected alcohol.

N-(carboxymethyl)glycine may be prepared by reacting glycine t-butyl ester with 2-haloacetate in aqueous solution. The product may be protected directly by addition of Fmoc. As an alternative, the N-(carboxymethyl)glycine may be prepared by mixing glycine t-butyl ester, glyoxylic acid and palladium on charcoal under an atmosphere of hydrogen in water at pH 6. The compound is then treated with FMOC in the usual manner.

Once the monomers have been synthesized, they may be coupled with other monomers and/or conventional amino acids to form analogs using standard peptide chemistry. For example, an Fmoc-protected monomer (N-substituted glycine or conventional amino acid) may be immobilized on a suitable resin (e.g., HMP) by reaction with benzotriazol-1-yloxy-tris(dimethylamino)phosphonium hexafluorophosphate (BOP) or a carbodiimide (for example, dicyclohexylcarbodiimide) under basic conditions (e.g., pH 9) in a suitable solvent. The Fmoc protecting group is removed by treatment with piperidine. Each additional monomer is then attached sequentially using BOP or a carbodiimide, until the entire sequence has been constructed. The completed chain is then detached from the resin and the sidechain deprotected by treating with trifluoroacetic acid (TFA).

Alternatively, one may connect N-substituted glycine analogs to the ends of mimetics produced by other methods, for example, by recombinant expression or isolation from natural sources. Further, N-substituted glycine analogs may be inserted within the sequence of such mimetics by cleaving the mimetic at the desired position, attaching an N-substituted glycine analog, and reattaching the remainder of the molecule or a chemically-synthesized replacement.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the mimetics may be advantageously used in conjunction with other chemotherapuetic agents such as diethylstilbestrol or DES, 5-fluorouracil, methotrexate, interferon-alpha, aspariginase, tamoxifen, flutamide, etc, and chemotherapeutic agents described in the *Merck Manuel*, 16th edition 1992, Merck Research Laboratories, Rahway, N.J.; *Goodman & Gilman's The Pharmacological Basis of Therapeutics*, $9^{th}$ Ed., 1996, McGraw-Hill, esp. Chabner et al., *Antineoplastic Agents*, etc. or otherwise known in the art. Hence the compositions may be administered separately, jointly, or combined in a single dosage unit. In a particular embodiment, the combination therapy is effected by a conjugate of the mimetic bound covalently to the anti-neoproliferative chemotherapeutic or other pharmaceutically active agent. Any suitable conjugation chemistry may be used.

The amount administered depends on the mimetic formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 0.1 mg to 1000 mg, preferably from about 1 mg to 300 mg, more preferably 10 mg to 200 mg, according to the particular application. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The following are examples (Formulations 1-4) of mimetic capsule formulations.

TABLE 1

Capsule Formulations

| | Capsule Formulation | | | |
|---|---|---|---|---|
| | Formula 1 mg/capsule | Formula 2 mg/capsule | Formula 3 mg/capsule | Formula 4 mg/capsule |
| Mimetic (Solid Solution) | 100 | 400 | 400 | 200 |
| Silicon Dioxide | 0.625 | 2.5 | 3.75 | 1.875 |
| Magnesium Stearate NF2 | 0.125 | 0.5 | 0.125 | 0.625 |
| Croscarmellose Sodium NF | 11.000 | 44.0 | 40.0 | 20.0 |
| Pluronic F68 NF | 6.250 | 25.0 | 50.0 | 25.0 |
| Silicon Dioxide NF | 0.625 | 2.5 | 3.75 | 1.875 |
| Magnesium Stearate NF | 0.125 | 0.5 | 1.25 | 0.625 |
| Total | 118.750 | 475.00 | 475.00 | 475.00 |
| Capsule Size | No. 4 | No. 0 | No. 0 | No. 2 |

Preparation of Solid Solution

Crystalline mimetic (80 g/batch) and the povidone (NF K29/32 at 160 g/batch) are dissolved in methylene chloride (5000 mL). The solution is dried using a suitable solvent spray dryer and the residue reduced to fine particles by grinding. The powder is then passed through a 30 mesh screen and confirmed to be amorphous by x-ray analysis.

The solid solution, silicon dioxide and magnesium stearate are mixed in a suitable mixer for 10 minutes. The mixture is compacted using a suitable roller compactor and milled using a suitable mill fitted with 30 mesh screen. Croscarmellose sodium, Pluronic F68 and silicon dioxide are added to the milled mixture and mixed further for 10 minutes. A premix is made with magnesium stearate and equal portions of the mixture. The premix is added to the remainder of the mixture, mixed for 5 minutes and the mixture encapsulated in hard shell gelatin capsule shells.

The mimetics can be administered by a variety of methods including, but not limited to, parenteral, topical, oral, or local administration, such as by aerosol or transdermally, for prophylactic and/or therapeutic treatment. The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

The particular choice of mimetic, chemotherapeutic agent and/or radiation depends upon the diagnosis of the attending physicians and their judgement of the condition of the patient and the appropriate treatment protocol. The mimetic, chemotherapeutic agent and/or radiation may be administered concurrently (e.g., simultaneously, essentially simultaneously or within the same treatment protocol) or sequentially, in any order, depending upon the nature of the proliferative disease, the condition of the patient, and the actual choice of chemotherapeutic agent and/or radiation to be administered in conjunction (i.e., within a single treatment protocol) with the mimetic. Similarly, the mimetic and the chemotherapeutic agent do not have to be administered in the same pharmaceutical composition, and may, because of different physical and chemical characteristics, be administered by different routes.

In one embodiment of the present invention, the method of the invention includes systemic or local administration of a mimetic. Where systemic administration is desired, the mimetic may be administered, for example, by intravenous injection or orally. One embodiment of the invention provides local administration of the mimetic, for example, at the tumor site. With local administration of the mimetic, the preferred mode of administration is by local injection. However, local administration may also be by catheter, or by local deposition, for example by intra- or peritumoral administration of products sold under the trademark Depofoam®, slow release pump/drug delivery service, implantable or topical gel or polymer, depending on the nature and location of the tumor. Administration of the therapeutics of the invention can also be effected by gene therapy protocol.

The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, disorder or biological condition being treated. Depending on the therapeutic, the dosage and protocol for administration will vary, and the dosage will also depend on the method of administration selected, for example, local or systemic administration. For a very potent mimetic, microgram (ug) amounts per kilogram of patient may be sufficient, for example, in the range of about 1 ug/kg to about 500 mg/kg of patient weight, and about 100 ug/kg to about 5 mg/kg, and about 1 ug/kg to about 50 ug/kg, and, for example, about 10 ug/kg.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as mimetic potency, severity of the disease being treated. For example, a dosage regimen of the mimetics can be oral administration of from 10 mg to 2000 mg/day, preferably 10 to 1000 mg/day, more preferably 50 to 600 mg/day, in two to four (preferably two) divided doses, to reduce tumor growth. In cases where the mimetic is based on a fused-ring cyclic benzocycloheptapyridine, the preferred dosage of the inhibitor is oral administration of from 50 to 600 mg/day, more preferably 50 to 400 mg/day, in two divided doses. Intermittent therapy (e.g., one week out of three weeks or three out of four weeks) may also be used.

In one example of combination therapy in the treatment of pancreatic cancer, the mimetic is administered orally in a range of from 50 to 400 mg/day, in two divided doses, on a continuous dosing regimen; and the antineoplastic agent is gemcitabine administered at a dosage of from 750 to 1350 mg/m$^2$ weekly for three out of four weeks during the course of treatment. In another example of combination therapy in the treatment of lung cancer, the mimetic is administered orally in a range of from 50 to 400 mg/day, in two divided doses, on a continuous dosing regimen; and the antineoplastic agent is paclitaxel administered at a dosage of from 65 to 175 mg/m$^2$ once every three weeks. In another example of combination therapy in the treatment of gliomas, the mimetic is administered orally in a range of from 50 to 400 mg/day, in two divided doses; and the antineoplastic agent is temozolomide administered at a dosage of from 100 to 250 mg/m$^2$. In another example of combination therapy, the mimetic is administered orally in a range of from 50 to 400 mg/day, in two divided doses, on a continuous dosing regimen; and the antineoplastic agent is 5-Fluorouracil (5-FU) administered either at a dosage of 500 mg/m$^2$ per week (once a week), or at a dosage of 200-300 mg/m$^2$ per day in the case of continuous infusion of the 5-FU. In the case of 5-FU administration on a weekly injection, 5-FU may be administered in combination with a foliate agonist, e.g., Leucovoran (at a dosage of 20 mg/m$^2$/week).

A preferred embodiment of the invention includes monitoring the effects of the treatment with a mimetic for signs of tumor regression, and subsequently adjusting the administration of further doses accordingly. For example, a person with breast carcinoma would be treated locally with an agent such as cyclophosphamide methotrexate 5-FU (CMF) or tamoxifen or local radiation therapy and a mimetic. Subsequent mammography, ultrasound, or physical exams, as compared with the same pre-treatment tests, would direct the course and dosage of further treatment.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, and successive measurements can be used to judge whether or not growth of the tumor has been retarded or even reversed. Relief of disease-related symptoms such as pain, and improvement in overall condition can also be used to help judge effectiveness of treatment. Accordingly, preferred embodiments of the invention include monitoring of the patient after treatment with a mimetic for signs of tumor regression. Such monitoring includes but is not limited to physical exam, CT scan, MRI, mammography, chest X-rays, bone scans, ultra-sounds, bronchoscopy, endoscopy, colonoscopy, laparoscopy, and tests for tumor markers such as PSA, CEA, and CA125. The appropriateness of any form of monitoring will be determined by the nature of the cancer being treated.

EXAMPLES

The following examples are used to assay for bioactivity of Smac mimetics, e.g. as measured by IAP binding, pro-caspase-3 activation or promotion of apoptosis. These assays may also be used to screen for agents (e.g. antagonists) which potentiate such mimetic activity.

Example 1

In vitro IAP (BIR) Binding/Interaction Assay

Interaction between mimetics and IAPs was examined by GST-mediated pull-down assays. Approximately 0.4 mg of a recombinant IAP fragment (second and third BIR motifs of XIAP) is bound to 200 ml of glutathione resin as a GST-fusion protein and incubated with 0.5 mg of radiolabeled mimetics at room temperature. After extensive washing with an assay buffer containing 25 mM Tris, pH 8.0, 150 mM NaCl, and 2 mM dithiothreitol (DTT), the complex is eluted with 5 mM reduced glutathione and visualized by SDS-PAGE with Coomassie staining. This assay demonstrates that the tested mimetics specifically bind IAP.

Example 2

High-Throughput In Vitro Fluorescence Polarization Binding Assay

Sensor: Rhodamine-labeled mimetic (final conc.=1-5 nM)

Receptor: Glutathione-S-transferase/BIR2,3 fusion protein (final conc.=100-200 nM)

Buffer: 10 mM HEPES, 10 mM NaCl, 6 mM magnesium chloride, pH 7.6

1. Add 90 microliters of mimetic/BIR2,3 mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

Tested mimetics significantly and specifically bind the IAP BIR2,3 domain.

3

High Throughput Solid Phase Mimetic-BIR2,3 Binding/Binding-Interference Assay

A. Reagents:
  Neutralite Avidin: 20 µg/ml in PBS.
  Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.

$^{33}$P mimetic 10× stock: $10^{-8}$-$10^{-6}$ M "cold" mimetic supplemented with 200,000-250,000 cpm of labeled mimetic (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma # B-6506), 25 mg Leupeptin (BMB #1017128), 10 mg APMSF (BMB #917575), and 2 mM NaVO$_3$ (Sigma # S-6508) in 10 ml of PBS.

BIR2,3: $10^{-7}$-$10^{-5}$ M biotinylated BIR2,3 domain (supra) in PBS.

B. Preparation of Assay Plates:
Coat with 120 µl of stock N-Avidin per well overnight at 4° C.
Wash 2 times with 200 µl PBS.
Block with 150 µl of blocking buffer.
Wash 2 times with 200 µl PBS.

C. Assay:
Add 40 µl assay buffer/well.
Add 10 µl compound or extract.
Add 10 µl $^{33}$P-mimetic (20-25,000 cpm/0.1-10 pmoles/well=$10^{-9}$-$10^{-7}$ M final conc)
Shake at 25° C. for 15 minutes.
Incubate additional 45 minutes at 25° C.
Add 40 µM biotinylated BIR2,3 (0.1-10 pmoles/40 ul in assay buffer)
Incubate 1 hour at room temperature.
Stop the reaction by washing 4 times with 200 µM PBS.
Add 150 µM scintillation cocktail.
Count in Topcount.

D. Controls for all Assays (Located on Each Plate):
a. Non-specific binding
b. Soluble (non-biotinylated BIR2,3) at 80% inhibition Mimetics significantly and specifically bind the IAP BIR2,3 domain.

Example 4

Hela Cell Extracts: Radiolabeled Procaspase-3 Activation Assay 20 mg S-100 extracts of HeLa cells were incubated alone (Control), or with mimetics (50 nM) nM, or with 30-1000 mM of N-terminal Smac peptides in different lengths. The reactions were carried out with the addition of 1 mM dATP, 1 mM additional MgCl2, 0.2 mg/ml horse heart cytochrome c, and 1 ml of in vitro translated, $^{35}$S-labeled caspase-3 in a final volume of 20 ml. The reaction mixtures were incubated at 30° C. for 1 hr followed by electrophoresis on a 15% PAGE gel. The gel was subsequently transferred onto a nitrocellulose filter and exposed to a phosphoimaging cassette. Mimetics and Smac fragments significantly promoted activation of procaspase-3, whereas negative control Smac-7R did not.

Example 5

Hela Cell Extracts: Spectrofluorometric Procaspase-3 Activation Assay

Human Hela S3 cells were cultured in 150-mm tissue culture dishes in DMEM medium (Dulbecco's modified eagle's medium containing 100 U/ml of penicillin and 100 ug/ml of streptomycin sulfate) supplemented with 10% (v/v) fetal calf serum, and grown in monolayer at 37° C. in an atmosphere of 5% CO$_2$. Cells at 70% confluence were washed once with 1× phosphate-buffered saline (PBS) and harvested by centrifugation at 800×g for 5 min at 4° C. The cell pellets were resuspended in 3 volume of Buffer A (20 mM Hepes-KOH, pH 7.5, 10 mM KCL, 1.5 mM MgCl2, 1 mM sodium EDTA, 1 mM sodium EGTA, 1 mM DTT, and 0.1 mM PMSF). Human c-IAP-1 or c-IAP-2, or XIAP either full length of truncated proteins that contain the first three BIR domains, or the second and third BIR domains are added to the HeLa cell extracts and the caspase activation reaction is started by adding 1 mM dATP and 300 nM cytochrome c. The caspase-3 activity is measured by spectrofluorometric assay as previously described by MacFarlane et al. (1997, J. Cell Biol. 137, 469-479). Aliquots of 8 mg of S-100 prepared as in Liu et al. were assayed in 96-well microtiter format in a 150 ml of reaction containing 0.1 mM Hepes, PH 7.4, 2 mM DTT, 0.1% (w/v) Chaps, and 1% (w/v) Sucrose. The reactions were started by adding caspase specific fluorogenic substrate (Enzyme Systems, CA) to the final concentration of 20 mM and continued at 37° C. for 30 min. Liberation of AFC from the substrates was monitored continuously using excitation/emission wavelenth paires of 400/505 nm. Mimetics and Smac fragments (except 7R) significantly promoted activation of procaspase-3.

Example 6

Reconstituted Recombinant Radiolabeled Procaspase-3 Activation Assay

Mimetics and N-terminal Smac peptides (30-3000 mM) were incubated with recombinant human Apaf-1 (40 nM), recombinant human procaspase-9 (2 nM), purified horse heart cytochrome c (nM) and mouse XIAP (70 nM) in the presence of 1 mM dATP, 1 mM MgCl$_2$ and 1 ml of in vitro translated, $^{35}$S-labeled caspase-3 in a final volume of 20 ml. The reaction mixtures were incubated at 30° C. for 1 hr followed by electrophoresis on a 15% PAGE gel. The gel was transferred onto a nitrocellulose filter and exposed to a phosphoimaging cassette. Active Smac protein (50 nM) and an inactive peptide Smac-7R (3000 mM) are also included as controls. Mimetics and Smac fragments (except 7R) significantly promoted activation of procaspase-3.

Example 7

Reconstituted Recombinant Spectrofluorometric Procaspase-3 Activation Assay

A reconstituted recombinant procaspase-3 activation system is constructed as described above except the human caspase-3 is produced from bacterial expression as described in Liu et al., 1997 (supra) and is not labeled. The caspase-3 activity is measured by spectrofluorometric assay as previously described by MacFarlane et al. (1997, J. Cell Biol. 137, 469-479). Aliquots of 8 mg of S-100 prepared as above were assayed in 96-well microtiter format in a 150 ml of reaction containing 0.1 mM Hepes, PH 7.4, 2 mM DTT, 0.1% (w/v) Chaps, and 1% (w/v) Sucrose. The reactions were started by adding a caspase specific fluorogenic substrate (Enzyme Systems, CA) to the final concentration of 20 mM and continued at 37° C. for 30 min. Liberation of AFC from the substrates was monitored continuously using excitation/emission wavelenth paires of 400/505 nm. Mimetics and Smac fragments (except 7R) significantly promoted activation of procaspase-3.

Example 8

Cell-Based Assay: Smac Peptides Potentiate Apoptosis Induced by UV or Etoposide in Cultured HeLa Cells 0.75×105 of HeLa—S cells/well were plated in 48-well tissue culture plate. Cells were incubated with 1 mM inactive Smac peptide or with 1 mM N-terminal 4-amino acid Smac peptide, with selected mimetics, or with vehicle only (Control) for 12 hr. The cells were then treated with either 320,000 microjoules of UV irradiation using a Stratalinker or with 100 mM chemotherapeutic Etoposide. Cells were then stained with 1 mg/ml Hoechst 33342 dye at different time points and apoptotic cells were counted as those with condensed nuclear chromatin under a fluorescent microscopy. Mimetics, including wild-type Smac peptides, showed significant increases in apoptotic induction at 2, 4 and 6 hrs (for UV insult) and at 10 and 20 hr (for etoposide).

Example 9

In Vivo Metastasis Assay

Immunosuppressed mice (athymic nude/nude SCID females from Harlan Sprague Dawley) are housed in autoclaved cages with microisolator tops, and all manipulations of the animals are done in a laminar flow hood after wiping down both the hood, gloves and cages with ABQ sterilant. The mice are fed sterile Pico Lab Chow (Purina) and autoclaved St. Louis tap water. Mimetics are administered intra-gastrically daily to the mice in sterile water containing 2% carboxymethyl cellulose via sterile, disposable animal feeding needles (Poper & Sons Cat #9921; 20 g×1.5"), seven days a week between 7:00 and 8:00 am. The compounds and control (sterile water plus 2% carboxymethyl cellulose) are kept stored at $-80°$ C. wrapped in aluminum foil to prevent any light induced changes, and each day's supply is thawed just prior to use.

Compounds are tested for their effects on the metastatic potential of C8161 cells injected intravenously via the tail vein: at 40 and 100 mg/kg, compared to the control. The concentration of the compounds in the vials used to give the 100 mg/kg doses are 2.5 times that in the 40 mg/kg dose so that approximately the same volume is used in both cases, approximately 0.5 mL/animal. The experiments start with nine animals per group at day −4. On day zero, $2\times10^5$ C8161 cells in cold Hank's Balanced Salt Solution (HBSS) are injected intravenously via tail vein inoculation. The protocol is continued for an additional 24 days, at which time the animals are sacrificed and their lungs removed and fixed in a solution of Bouins/formaldehyde (5 parts: 1 part). Tumors are quantified on the entire surface of the lungs by rotating the lungs and counting the tumors on each lobe using a 6× magnifying glass. Statistical analysis is performed using the statistical package of Microsoft's Excel spreadsheet software.

The effects of test mimetics, at two different concentrations, on the metastatic potential of C8161 cells in SCID mice are evaluated: oral gavaging of the animals with mimetics significantly reduces the number of lung metastases in the SCID mouse population.

Example 10

In Vivo Combination Therapy: B.I.D. & Q.I.D.

The effect of in vivo combination therapy of mimetics (20 or 80 mpk/dosing p.o. or i.p.) with chemotherapies paclitaxel (5 or 20 mpk), 5-Fu (50 mpk), vincristine (1 mpk) or cytoxan (100 mpk, BID, ip) on HTB 177 xenografts (NCI-H460, a human lung large cell carcinoma) using two and four times a day dosing is demonstrated in athymic nu/nu female mice, 5-6 weeks old. On Day 0, HTB 177 cells, $3\times10^6$, are injected s.c. into the flank of 220 mice and the mice divided into treatment and control groups:

Mimetics were dissolved in 20% hydroxyl-propyl-betacyclodexatrin (Vehicle I); 0.2 ml of mimeic solution was the dosing volume. Paclitaxel was dissolved in a diluted ethanol/cremophor EL solution (Vehicle II) and the i.p. dosing volume for paclitaxel was 0.1 ml. Cytoxan, 5-FU, and Vincristine were dissolved in sterile water. The 80 mpk dosing mimetic solution is made by adding 17 ml of 20% HPBCD to a 50 ml tube containing 136 mg of mimetic to dissolve. The mixture was sonicated until a complete solution was made. The 20 mpk dosing solution is made by placing 2 ml of the 80 mpk solution into a 15 ml tube, adding 6 ml of 20% HPBCD, and vortexing the solution to mix it.

Tumor cells are inoculated into mice in the morning of Day 0, and the mice weighed, randomized, and ear-marked afterwards. Drug treatment begins at 7:30 am on Day 4. The animals are dosed with mimetic or vehicle I solution, at 7:30 am, and 7:30 pm, 7 days a week. Tumor growth is quantitated by measuring tumor volume on Day 7 and Day 14. Both mimetic and chemotherapies demonstrate inhibition; combination therapies provide enhanced inhibition over either therapy alone.

Example 11

In Vivo Therapy in the WAP-RAS Transgenic Model

Mimetic and Paclitaxel combination efficacy is also evaluated in the Wap-ras transgenic model. This model is used in a therapeutic mode in which treatments are initiated after mice had well developed tumors.

Mimetics (20 mpk/dosing po) were dissolved in 20% hydroxyl-propyl-betacyclodextrin (Vehicle I). 0.2 ml of mimetic solution is the oral dosing volume. Paclitaxel (5 mpk/dosing ip) was dissolved in a diluted ethanol/cremophor EL solution (vehicle II) and the i.p. dosing volume for paclitaxel was 0.1 ml.

The mice are weighed, randomized, and ear-marked on Day 0. Mimetic treatment and Vehicle I treatment began on Day 1 and continued every 12 hours until Day 21. Paclitaxel and Vehicle II treatments are started on Day 4 and continued daily on Day 5, 6, and 7. Wap-ras tumors do not respond to treatment with Paclitaxel but do respond to mimetic treatment at 20 mpk alone and combined therapy enhanced efficacy.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Exemplary Dimers
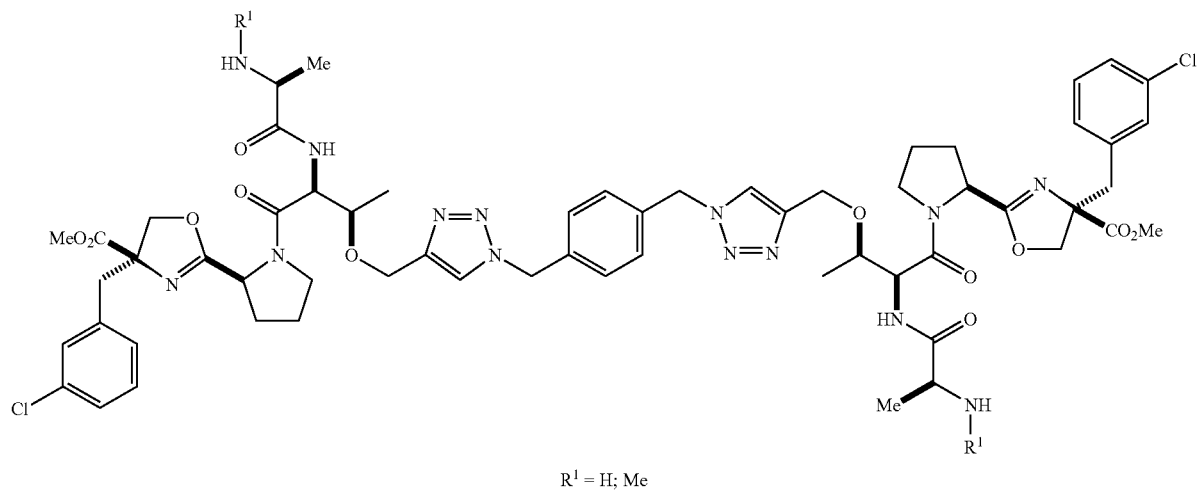
$R^1$ = H; Me
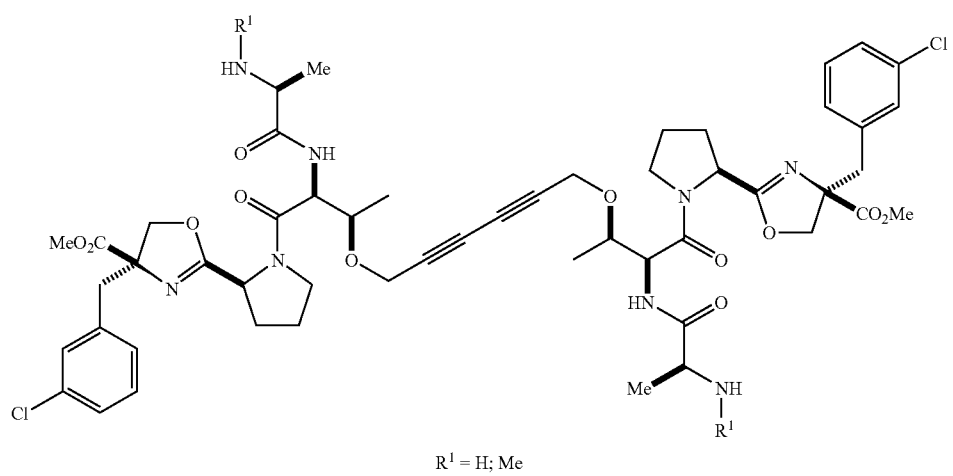
$R^1$ = H; Me
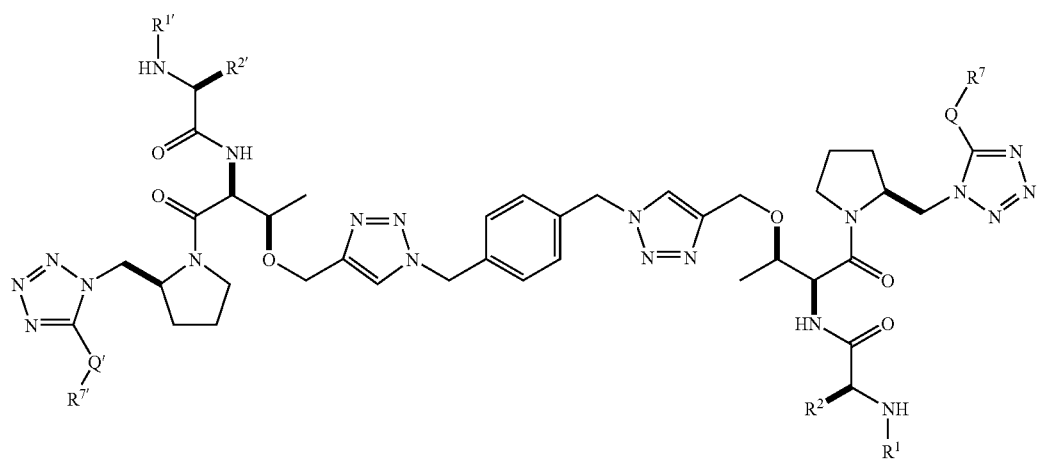

R1 and R1' can be the same or different and include H; Me

R2 and R2' can be the same or different and include Me; Et

R7 and R7' can be the same or different and include aryl, heteroaryl, CH2aryl, CH2heteroaryl, branched alkyl, cycloalkyl, functionalized alkyl or cycloalkyl (functionalization may include, inter alia, unsaturation, heteroatoms, aryl, heteroaryl)

Q and Q' can be the same or different and include O, S, NR1

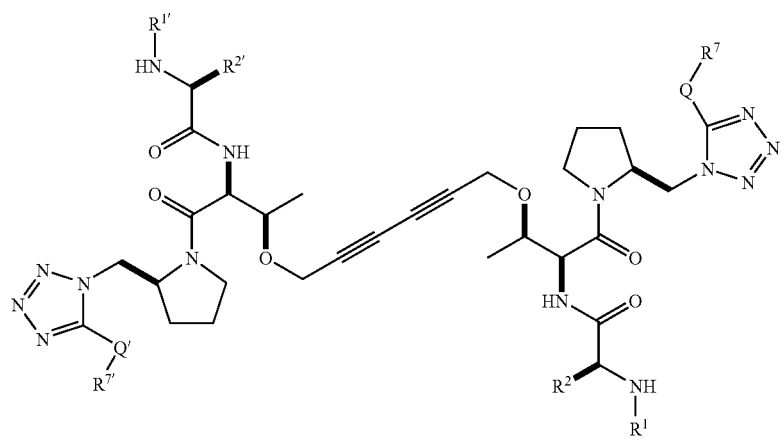

R1 and R1' can be the same or different and include H; Me

R2 and R2' can be the same or different and include Me; Et

R7 and R7' can be the same or different and include aryl, heteroaryl, CH2aryl, CH2heteroaryl, branched alkyl, cycloalkyl, functionalized alkyl or cycloalkyl (functionalization may include, inter alia, unsaturation, heteroatoms, aryl, heteroaryl)

Q and Q' can be the same or different and include O, S, NR1

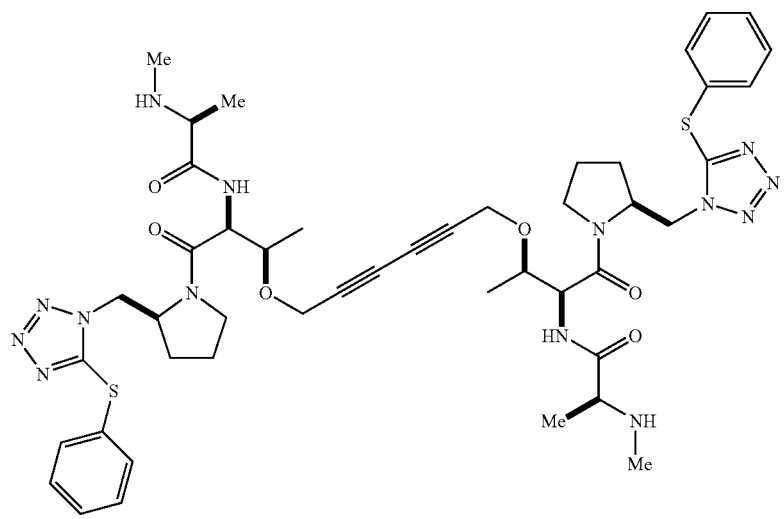

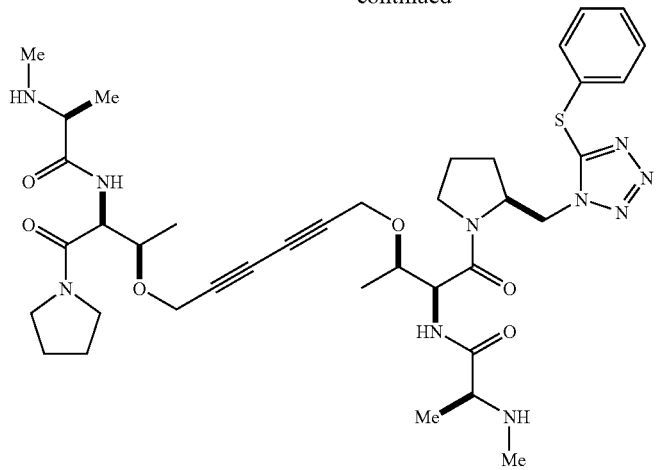

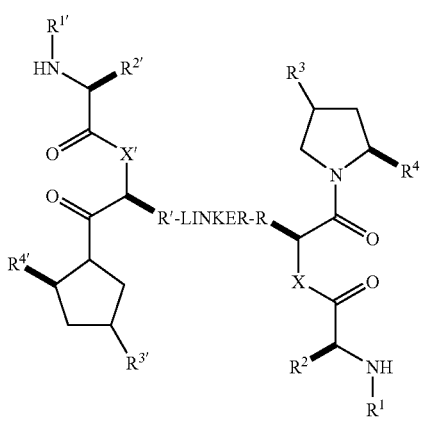

R4' can include:

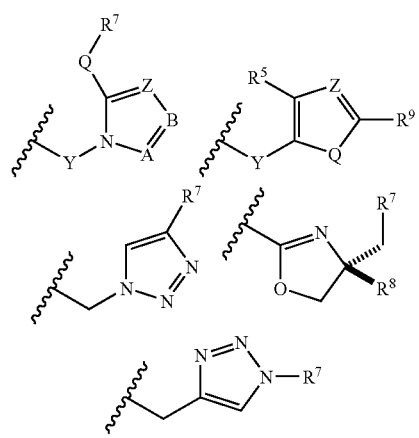

R and R' can be the same or different and include CH2; CHMe; CHEt; CMe2; 1,1-disubstituted cyclopropyl R1 and R1' can be the same or different and include H; Me R2 and R2' can be the same or different and include Me; Et R3 and R3' can be the same or different and include H; Me; halogen; straight chain or branched alkyl; cycloalkyl; aryl; heteroaryl; functionalized alkyl or cycloalkyl (functionalization may include, inter alia, unsaturation, heteroatoms, aryl and heteroaryl); OR5; NR5R6

R4 can be chosen from R5 and R4'

R5 and R6 can include H, Me, straight chain alkyl, or any of R7

R7=aryl, heteroaryl, branched alkyl, cycloalkyl, functionalized alkyl or cycloalkyl (functionalization may include, inter alia, unsaturation, heteroatoms, aryl, heteroaryl)

R8=CH2OR5, CH2OC(O)R5, CH2OC(O)NHR5, CO2R5, C(O)NR5R6

R9=H, OR5, NR5R6

A, B, and Z includes CH, N, C—R7

Q=CH2, CHMe, O, S, NR5

X and X' can be the same or different and include NH, O, CH2

Y=CH2, C(O), C(S), CHMe

LINKER is a contiguous chain that can incorporate substitution, heteroatoms, unsaturation (alkene, alkyne), cyclic, aromatic and heteroaromatic fragments.

Examples include, but are not limited to:

Linkers need not be symmetrical

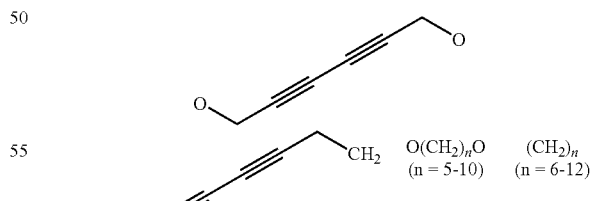

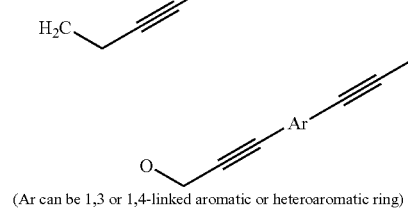

(Ar can be 1,3 or 1,4-linked aromatic or heteroaromatic ring)

Examples of Unsymmetrical Linkers:

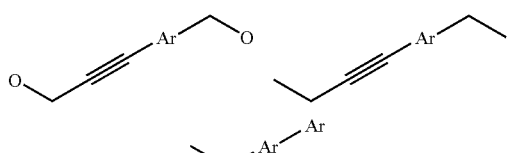

(Ar can be 1,3 or 1,4-linked aromatic or heteroaromatic ring)

O(CH$_2$)$n$O  
n = 5-12

(CH$_2$)$n$  
n = 6-12

Examples of Truncated Linkers

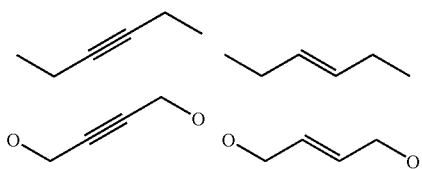

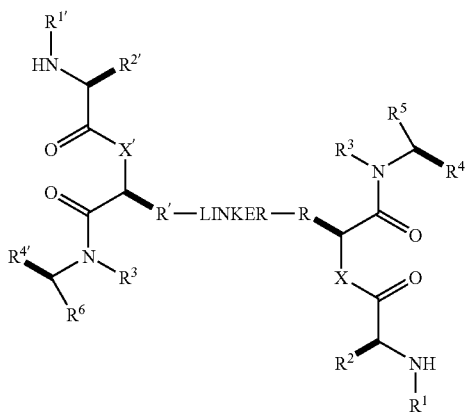

R$^{4'}$ can include:

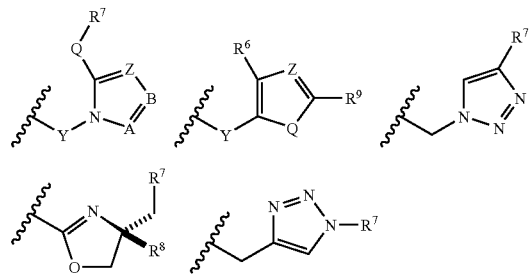

R and R' can be the same or different and include CH2; CHMe; CHEt; CMe2; 1,1-disubstituted cyclopropyl R1 and R1' can be the same or different and include H; Me R2 and R2' can be the same or different and include Me; Et R3 and R3' can be the same or different and include H; Me; straight chain or branched alkyl; cycloalkyl; functionalized alkyl or cycloalkyl (functionalization may include, inter alia, unsaturation, heteroatoms, aryl and heteroaryl)

R4 can be chosen from R5 and R4'

R5 and R6 can include H, Me, straight chain alkyl, or any of R7

R7=aryl, heteroaryl, branched alkyl, cycloalkyl, functionalized alkyl or cycloalkyl (functionalization may include, inter alia, unsaturation, heteroatoms, aryl, heteroaryl)

R8=CH2OR5, CH2OC(O)R5, CH2OC(O)NHR5, CO2R5, C(O)NR5R6

R9=H, OR5, NR5R6

A, B, and Z includes CH, N, C—R7

Q=CH2, CHMe, O, S, NR5

X and X' can be the same or different and include NH, O, CH2

Y=CH2, C(O), C(S), CHMe

LINKER is a contiguous chain that can incorporate substitution, heteroatoms, unsaturation (alkene, alkyne), cyclic, aromatic and heteroaromatic fragments.

Examples include, but are not limited to:

Linkers can be non-symmetrical

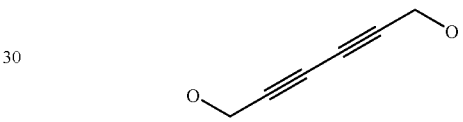

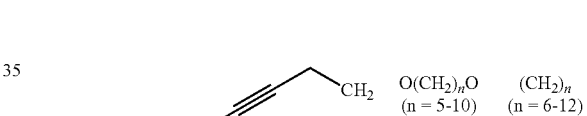

O(CH$_2$)$n$O  
(n = 5-10)

(CH$_2$)$n$  
(n = 6-12)

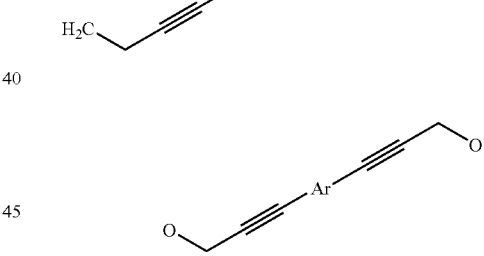

(Ar can be 1,3 or 1,4-linked aromatic or heteroaromatic ring)

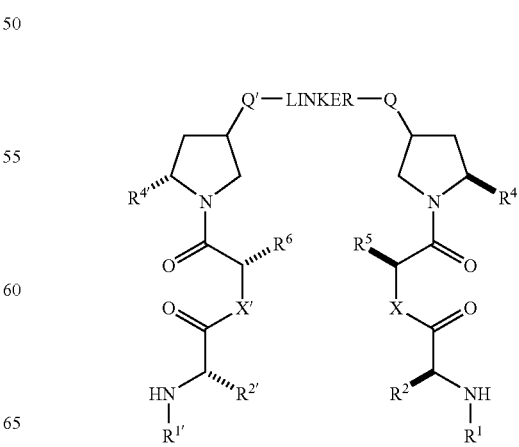

-continued

R4' can include:

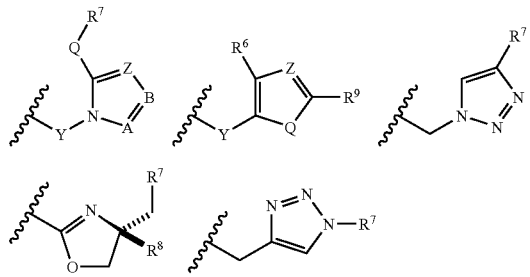

R1 and R1' can be the same or different and include H; Me

R2 and R2' can be the same or different and include Me; Et

R4 can be chosen from R5 and R4'

R5 and R6 can include H, Me, straight chain alkyl, or any of R7

R7=aryl, heteroaryl, branched alkyl, cycloalkyl, functionalized alkyl or cycloalkyl (functionalization may include, inter alia, unsaturation, heteroatoms, aryl, heteroaryl)

R8=CH2OR5, CH2OC(O)R5, CH2OC(O)NHR5, CO2R5, C(O)NR5R6

R9=H, OR5, NR5R6

A, B, and Z includes CH, N, C—R7

Q and Q' can be the same or different and include CH2, CHMe, O, S, NR5

X and X' can be the same or different and include NH, O, CH2

Y=CH2, C(O), C(S), CHMe

LINKER is a contiguous chain that can incorporate substitution, heteroatoms, unsaturation (alkene, alkyne), cyclic, aromatic and heteroaromatic fragments.

Examples include, but are not limited to:

Linkers can be non-symmetrical

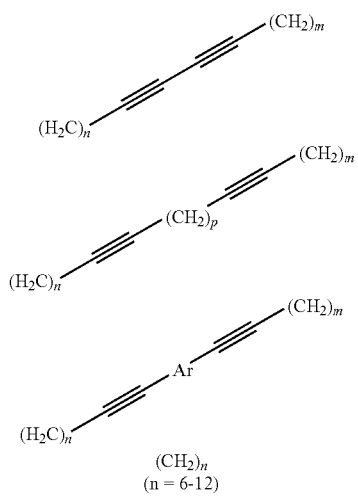

n, m = 1-6
p = 0-6
(Ar can be 1,3 or 1,4-linked aromatic or heteroaromatic ring)

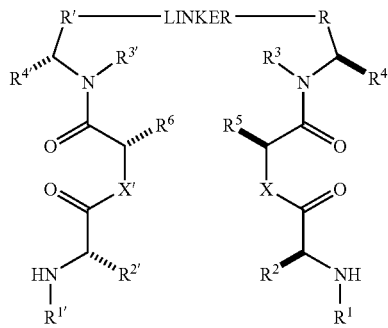

R4' can include:

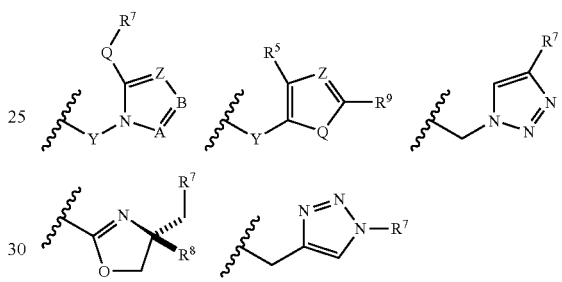

R and R' can be the same or different and include CH2; CHMe; CHEt; CMe2; 1,1-disubstituted cyclopropyl R1 and R1' can be the same or different and include H; Me R2 and R2' can be the same or different and include Me; Et R3 and R3' can be the same or different and include H; Me; straight chain or branched alkyl; cycloalkyl; functionalized alkyl or cycloalkyl (functionalization may include, inter alia, unsaturation, heteroatoms, aryl and heteroaryl)

R4 can be chosen from R5 and R4'

R5 and R6 can include H, Me, straight chain alkyl, or any of R7

R7=aryl, heteroaryl, branched alkyl, cycloalkyl, functionalized alkyl or cycloalkyl (functionalization may include, inter alia, unsaturation, heteroatoms, aryl, heteroaryl)

R8=CH2OR5, CH2OC(O)R5, CH2OC(O)NHR5, CO2R5, C(O)NR5R6

R9=H, OR5, NR5R6

A, B, and Z includes CH, N, C—R7

Q=CH2, CHMe, O, S, NR5

X and X' can be the same or different and include NH, O, CH2

Y=CH2, C(O), C(S), CHMe

LINKER is a contiguous chain that can incorporate substitution, heteroatoms, unsaturation (alkene, alkyne), cyclic, aromatic and heteroaromatic fragments.

Examples include, but are not limited to:

Linkers can be non-symmetrical

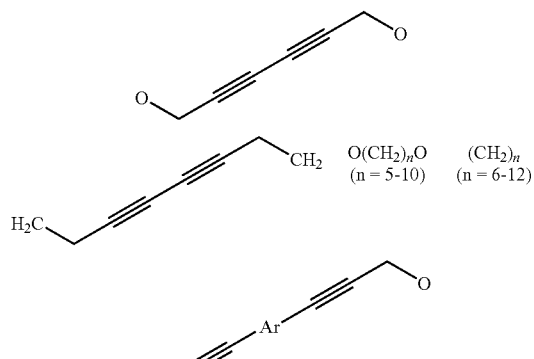

(Ar can be 1,3 or 1,4-linked aromatic or heteroaromatic ring)

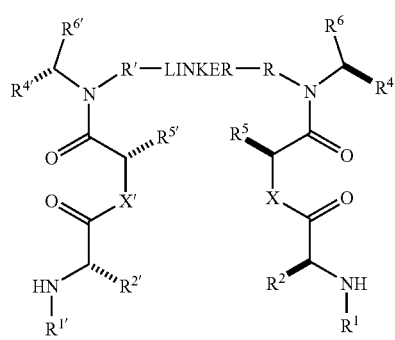

$R^{4'}$ can include:

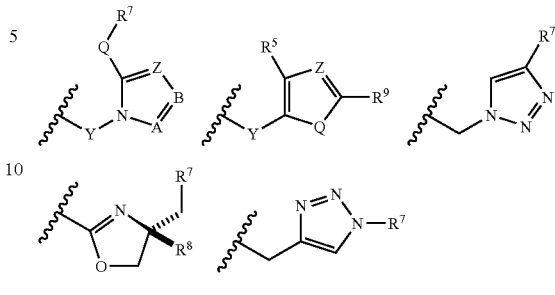

R and R' can be the same or different and include CH2; C(O)

R1 and R1' can be the same or different and include H; Me

R2 and R2' can be the same or different and include Me; Et

R4 can be chosen from R5 and R4'

R5, R5', R6, R6' can be the same or different and include H, Me, straight chain alkyl, or any of R7

R7=aryl, heteroaryl, branched alkyl, cycloalkyl, functionalized alkyl or cycloalkyl (functionalization may include, inter alia, unsaturation, heteroatoms, aryl, heteroaryl)

R8=CH2OR5, CH2OC(O)R5, CH2OC(O)NHR5, CO2R5, C(O)NR5R6

R9=H, OR5, NR5R6

A, B, and Z includes CH, N, C—R7

Q=CH2, CHMe, O, S, NR5

X and X' can be the same or different and include NH, O, CH2

Y=CH2, C(O), C(S), CHMe

LINKER is a contiguous chain that can incorporate substitution, heteroatoms, unsaturation (alkene, alkyne), cyclic, aromatic and heteroaromatic fragments.

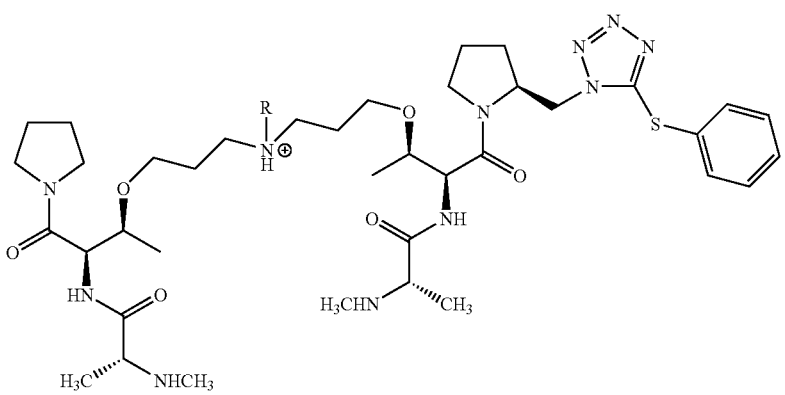

-continued
R = H, alkyl, branched alkyl
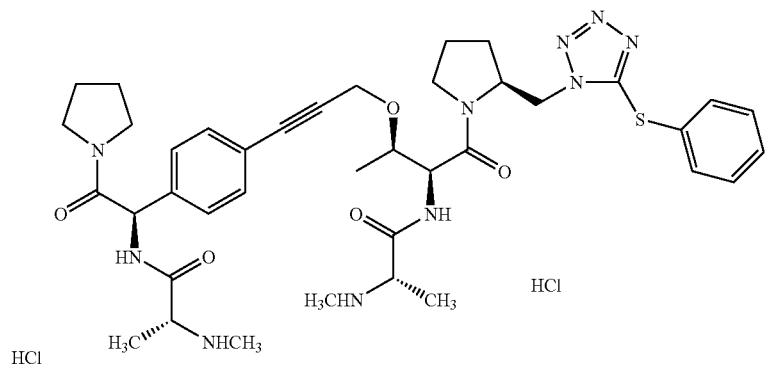
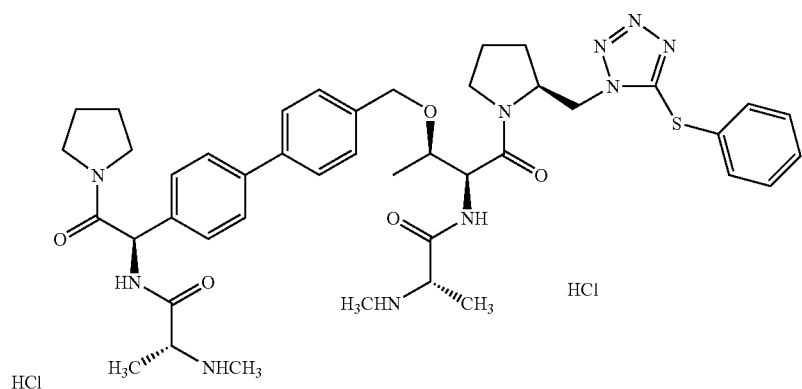
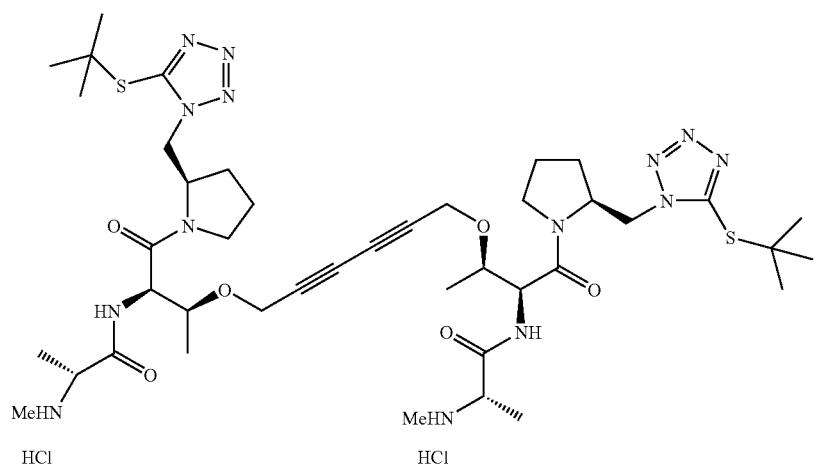

-continued
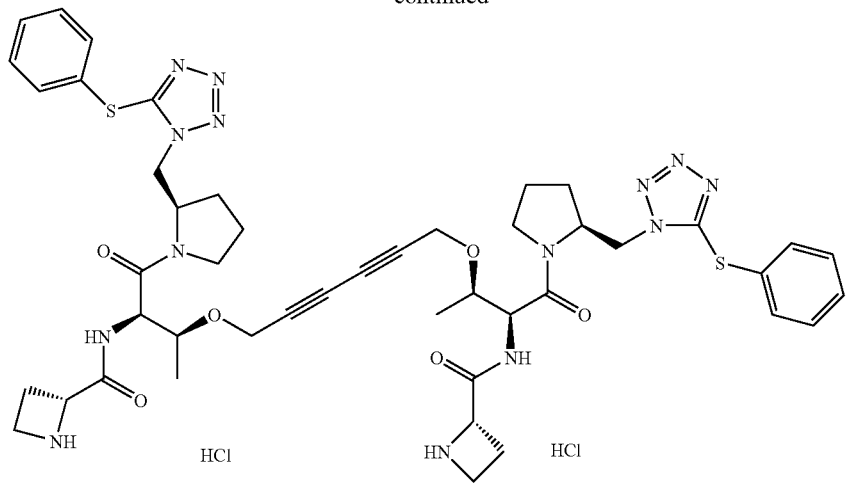
Exemplary Monomers
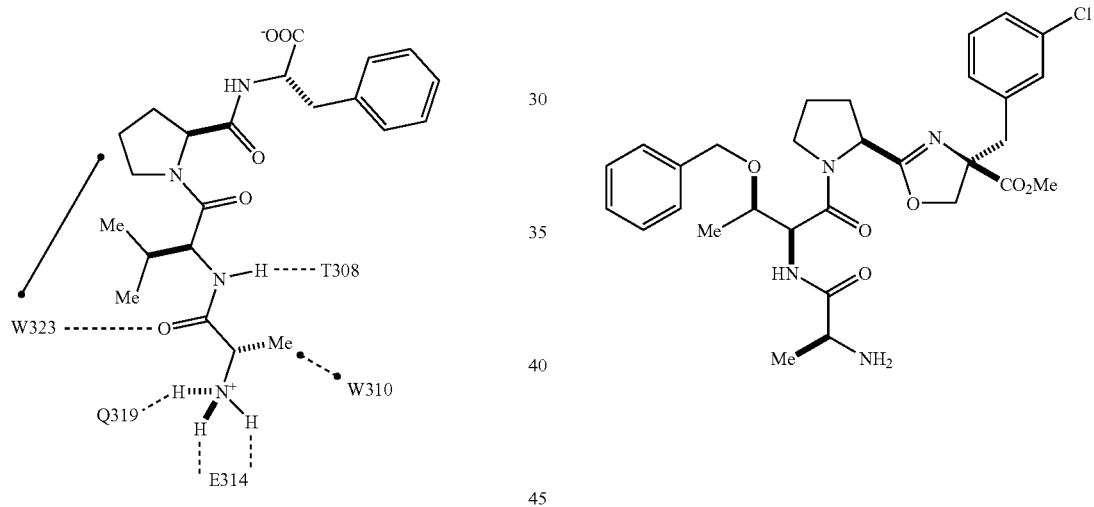
-continued
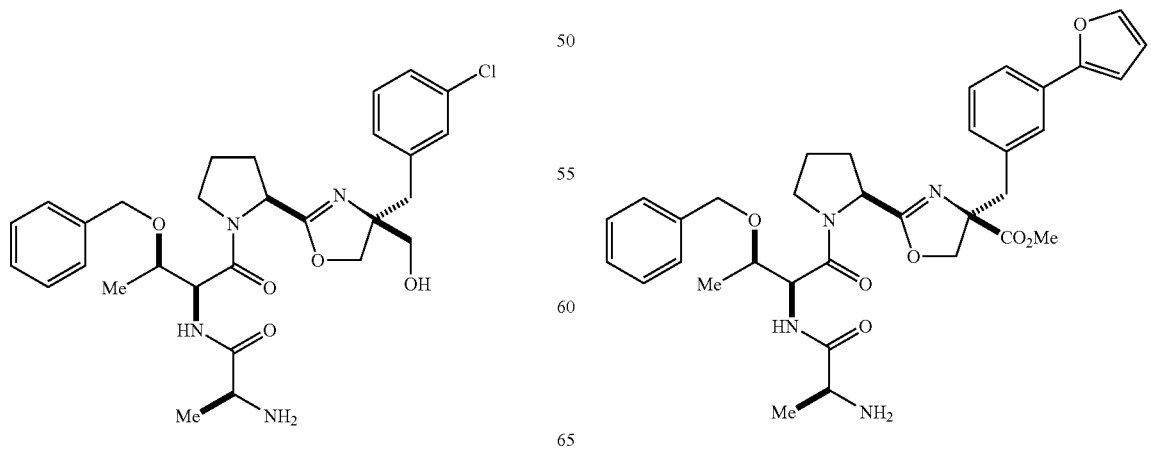

-continued
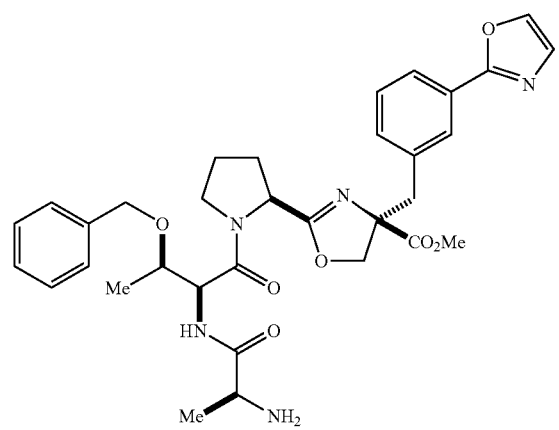
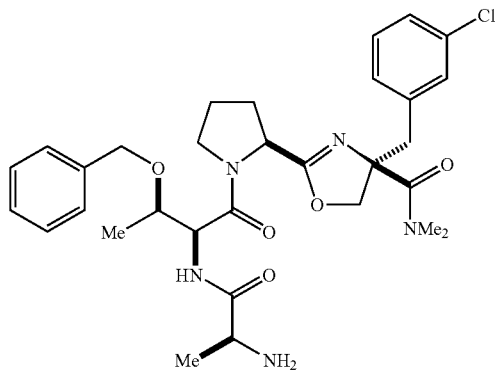
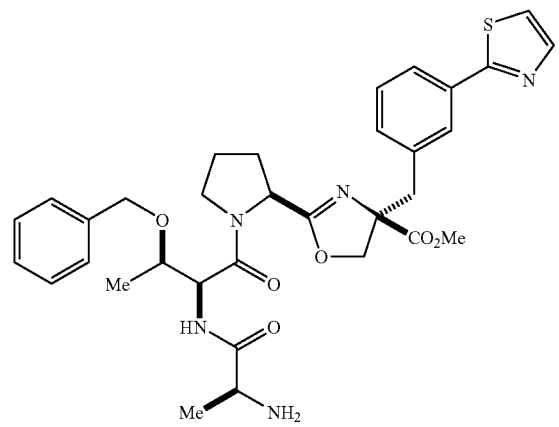
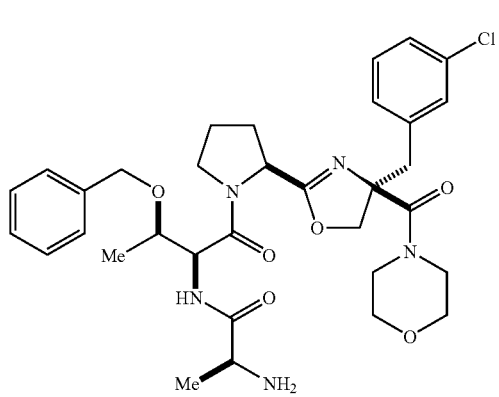
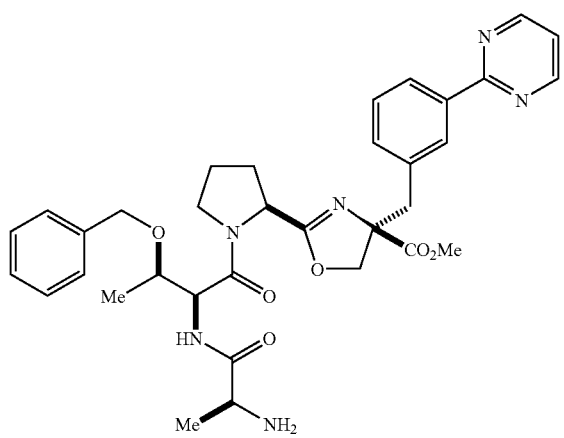
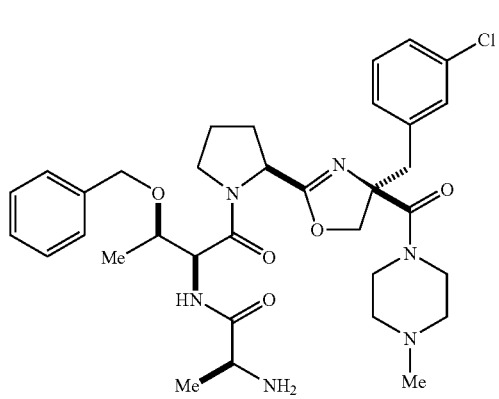
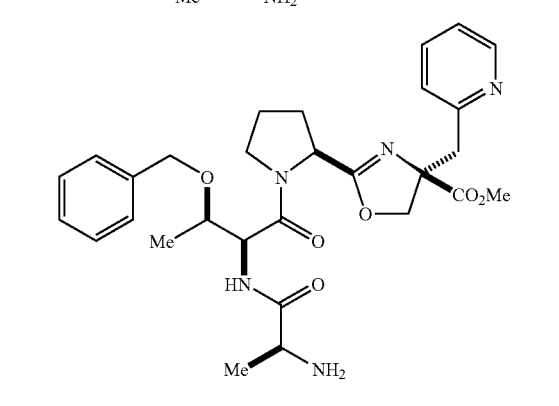
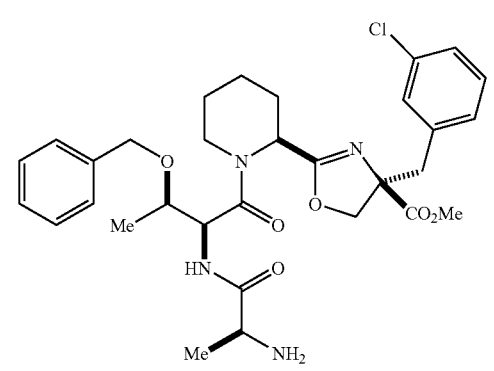

41
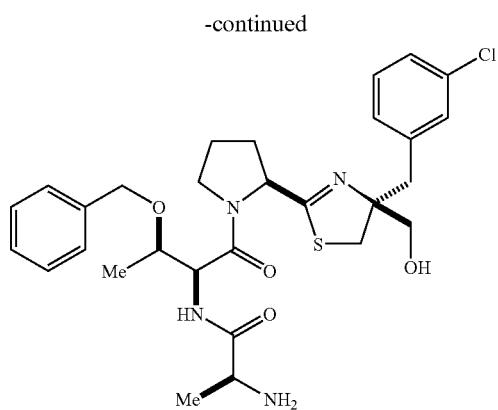
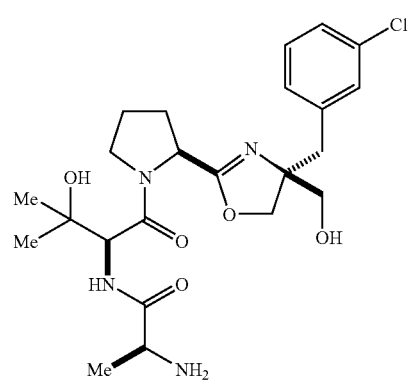
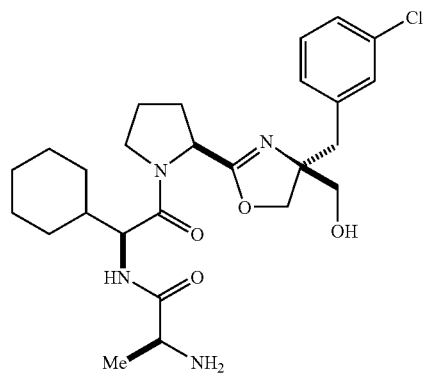
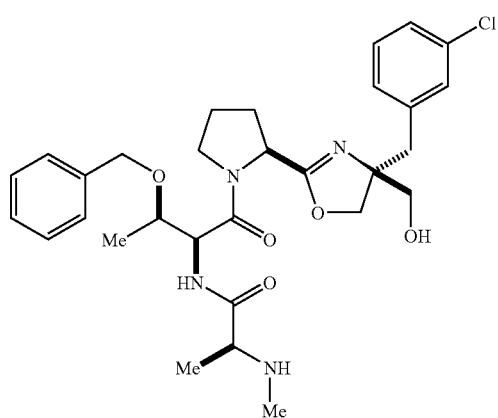
42
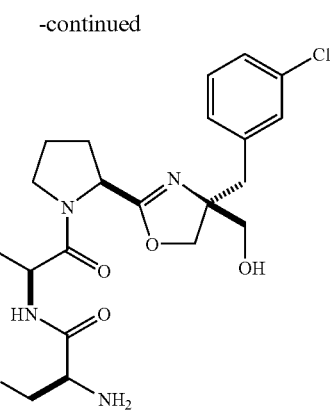
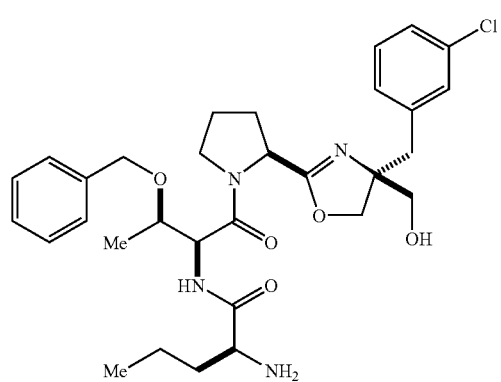
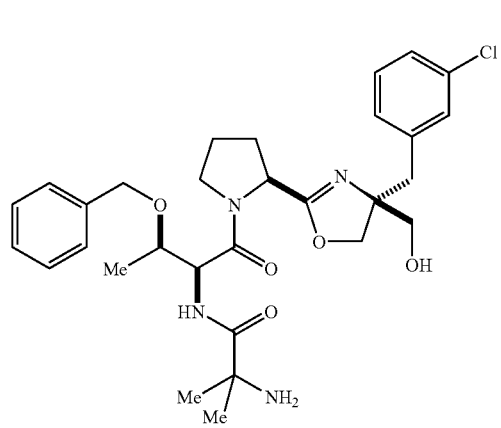
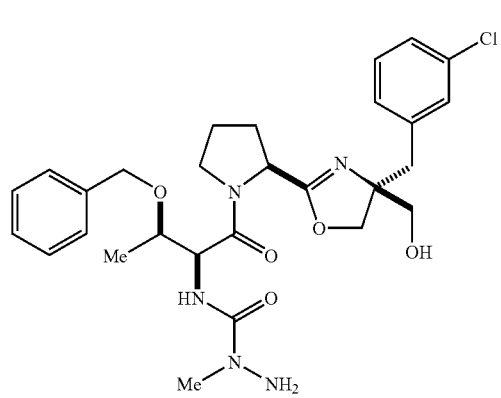

-continued
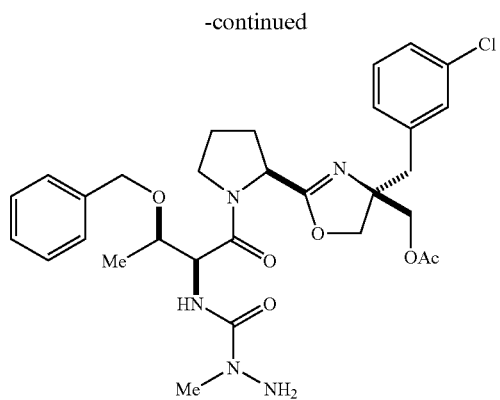
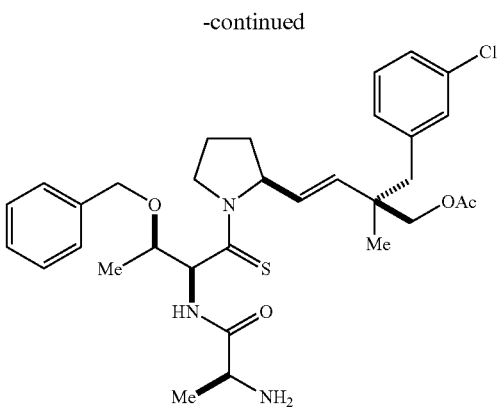
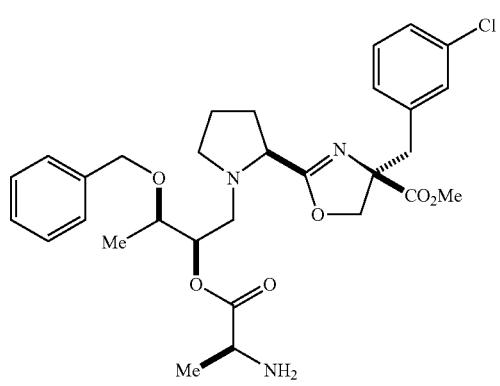
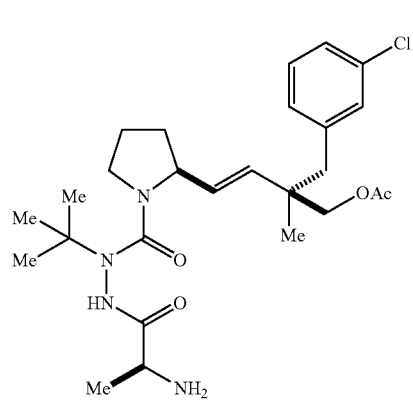
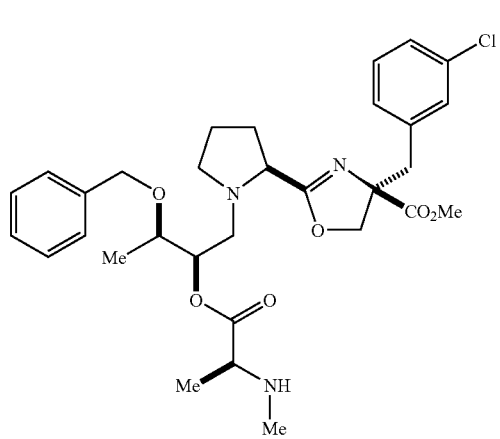
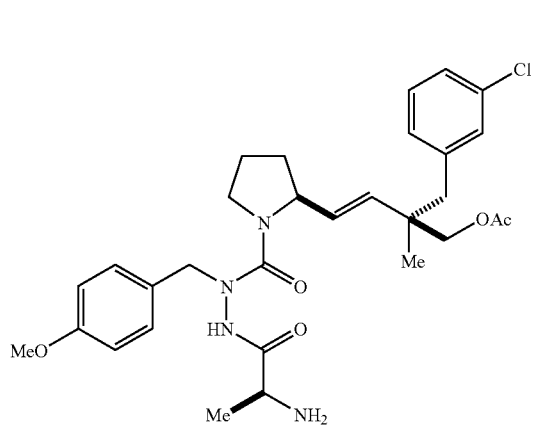
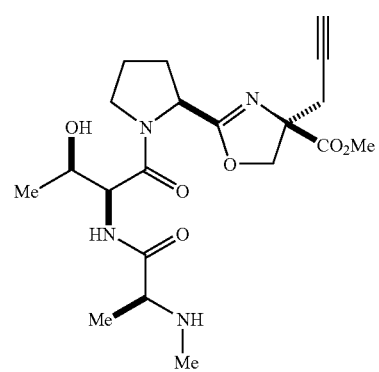
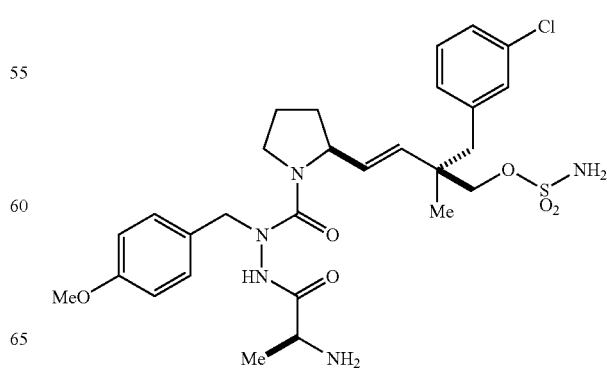

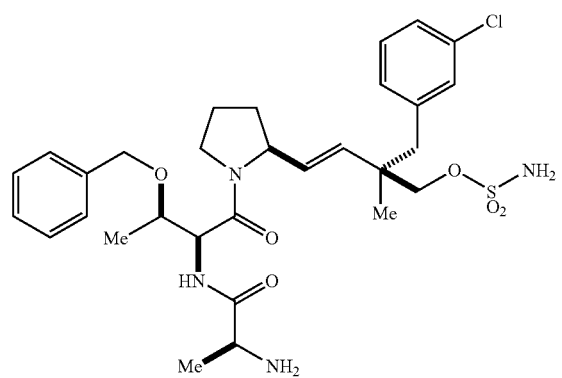
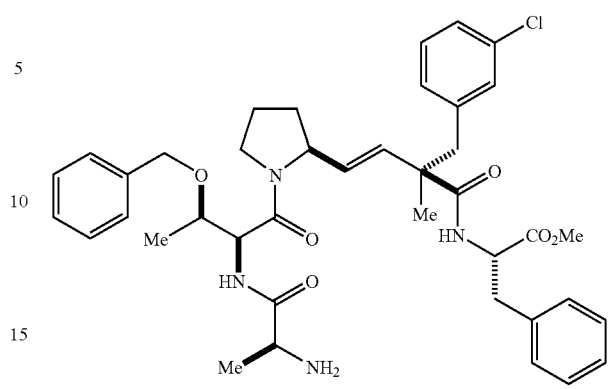
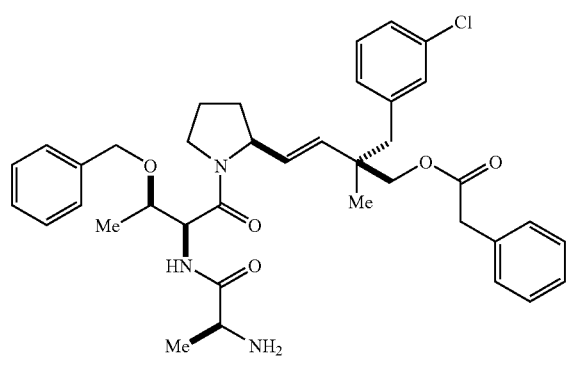
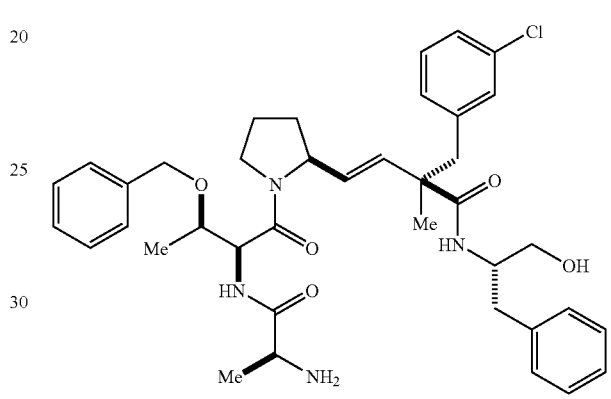
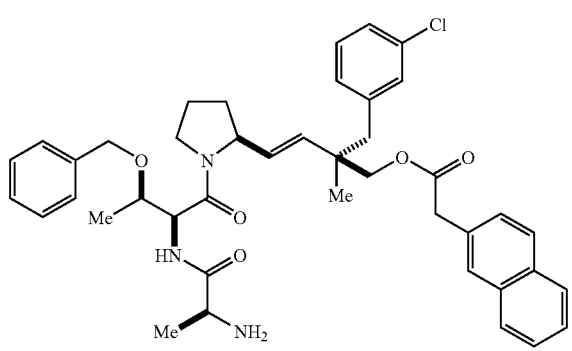
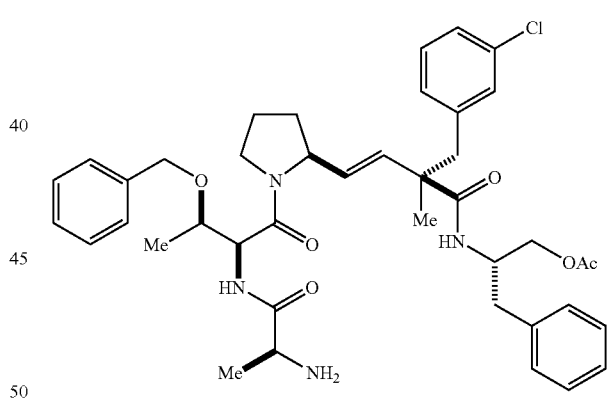
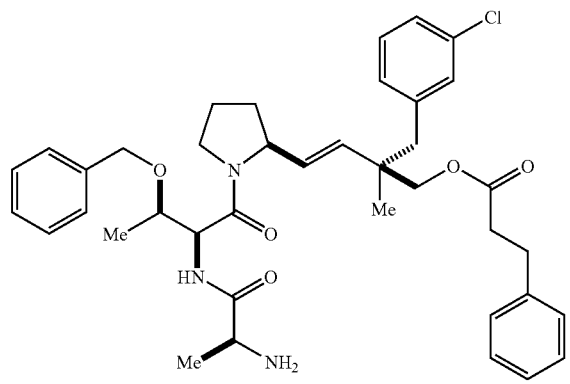
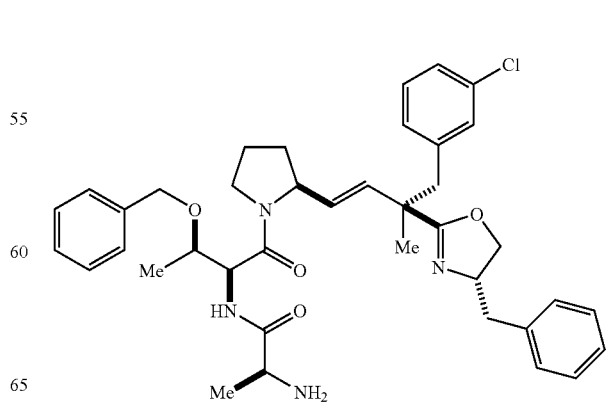

-continued
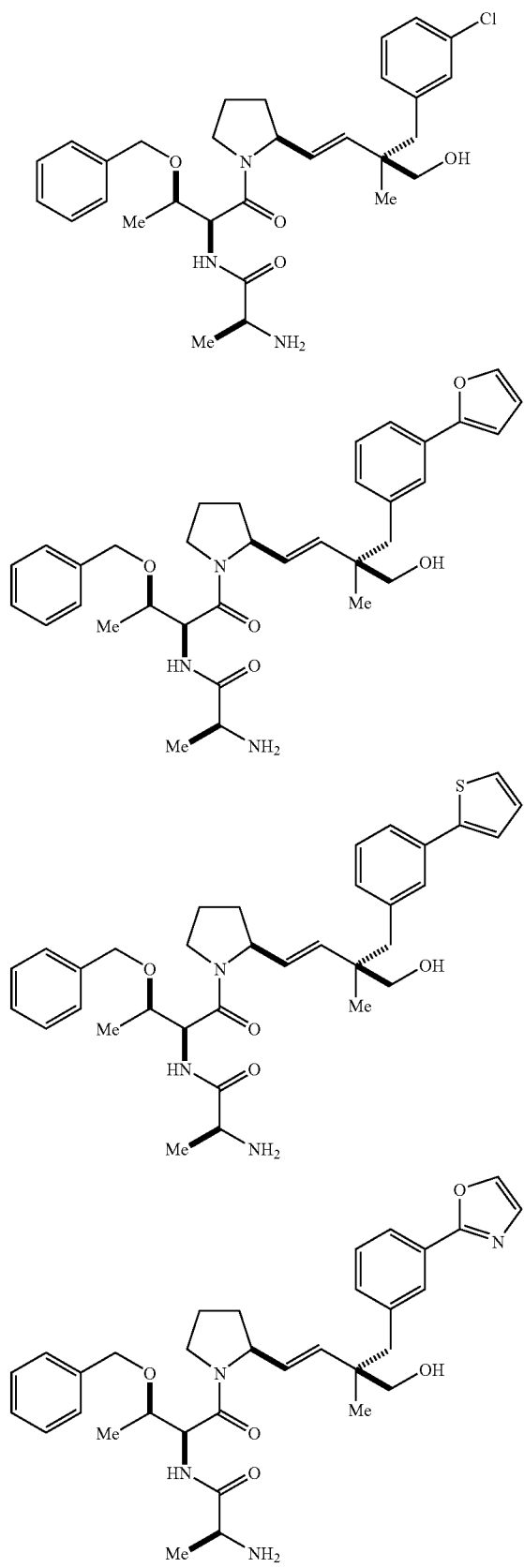
-continued
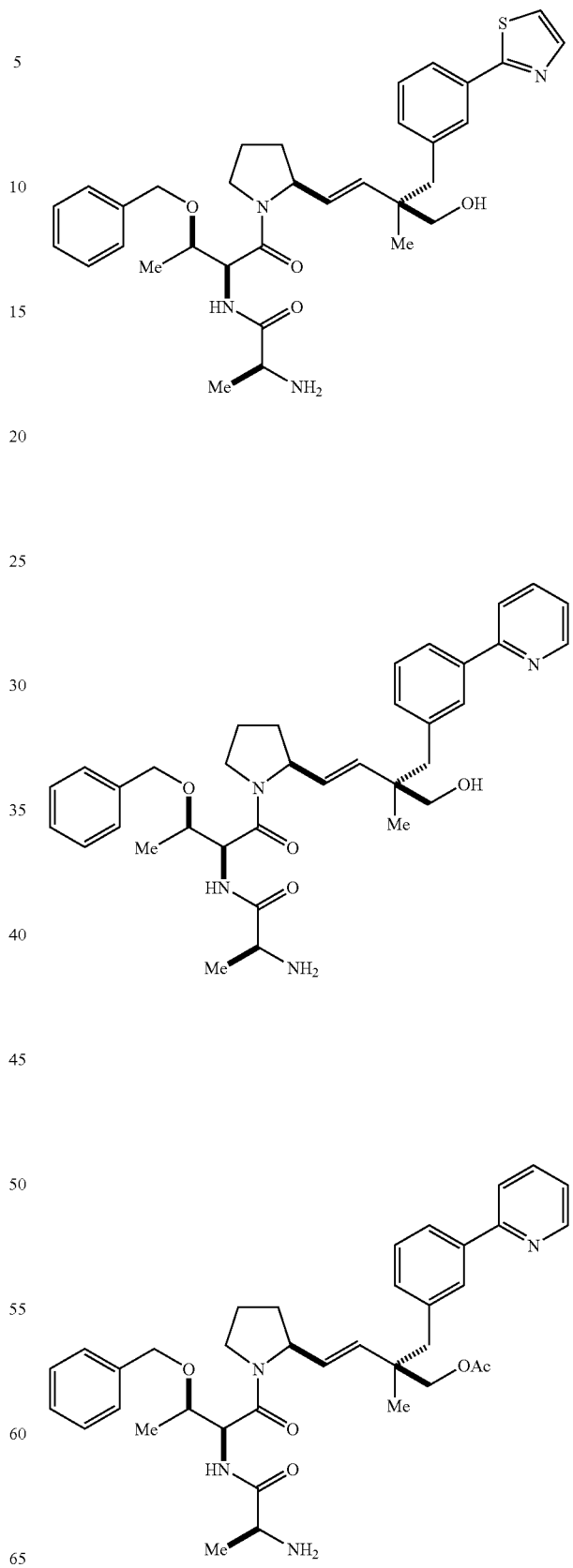

-continued
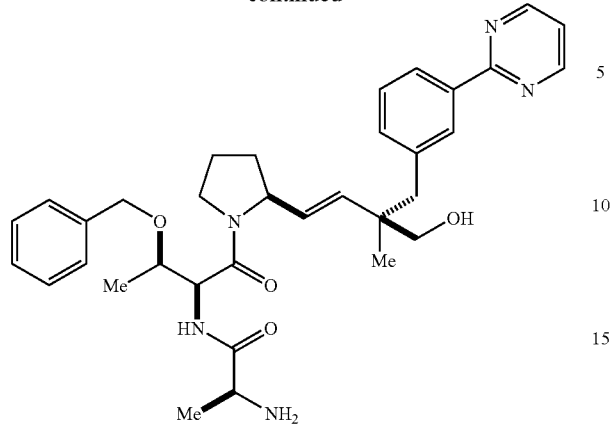
Experimental procedure
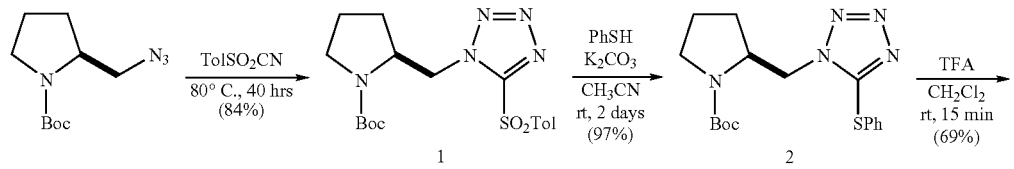
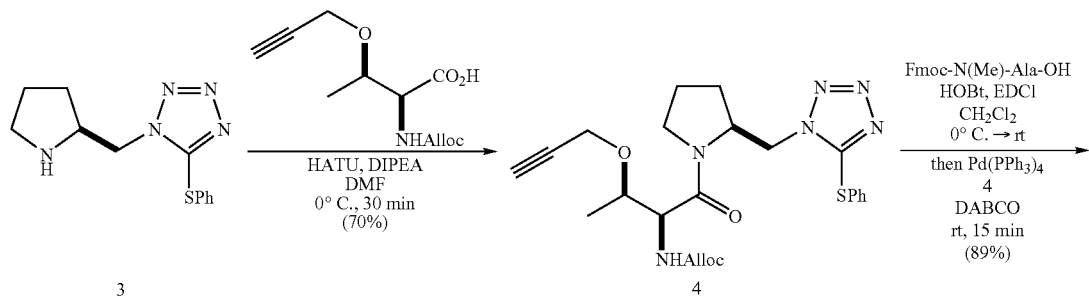
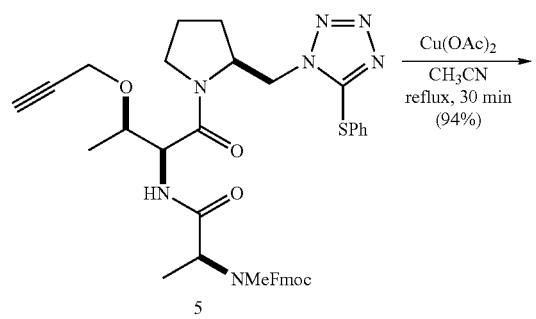

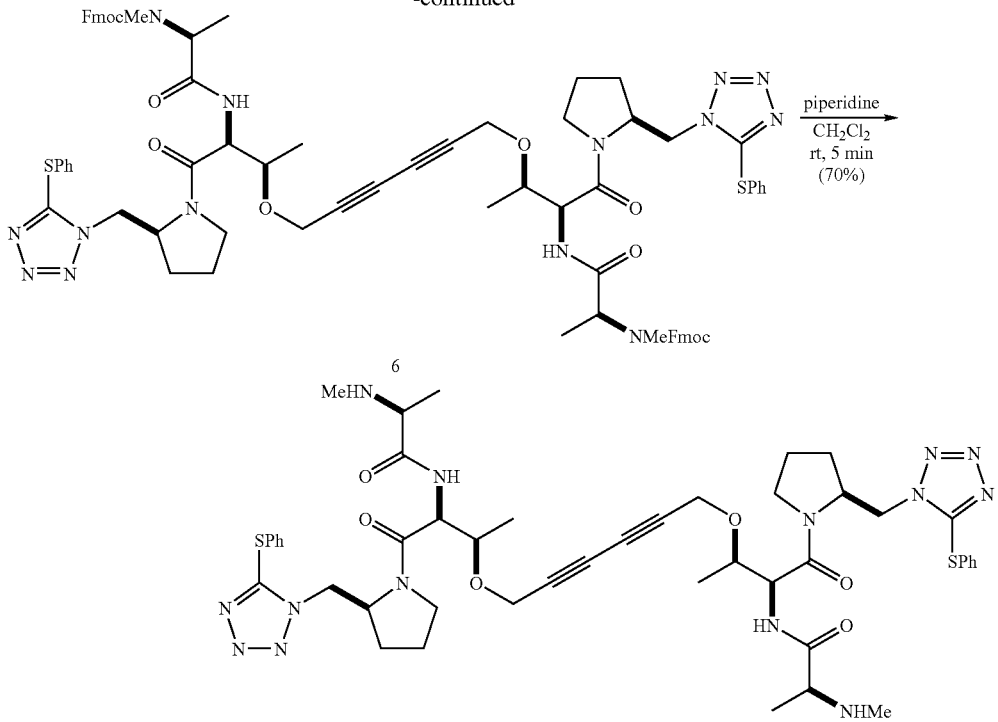

(S)-Boc-2-[5-(Toluene-4-sulfonyl)-tetrazol-1-ylmethyl]-pyrrolidine) (1)

A sealed tube was charged with p-toluenesulfonyl cyanide (5.0 g, 22.1 mmol) and (S)-Boc-2-azido methyl pyrrolidine[3] (4.0 g, 22.1 mmol). The mixture was stirred at 80° C. for 40 hrs. The crude product was purified on flash silica gel column with (Hexane:EtOAc=1:1) to furnish 1 (7.6 g, 84%) as colorless foam. $[\alpha]_D$ −11.7 (c 0.64, CHCl$_3$). $^1$H NMR (400 MHz, CD$_3$OD, −20° C., rotamers 6:4): δ 1.20 & 1.35 (s, 9H), 1.83 & 2.01 (m, 4H), 2.50 (s, 3H) 3.40 & 3.45 (m, 2H), 4.40 & 4.43 (m, 1H), 4.71 & 4.82 (m, 2H), 7.50 & 7.70 (d, J=8 Hz, 2H), 8.00 & 8.40 (d, J=8 Hz, 2H); $^{13}$C NMR (75 MHz, CDCl$_3$): δ 22.0, 23.7, 28.4, 46.5, 52.1, 56.1, 76.9, 80.6, 129.4, 134.4, 147.4, 154.4, 154.8, 155.5; IR (film): 2976, 1693, 1392, 815, 704 cm$^{-1}$; MS:(ESI) [M+1]$^+$408.2.

(S)-Boc-2-(5-Phenylsulfanyl-tetrazol-1'-ylmethyl)-pyrrolidine (2)

The mixture of 1 (6.0 g, 14.7 mmol), phenylthiol (6.5 g, 58.8 mmol) and K$_2$CO$_3$ (4.5 g, 41.1 mmol) in CH$_3$CN (74 ml) was stirred for 2 days at room temperature. The reaction mixture was filtered through a pad of Celite and then concentrated in vacuo. The crude was purified by silica gel column with (Hexane:EtOAc=1:1) as an eluant to give 2 (5.2 g, 97%) as an colorless oil. $[\alpha]_D$ −29.2 (c 1.34, CHCl$_3$). $^1$H NMR (400 MHz, CD$_3$OD, −20° C., rotamers 1:1): δ 1.30 & 1.42 (s, 9H), 1.73 & 2.01 (m, 4H) 3.40 & 3.45 (m, 13.2 Hz, 2H), 4.23 & 4.25 (m, 1H), 4.38 & 4.58 (m, 2H), 7.42 & 7.46 (m, 3H) 7.56 & 7.60 (m, 2H); $^{13}$C NMR (CDCl$_3$, 75 MHz): δ 21.2, 23.6, 28.5, 46.5, 49.7, 50.4, 56.7, 60.5, 80.7, 128.1, 129.9, 133.1, 153.5, 154.9; IR (film): 2975, 1693, 1391, 1167, 688 cm$^{-1}$; MS:(ESI) [M+1]$^+$361.2

(S)-2-(5-phenylsulfanyl-tetrazol-1-ylmethyl)-pyrrolidine (3)

2 (5.0 g, 13.8 mmol) was treated with 50% TFA in CH$_2$Cl$_2$ (69 ml) for 15 min at room temperature. The mixture was sequestered with sat.NaHCO$_3$ and extracted with CH$_2$Cl$_2$ (3×20 ml). The combined extraction were dried over Na$_2$SO$_4$, filtered and concentrated. The crude was purified over flash silica gel column with (CH$_2$Cl$_2$:MeOH:NH$_4$OH=20:0:9:1) as an eluant to furnish 3 (2.5 g, 69%). $[\alpha]_D$ +9.9 (c 1.14, CHCl$_3$). $^1$H NMR (400 MHz, CDCl$_3$): δ 1.45 (m, J=2 Hz, 8.4 Hz, 1H), 1.80 (m, 2H), 1.95 (m, 1H), 2.5 (bs, 1H), 2.99 (t, J=1.6 Hz, 2H), 3.60 (m, 1H), 4.20 (dd, J=8.0 Hz, 13.0 Hz, 1H), 4.30 (dd, J=8.0 Hz, 13.0 Hz 1H), 7.40 (m, 3H), 7.58 (m, 2H); $^{13}$C NMR (75 MHz, CDCl$_3$): δ 23.5, 28.6, 46.1, 47.8, 58.2, 127.2, 130.0, 130.2, 133.1, 153.4; IR (film): 3350, 2961, 2871, 1442, 1389, 746, 688 cm$^{-1}$; MS:(ESI) [M+1]$^+$262.2.

{1-[2-(5-Phenylsulfanyl-tetrazol-1-ylmethyl)-pyrrolidine-1-carbonyl]-2-ynyloxy-propyl}-carbamic acid allyl ester (4)

To a cold solution of 3 (2.5 g, 9.5 mmol) and N-Alloc-(propargyl) Threonine-(2S,3R) (2.7 g, 11.4 mmol) in DMF (48 ml) were added DIPEA (3.3 ml, 19.0 mmol) and HATU (5.4 g, 14.2 mmol). After stirring for 30 min at 0° C., the reaction mixture was diluted with Et$_2$O. To the mixture was added sat.NaHCO$_3$ and then separated. The aqueous phase was extracted with Et$_2$O (3×30 ml). The combined extraction were washed with 5% HCl (25 ml), H$_2$O (25 ml), sat-.NaHCO$_3$ (20 ml), and Brine (30 ml), and finally dried over MgSO$_4$, filtered and concentrated in vacuo. The crude was purified by silica gel column with (hexane:EtOAc=1:1) to afford 4 (3.2 g, 70%) as an oil. $[\alpha]_D$ −12.2 (c 1.30, CHCl$_3$) $^1$H NMR (400 MHz, CDCl$_3$): δ 1.22 (d, J=6 Hz, 3H), 1.75-1.90 (m, 4H), 2.50 (t, J=2.4 Hz, 1H), 3.70 (m, 2H) 4.00 (m, 1H), 4.20 (dq, J=5.6 Hz, 18.4 Hz, 2H), 4.31 (m, 2H), 4.50 (m, 1H), 4.55 (m, 2H), 4.62 (dd, J=4.2 Hz, 1H), 5.20 (d, J=9.6 Hz, 1H), 5.23 (d, J=10.2 Hz, 1H), 5.50 (d, J=8 Hz, 1H), 5.90 (m, 1H), 7.40 (m, 3H), 7.60 (m, 2H); $^{13}$C NMR (75 MHz, CDCl$_3$): δ 16.0, 24.3, 27.5, 47.9, 48.5, 56.5, 56.7, 66.1, 74.2, 74.9, 75.0, 79.8, 117.9, 127.6, 129.9, 130.0, 132.7, 133.3, 153.5, 156.4, 169.8; IR (film): 3292, 2979, 1715, 1644, 1513, 1442, 1073, 750, 688 cm$^{-1}$; MS:(ESI) [M+1]$^+$485.2.

{1-[2-(5-Phenylsulfanyl-tetrazol-1-ylmethyl)-pyrrolidine-1-carbonyl]-2-ynyloxy-propyl}-ethyl)-carbamic acid 9H-fluoren-9-ylmethyl ester (5)

To a solution of Fmoc-N(Me) L-Ala (6 g, 18.5 mmol) and HOBt (2.5 g, 18.5 mmol) in CH$_2$Cl$_2$ (60 ml) was added EDCI (3.5 g, 18.5 mmol) at 0° C. stirred for 1 hr and an additional hour at room temperature. To the reaction mixture was added Pd (PPh$_3$)$_4$ (3.6 g, 3.0 mmol), a solution of 4 (3 g, 6.2 mmol) in CH$_2$Cl$_2$ (30 ml) and DABCO (3.7 g, 31 mmol) at room temperature followed by stirred for 15 min. The reaction mixture was concentrated in vacuo and purified by silica gel column with (hexane:EtOAc=1:1) to furnish 5 (3.8 g, 89%) as pale yellow foam. [α]$_D$ –31.9 (c 1.56, CHCl$_3$). $^1$H NMR (400 MHz, CDCl$_3$): δ 1.20 (d, J=3.6 Hz, 3H), 1.41 (d, J=4.2 Hz, 3H), 1.75-1.98 (bm, 4H), 2.50 (bs, 1H), 2.95 (s, 3H), 3.60 (bm, 1H), 3.70 (bm, 1H), 4.01 (bm, 1H), 4.10 (dq J=5.6 Hz, 18.1 Hz, 2H), 4.20 (bm, 1H), 4.25 (bm, 1H), 4.28 (bm, 2H) 4.32 (bm, 1H), 4.40 (bm, 2H), 4.59 (dd, J=4.2, 8.0 Hz, 1H), 6.81 (bd, 1H), 7.28 (bm, 2H), 7.34 (bm, 5H), 7.52 (br m, 4H), 7.72 (d, J=7.6 Hz, m, 2H); $^{13}$C NMR (75 MHz, CDCl$_3$): δ 16.1, 24.3, 27.5, 47.4, 48.5, 55.3, 56.4, 68.2, 74.0, 75.0, 79.8, 120.1, 125.2, 125.3, 127.2, 127.6, 127.9, 128.6, 129.9, 130.1, 132.2, 132.4, 133.3, 141.5, 153.5, 169.3, 171.4; IR (film): 3297, 2978, 1693, 1650, 1442, 1400, 1312, 1157, 10948, 758, 742 cm$^{-1}$; MS:(ESI) [M+1]$^+$ 708.2

{1-[2-Bis-(5-Phenylsulfanyl-tetrazol-1-ylmethyl)-pyrrolidine-1-carbonyl]-2-ynyloxy-propyl}-ethyl)-carbamic acid 9H-fluoren-9-ylmethyl ester (6)

A mixture of 5 (3.5 g, 4.9 mmol) and Cu(OAc)$_2$ (6.2 g, 34.3 mmol) in CH$_3$CN was refluxed for 30 min. The organic solvent was stripped off and the Cu(II) salts were removed by filtering over a short pad of silica gel eluting with (CH$_2$Cl$_2$/MeOH 9:1) to give a crude, which was completely dried off to furnish crude 6 (3.3 g, 94%) as pale yellow foam. A small portion of the crude was purified for spectral analysis. [α]$_D$ –13.8 (c 1.41, CHCl$_3$). $^1$H NMR (400 MHz, CDCl$_3$): δ 1.14 (d, J=6 Hz, 6H), 1.34 (d, J=7.2 Hz, 6H), 1.74-1.98 (bm, 8H), 2.84 (s, 6H), 3.60 (bm, 4H), 3.87 (bm, 2H), 4.09 (ABq, J=16.8 Hz, 4H), 4.20 (bm, 2H), 4.24 (m, 2H), 4.31 (bm, 4H), 4.36 (m, 4H), 4.60 (dd, J=4.2 Hz, 2H), 4.69 (dd, J=4, 8.8 Hz, 2H), 6.80 (bm, 2H), 7.28 (bm, 4H), 7.34 (bm, 10H), 7.52 (bm, 8H), 7.72 (d, J=7.6 Hz, m, 4H); $^{13}$C NMR (75 MHz, CDCl$_3$): δ 16.3, 24.3, 27.5, 47.4, 48.5, 55.3, 56.4, 68.2, 74.0, 75.0, 79.8, 120.1, 125.2, 125.3, 127.2, 127.6, 127.9, 128.6, 129.9, 130.1, 132.2, 132.4, 133.3, 141.5, 153.5, 169.3, 171.4; IR (film): 2920, 2850, 1687, 1643, 1441, 1311, 1155, 1083, 741 cm$^{-1}$; MS: (ESI) [M+1]$^+$1412.2

Bis-2-Methylamino-N-(1-{1-[2-(5-phenylsulfanyl-tetrazol-1-ylmethyl)-pyrrolidine-1-carbonyl]-2-ynyloxy-propyl}-propionamide (7)

A solution of 6 (3 g, 2.1 mmol) was treated with 20% CH$_2$Cl$_2$-piperidine (21 ml) for 5 min. The mixture was concentrated in vacuo and then purified by silica gel column with (CH$_2$Cl$_2$:MeOH:NH$_4$OH=8:2:0.5) to furnish 7 (1.4 g 70%) as gummy foam. [α]$_D$ –7.4 (c 0.23, CHCl$_3$). $^1$H NMR (400 MHz, CDCl$_3$): δ 1.19 (d, J=6.4 Hz, 6H), 1.28 (d, J=7.2 Hz 6H), 1.78 (m, 4H), 1.90 (m, 4H), 2.50 (s, 6H), 3.05 (q, J=7.2 Hz, 2H), 3.60 (bm, 2H), 3.70 (m, 2H), 4.01 (m, 2H), 4.20 (ABq, J=18.4 Hz, 4H), 4.43 (dd, J=4.0 Hz & 13.6 Hz, 2H), 4.50 (m, 2H), 4.70 (dd, J=4 Hz & 13.6 Hz, 2H), 4.75 (dd, J=4, 8.8 Hz, 2H), 7.40 (m, 6H), 7.60 (m, 4H), 7.82 (d, J=8.4 Hz, 2H); $^{13}$C NMR (75 MHz, CDCl$_3$): δ 16.2, 19.6, 22.8, 24.4, 27.5, 31.8, 35.2, 47.8, 48.5, 54.6, 56.3, 56.9, 60.4, 70.4, 74.4, 76.1, 76.8, 127.7, 129.9, 130.0, 133.3, 153.6, 169.5, 175.4; IR (film): 3339, 2975, 1644, 1513, 1428, 1086, 751, 667 cm$^{-1}$; MS:(ESI) [M+1]$^+$ 969.4

REFERENCES

1. Lumma, W. C.; Wohl, Ronald A. *Eur. Pat. Appl.* 1985, EP 134424 A1
2. Bejjani, J; Chemla, F; Audouin, M. *J. Org. Chem.*, 2003, 68, 9747-9752.
3. Black, Julian; Brown, Alan D; Erizabet C L; Smith, J D; Mckelloy, A B. 2000 JP 2000063380
4. Dininno, F; Guthikonda, R N.; Schmitt, S M. 1994 U.S. Pat. No. 5,292,879 A Scheme 1

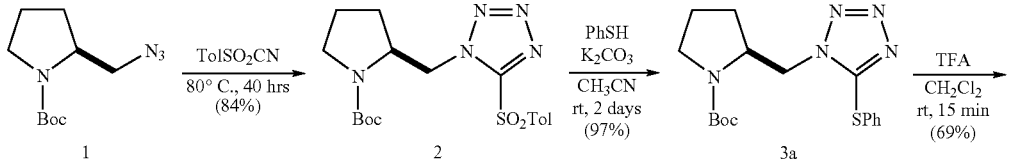

-continued
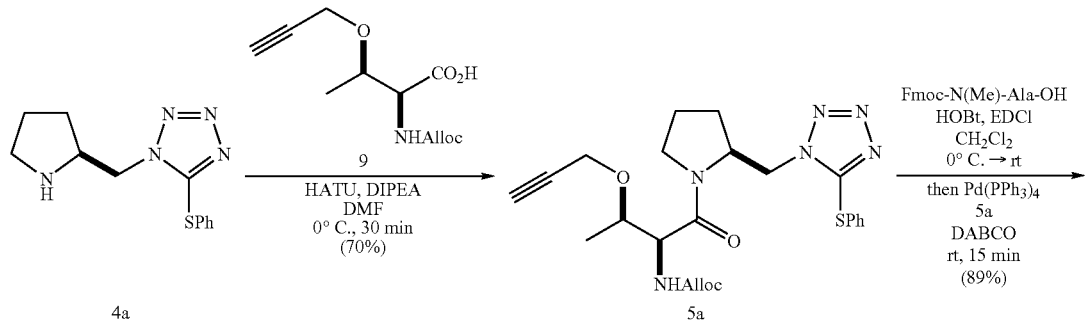
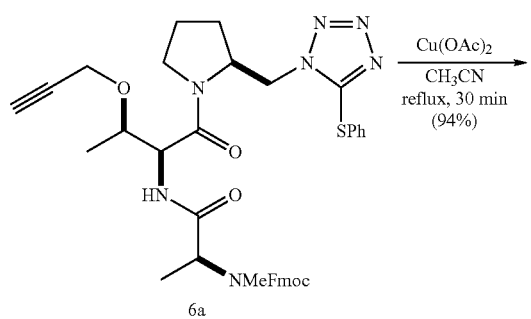
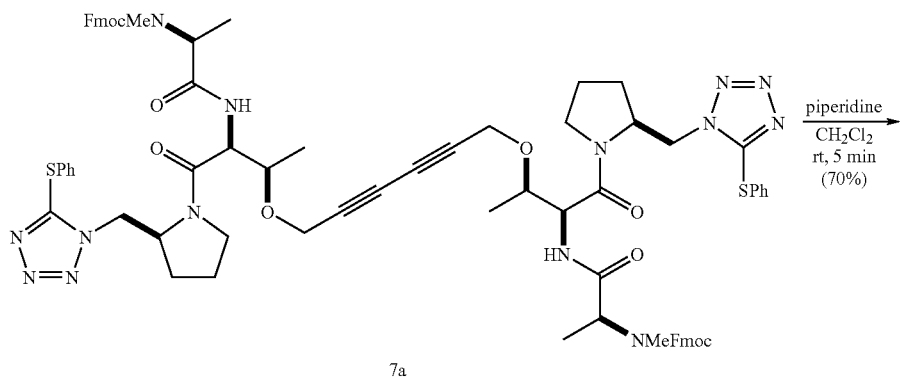
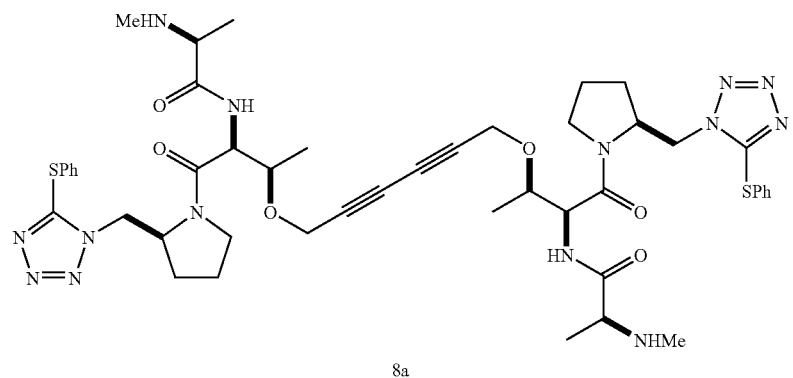

(S)-Boc-2-[5-(Toluene-4-sulfonyl)-tetrazol-1-ylmethyl]-pyrrolidine) (2)

A sealed tube was charged with p-toluenesulfonyl cyanide (5.0 g, 22.1 mmol) and (S)-Boc-2-azido methylpyrrolidine (1) [Black, J.; Brown, A. D.; Erizabet C. L.; Smith, J. D.; Mckelloy, A. B. 2000 JP2000063380] (4.0 g, 22.1 mmol). The mixture was stirred at 80° C. for 40 hrs. The crude product was purified on flash silica gel column with (Hexane: EtOAc=1:1) to furnish 2 (7.6 g, 84%) as colorless foam. $[\alpha]_D$ −11.7 (c 0.64, CHCl$_3$). $^1$H NMR (400 MHz, CD$_3$OD, −20° C., rotamers 6:4): δ 1.20 & 1.35 (s, 9H), 1.83 & 2.01 (m, 4H), 2.50 (s, 3H) 3.40 & 3.45 (m, 2H), 4.40 & 4.43 (m, 1H), 4.71 & 4.82 (m, 2H), 7.50 & 7.70 (d, J=8 Hz, 2H), 8.00 & 8.40 (d, J=8 Hz, 2H); $^{13}$C NMR (75 MHz, CDCl$_3$): δ 22.0, 23.7, 28.4, 46.5, 52.1, 56.1, 76.9, 80.6, 129.4, 134.4, 147.4, 154.4, 154.8, 155.5; IR (film): 2976, 1693, 1392, 815, 704 cm$^{-1}$; MS:(ESI) [M+1]$^+$408.2.

(S)-Boc-2-(5-Phenylsulfanyl-tetrazol-1'-ylmethyl)-pyrrolidine (3a)

The mixture of 2 (6.0 g, 14.7 mmol), phenylthiol (6.5 g, 58.8 mmol) and K$_2$CO$_3$ (4.5 g, 41.1 mmol) in CH$_3$CN (74 ml) was stirred for 2 days at room temperature. The reaction mixture was filtered through a pad of Celite and then concentrated in vacuo. The crude was purified by silica gel column with (Hexane:EtOAc=1:1) as an eluant to give 3 (5.2 g, 97%) as an colorless oil. $[\alpha]_D$ −29.2 (c 1.34, CHCl$_3$). $^1$H NMR (400 MHz, CD$_3$OD, −20° C., rotamers 1:1): δ 1.30 & 1.42 (s, 9H), 1.73 & 2.01 (m, 4H) 3.40 & 3.45 (m, 13.2 Hz, 2H), 4.23 & 4.25 (m, 1H), 4.38 & 4.58 (m, 2H), 7.42 & 7.46 (m, 3H) 7.56 & 7.60 (m, 2H); $^{13}$C NMR (CDCl$_3$, 75 MHz): δ 21.2, 23.6, 28.5, 46.5, 49.7, 50.4, 56.7, 60.5, 80.7, 128.1, 129.9, 133.1, 153.5, 154.9; IR (film): 2975, 1693, 1391, 1167, 688 cm$^{-1}$; MS:(ESI) [M+1]$^+$361.2

(S)-2-(5-phenylsulfanyl-tetrazol-1-ylmethyl)-pyrrolidine (4a)

3a (5.0 g, 13.8 mmol) was treated with 50% TFA in CH$_2$Cl$_2$ (69 ml) for 15 min at room temperature. The mixture was sequestered with sat.NaHCO$_3$ and extracted with CH$_2$Cl$_2$ (3×20 ml). The combined extraction were dried over Na$_2$SO$_4$, filtered and concentrated. The crude was purified over flash silica gel column with (CH$_2$Cl$_2$:MeOH:NH$_4$OH=20:0:9:1) as an eluant to furnish 4a (2.5 g, 69%). $[\alpha]_D$ +9.9 (c 1.14, CHCl$_3$). $^1$H NMR (400 MHz, CDCl$_3$): δ 1.45 (m, J=2, 8.4 Hz, 1H), 1.80 (m, 2H), 1.95 (m, 1H), 2.5 (bs, 1H), 2.99 (t, J=1.6 Hz, 2H), 3.60 (m, 1H), 4.20 (dd, J=8.0, 13.0 Hz, 1H), 4.30 (dd, J=8.0, 13.0 Hz 1H), 7.40 (m, 3H), 7.58 (m, 2H); $^{13}$C NMR (75 MHz, CDCl$_3$): δ 23.5, 28.6, 46.1, 47.8, 58.2, 127.2, 130.0, 130.2, 133.1, 153.4; IR (film): 3350, 2961, 2871, 1442, 1389, 746, 688 cm$^{-1}$; MS:(ESI) [M+1]$^+$262.2.

{1-[2-(5-Phenylsulfanyl-tetrazol-1-ylmethyl)-pyrrolidine-1-carbonyl]-2-ynyloxy-propyl}-carbamic acid allyl ester (5a)

To a cold solution of 4a (2.5 g, 9.5 mmol) and 9 (2.7 g, 11.4 mmol) in DMF (48 ml) were added DIPEA (3.3 ml, 19.0 mmol) and HATU (5.4 g, 14.2 mmol). After stirring for 30 min at 0° C., the reaction mixture was diluted with Et$_2$O. To the mixture was added sat.NaHCO$_3$ and then separated. The aqueous phase was extracted with Et$_2$O (3×30 ml). The combined extraction were washed with 5% HCl (25 ml), H$_2$O (25 ml), sat.NaHCO$_3$ (20 ml), and Brine (30 ml), and finally dried over MgSO$_4$, filtered and concentrated in vacuo. The crude was purified by silica gel column with (hexane:EtOAc=1:1) to afford 5a (3.2 g, 70%) as an oil. $[\alpha]_D$ −12.2 (c 1.30, CHCl$_3$) $^1$H NMR (400 MHz, CDCl$_3$): δ 1.22 (d, J=6 Hz, 3H), 1.75-1.90 (m, 4H), 2.50 (t, J=2.4 Hz, 1H), 3.70 (m, 2H) 4.00 (m, 1H), 4.20 (dq, J=5.6, 18.4 Hz, 2H), 4.31 (m, 2H), 4.50 (m, 1H), 4.55 (m, 2H), 4.62 (dd, J=4.2 Hz, 1H), 5.20 (d, J=9.6 Hz, 1H), 5.23 (d, J=10.2 Hz, 1H), 5.50 (d, J=8 Hz, 1H), 5.90 (m, 1H), 7.40 (m, 3H), 7.60 (m, 2H); $^{13}$C NMR (75 MHz, CDCl$_3$): δ 16.0, 24.3, 27.5, 47.9, 48.5, 56.5, 56.7, 66.1, 74.2, 74.9, 75.0, 79.8, 117.9, 127.6, 129.9, 130.0, 132.7, 133.3, 153.5, 156.4, 169.8; IR (film): 3292, 2979, 1715, 1644, 1513, 1442, 1073, 750, 688 cm$^{-1}$; MS:(ESI) [M+1]$^+$485.2.

{1-[2-(5-Phenylsulfanyl-tetrazol-1-ylmethyl)-pyrrolidine-1-carbonyl]-2-ynyloxy-propyl}-ethyl)-carbamic acid 9H-fluoren-9-ylmethyl ester (6a)

To a solution of Fmoc-N(Me) L-Ala (6 g, 18.5 mmol) and HOBt (2.5 g, 18.5 mmol) in CH$_2$Cl$_2$ (60 ml) was added EDCI (3.5 g, 18.5 mmol) at 0° C. stirred for 1 hr and an additional hour at room temperature. To the reaction mixture was added Pd(PPh$_3$)$_4$ (3.6 g, 3.0 mmol), a solution of 5a (3 g, 6.2 mmol) in CH$_2$Cl$_2$ (30 ml) and DABCO (3.7 g, 31 mmol) at room temperature followed by stirred for 15 min. The reaction mixture was concentrated in vacuo and purified by silica gel column with (hexane:EtOAc=1:1) to furnish 6a (3.8 g, 89%) as pale yellow foam. $[\alpha]_D$ −31.9 (c 1.56, CHCl$_3$). $^1$H NMR (400 MHz, CDCl$_3$): δ 1.20 (d, J=3.6 Hz, 3H), 1.41 (d, J=4.2 Hz, 3H), 1.75-1.98 (bm, 4H), 2.50 (bs, 1H), 2.95 (s, 3H), 3.60 (bm, 1H), 3.70 (bm, 1H), 4.01 (bm, 1H), 4.10 (dq J=5.6 Hz, 18.1 Hz, 2H), 4.20 (bm, 1H), 4.25 (bm, 1H), 4.28 (bm, 2H) 4.32 (bm, 1H), 4.40 (bm, 2H), 4.59 (dd, J=4.2, 8.0 Hz, 1H), 6.81 (bd, 1H), 7.28 (bm, 2H), 7.34 (bm, 5H), 7.52 (br m, 4H), 7.72 (d, J=7.6 Hz, m, 2H); $^{13}$C NMR (75 MHz, CDCl$_3$): δ 16.1, 24.3, 27.5, 47.4, 48.5, 55.3, 56.4, 68.2, 74.0, 75.0, 79.8, 120.1, 125.2, 125.3, 127.2, 127.6, 127.9, 128.6, 129.9, 130.1, 132.2, 132.4, 133.3, 141.5, 153.5, 169.3, 171.4; IR (film): 3297, 2978, 1693, 1650, 1442, 1400, 1312, 1157, 10953, 758, 742 cm$^{-1}$; MS:(ESI) [M+1]$^+$ 708.2

{1-[2-Bis-(5-Phenylsulfanyl-tetrazol-1-ylmethyl)-pyrrolidine-1-carbonyl]-2-ynyloxy-propyl}-ethyl)-carbamic acid 9H-fluoren-9-ylmethyl ester (7a)

A mixture of 6a (3.5 g, 4.9 mmol) and Cu(OAc)$_2$ (6.2 g, 34.3 mmol) in CH$_3$CN was refluxed for 30 min. The organic solvent was stripped off and the resultant residue redissolved in CH$_2$Cl$_2$ and the Cu(II) salts were removed by filtering over a short pad of silica gel eluting with (CH$_2$Cl$_2$:MeOH=9:1) to give material, which was completely dried off to furnish crude of 7a (3.3 g, 94%) as a mixture of desired product (major) and partially deprotected material. A small portion of the crude was purified for spectral analysis. $[\alpha]_D$ −13.8 (c 1.41, CHCl$_3$). $^1$H NMR (400 MHz, CDCl$_3$): δ 1.14 (d, J=6 Hz, 6H), 1.34 (d, J=7.2 Hz, 6H), 1.74-1.98 (bm, 8H), 2.84 (s, 6H), 3.60 (bm, 4H), 3.87 (bm, 2H), 4.09 (ABq, J=16.8 Hz, 4H), 4.20 (bm, 2H), 4.24 (m, 2H), 4.31 (bm, 4H), 4.36 (m, 4H), 4.60 (dd, J=4.2 Hz, 2H), 4.69 (dd, J=4, 8.8 Hz, 2H), 6.80 (bm, 2H), 7.28 (bm, 4H), 7.34 (bm, 10H), 7.52 (bm, 8H), 7.72 (d, J=7.6 Hz, m, 4H); $^{13}$C NMR (75 MHz, CDCl$_3$): δ 16.3, 24.3, 27.5, 47.4, 48.5, 55.3, 56.4, 68.2, 74.0, 75.0, 79.8, 120.1, 125.2, 125.3, 127.2, 127.6, 127.9, 128.6, 129.9, 130.1, 132.2, 132.4, 133.3, 141.5, 153.5, 169.3, 171.4; IR (film): 2920, 2850, 1687, 1643, 1441, 1311, 1155, 1083, 741 cm$^{-1}$; MS:(ESI) [M+1]$^+$1412.2

Bis-2-Methylamino-N-(1-{1-[2-(5-phenylsulfanyl-tetrazol-1-ylmethyl)-pyrrolidine-1-carbonyl]-2-ynyloxy-propyl}-propionamide (8a)

A solution of 7a (3 g, 2.1 mmol) was treated with 20% CH$_2$Cl$_2$-piperidine (21 ml) for 5 min. The mixture was concentrated in vacuo and then purified by silica gel column with (CH$_2$Cl$_2$:MeOH:NH$_4$OH=8:2:0.5) to furnish 8a (1.4 g 70%) as gummy foam. [α]$_D$ –7.4 (c 0.23, CHCl$_3$). $^1$H NMR (400 MHz, CDCl$_3$): δ 1.19 (d, J=6.4 Hz, 6H), 1.28 (d, J=7.2 Hz 6H), 1.78 (m, 4H), 1.90 (m, 4H), 2.50 (s, 6H), 3.05 (q, J=7.2 Hz, 2H), 3.60 (bm, 2H), 3.70 (m, 2H), 4.01 (m, 2H), 4.20 (ABq, J=18.4 Hz, 4H), 4.43 (dd, J=4.0, 13.6 Hz, 2H), 4.50 (m, 2H), 4.70 (dd, J=4, 13.6 Hz, 2H), 4.75 (dd, J=4, 8.8 Hz, 2H), 7.40 (m, 6H), 7.60 (m, 4H), 7.82 (d, J=8.4 Hz, 2H); $^{13}$C NMR (75 MHz, CDCl$_3$): δ 16.2, 19.6, 22.8, 24.4, 27.5, 31.8, 35.2, 47.8, 48.5, 54.6, 56.3, 56.9, 60.4, 70.4, 74.4, 76.1, 76.8, 127.7, 129.9, 130.0, 133.3, 153.6, 169.5, 175.4; IR (film): 3339, 2975, 1644, 1513, 1428, 1086, 751, 667 cm$^{-1}$; MS:(ESI) [M+1]$^+$ 969.4.

Scheme 2

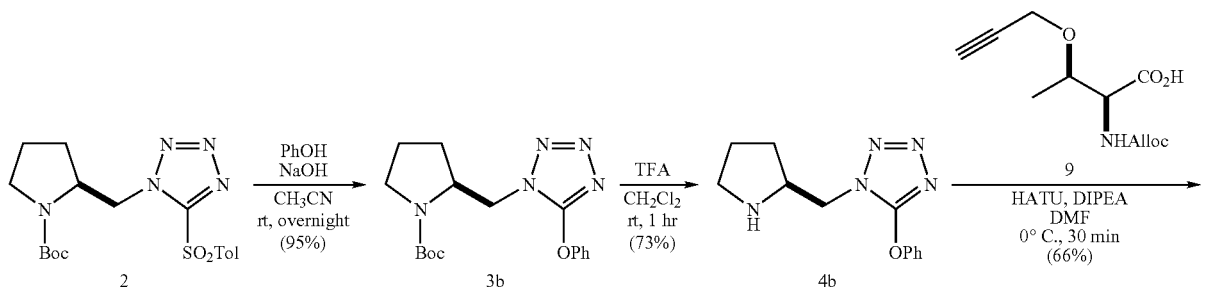

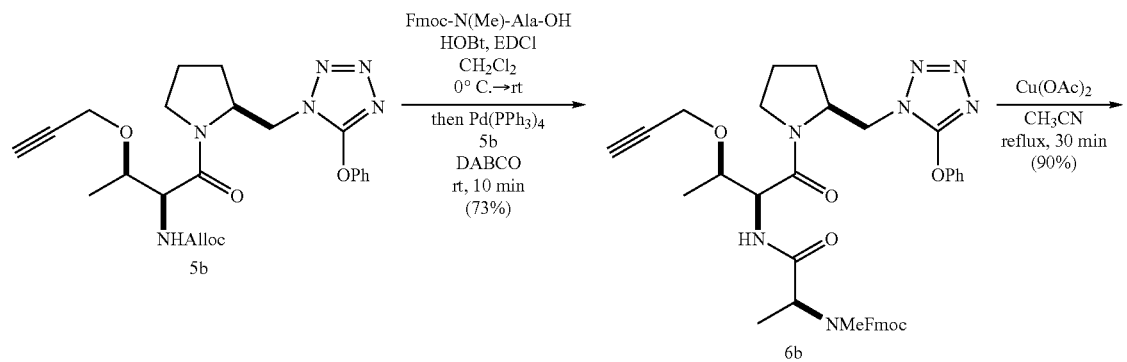

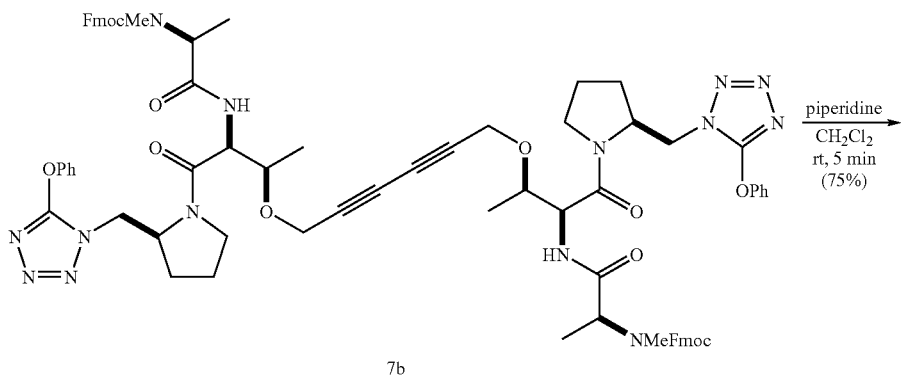

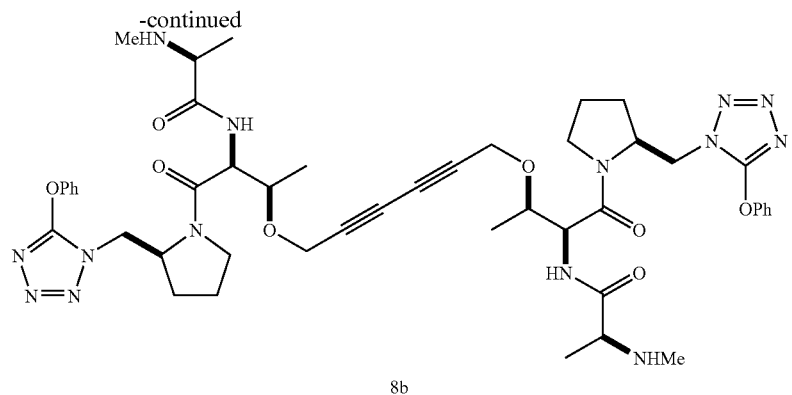
8b
2-Methylamino-N-{2-(6-{1-methyl-2-(2-methylamino-propionylamino)-3-oxo-3-[2-(5-phenoxy-tetrazol-1-ylmethyl)-pyrrolidin-1-yl]-propoxy}-hexa-2,4-diynyloxy)-1-[2-(5-phenoxy-tetrazol-1-ylmethyl)-pyrrolidine-1-carbonyl]-propyl}-propionamide (8b)
8b was synthesized according to scheme 2.
$^1$H NMR (400 MHz, CDCl$_3$): δ 1.20 (d, J=6.4 Hz, 6H), 1.29 (d, J=6.8 Hz, 6H), 1.65-2.15 (m, 8H), 2.50 (s, 6H), 3.05 (q, J=6.8 Hz, 2H), 3.59 (m, 2H), 3.75 (m, 2H), 4.03 (m, 2H), 4.20 (ABq, J=11.6, 16.4 Hz, 4H), 4.39 (m, 2H), 4.60 (m 4H), 4.67 (dd, J=4.4 Hz, 8.4 Hz, 2H), 7.20 (m, 2H), 7.40 (m, 8H), 7.82 (d, J=8.4 Hz, 2H); MS:(ESI) [M+1]$^+$ 937.5
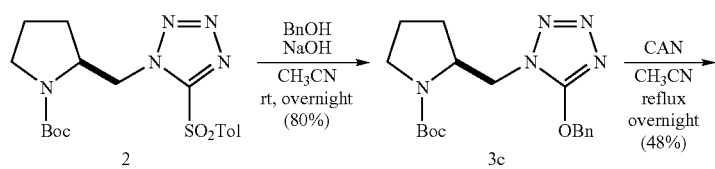
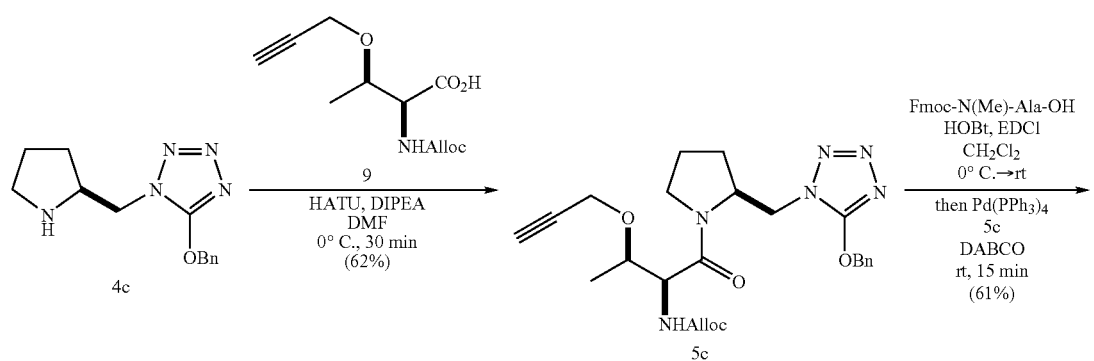

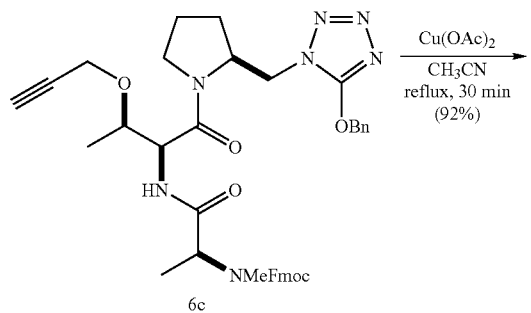
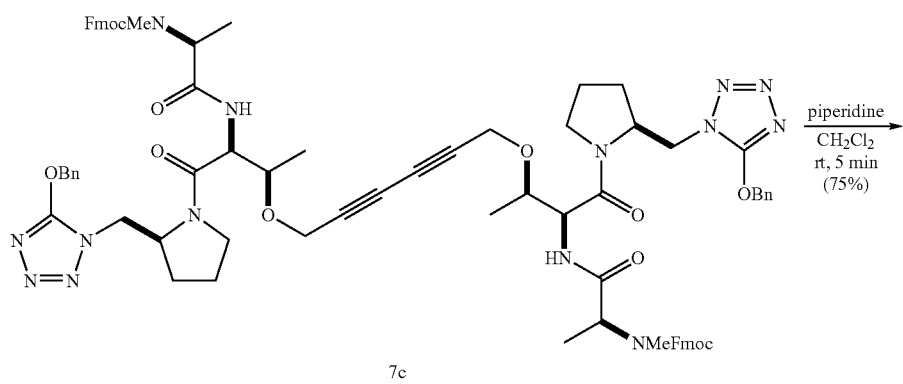
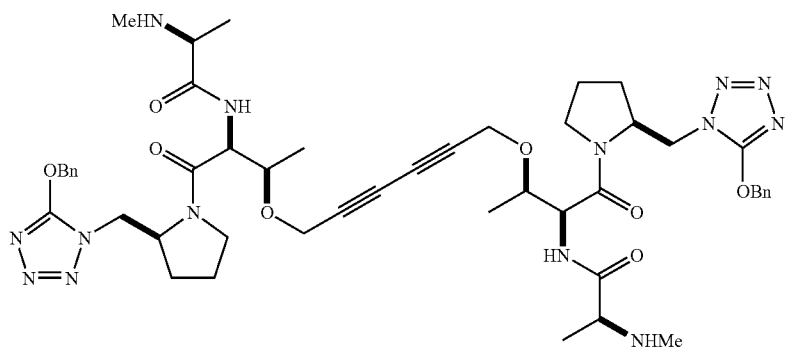

N-(1-[2-(5-benzyloxy-tetrazol-1-ylmethyl)-pyrrolidine-1-carbonyl]-2-{6-[3-[2-(5-benzyloxy-tetrazol-1-ylmethyl)-pyrrolidin-1-yl]-1-methyl-2-(2-methylamino-propionylamino)-3-oxo-propoxy]-hexa-2,4-diynyloxy}-propyl)-2-methylamino-propionamide (8c)
8c was prepared according to scheme 3.
$^1$H NMR (400 MHz, CDCl$_3$): δ 1.20 (d, J=6.4 Hz, 6H), 1.29 (d, J=6.8 Hz, 6H), 1.60 (m, 4H), 1.81 (m, 4H), 2.50 (s, 6H), 3.05 (q, J=6.8 Hz, 2H), 3.51 (m, 4H), 3.68 (m, 4H), 4.03 (m, 2H), 4.16 (m, 6H), 4.36 (dd, J=4.4, 14.4 Hz 2H), 4.47 (m, 2H), 4.67 (dd, J=4.4, 8.4 Hz, 2H), 5.52 (ABq, J=11.6, 16.4 Hz, 4H), 7.37 (m, 6H), 7.48 (m, 4H), 7.82 (d, J=8.4 Hz, 2H); MS:(ESI) [M/2]$^+$ 482.4.
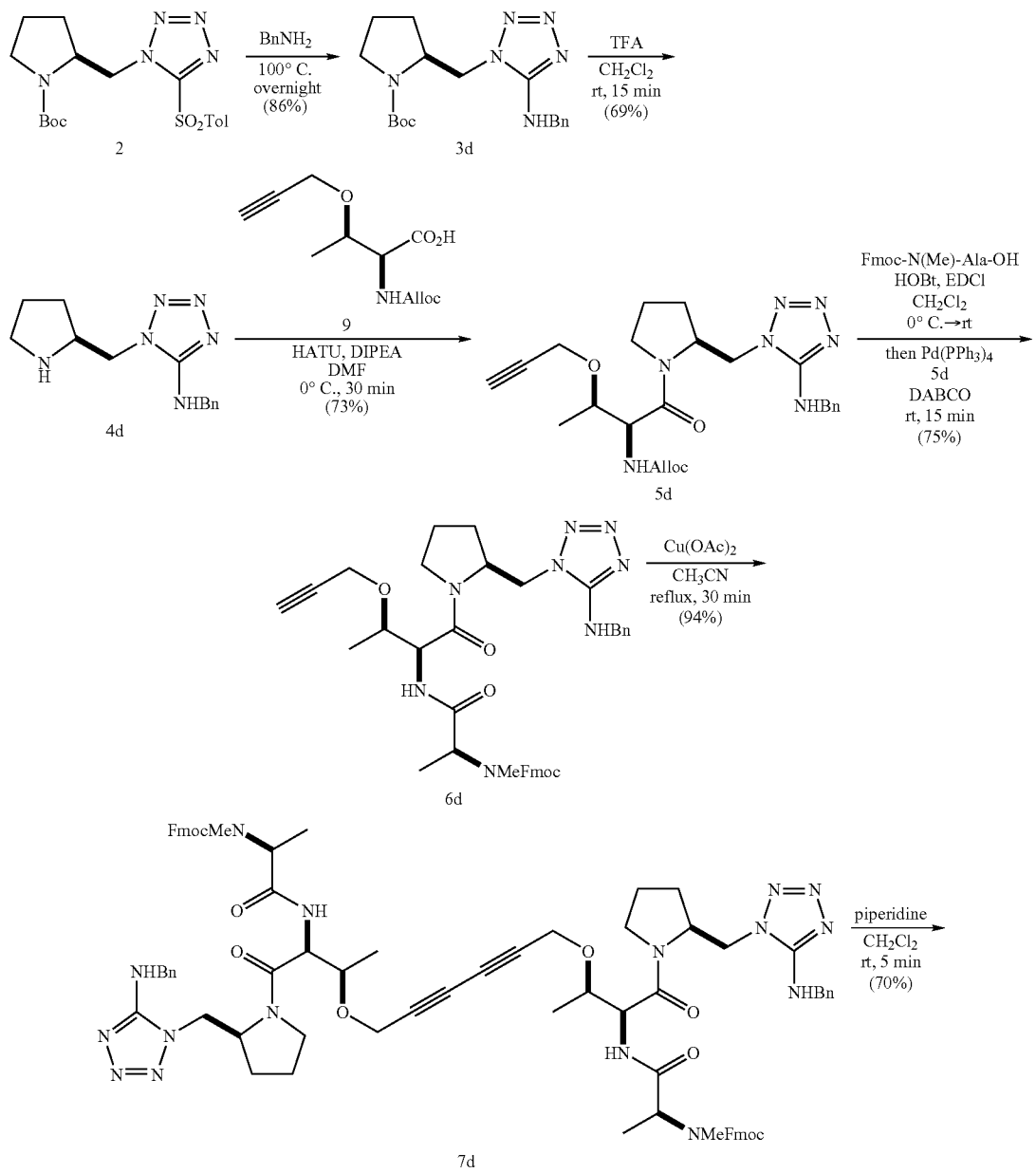

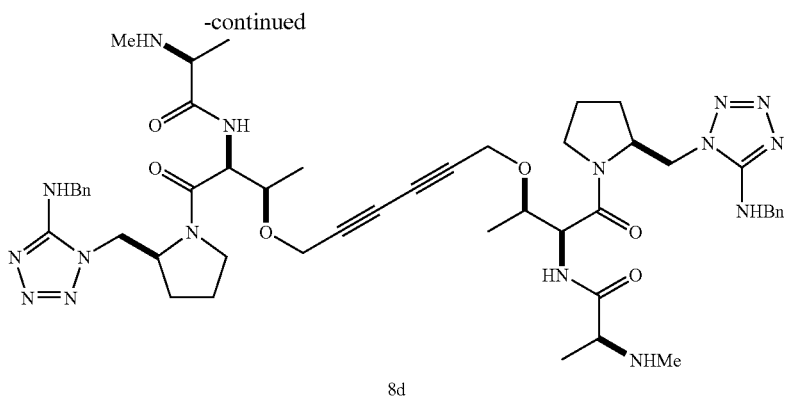
8d
N-(1-[2-(5-benzylamino-tetrazol-1-ylmethyl)-pyrrolidine-1-carbonyl]-2-{6-[3-[2-(5-benzylamino-tetrazol-1-ylmethyl)-pyrrolidin-1-yl]-1-methyl-2-(2-methylamino-propionylamino)-3-oxo-propoxy]-hexa-2,4-diynyloxy}-propyl)-2-methylamino-propionamide (8d)
8d was synthesized according to scheme 4.
$^1$H NMR (400 MHz, CDCl$_3$): δ 1.15 (d, J=6.4 Hz, 6H), 1.29 (d, J=6.8 Hz, 6H), 1.85-2.20 (m, 8H), 2.50 (s, 6H), 3.05 (q, J=6.8 Hz, 2H), 3.60 (bm, 2H), 3.79 (m, 2H), 3.96-4.40 (m, 14H), 4.64 (dd, J=8.8, 14.8 Hz, 2H), 4.73 (dd, J=3.2, 8.8 Hz, 2H), 6.81 (t, J=6.0 Hz, 2H), 7.22 (m, 6H), 7.39 (m, 4H), 7.84 (d, J=8.8 Hz, 2H); MS: (ESI) [M/2+Na]$^+$ 485.4.
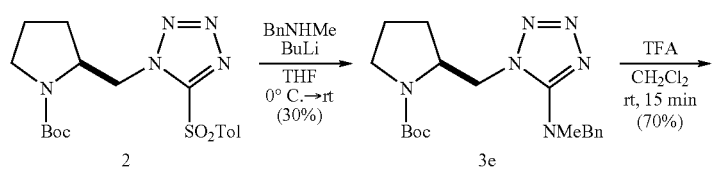
Scheme 5
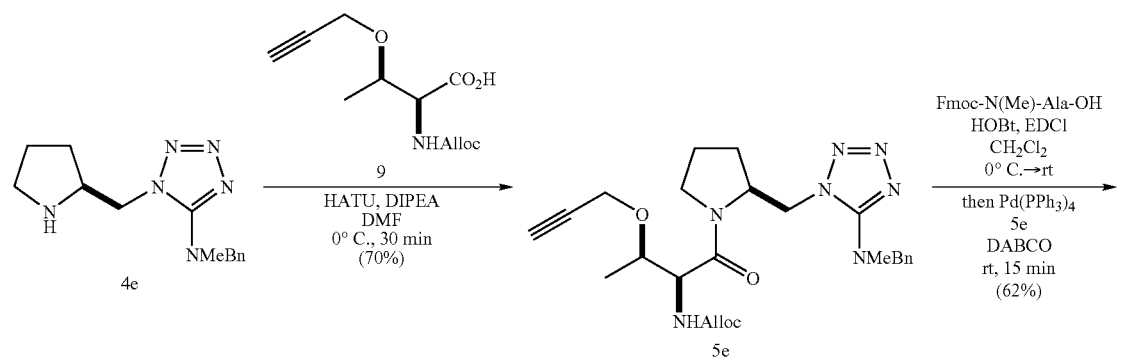

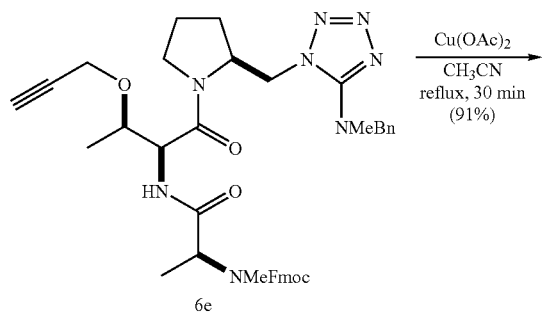
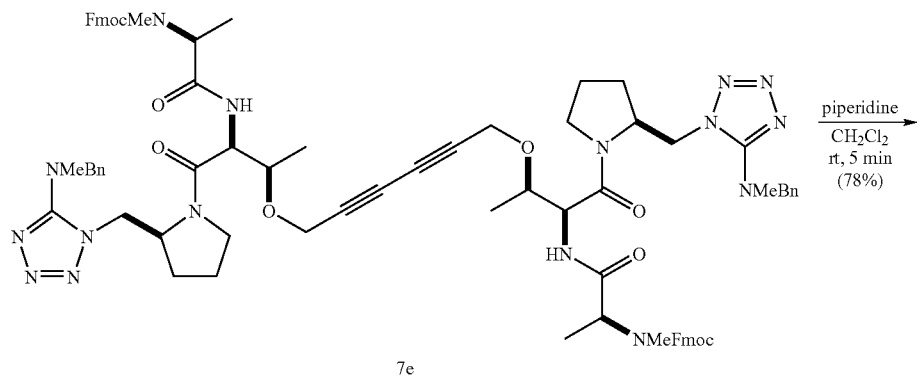
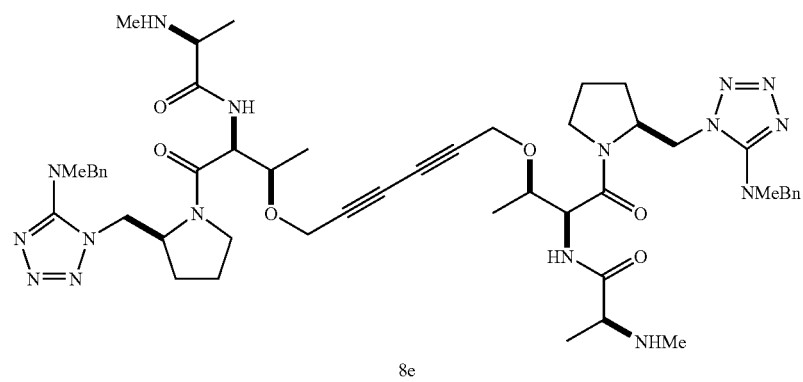

Bis-N-(1-{2-[5-Benzylmethylamino]-tetrazol-1-ylm-ethyl}-pyrrolidine-1-carbonyl)-2-prop-2-ynyloxy-propyl)-2-methylamino-propioamide (8e)
8e was synthesized according to scheme 5.
¹H NMR (400 MHz, CDCl₃): δ 1.15 (d, J=6.4 Hz, 6H), 1.29 (d, J=6.8 Hz, 6H), 1.79-2.15 (m, 8H), 2.50 (s, 6H), 3.05 (q, J=6.8 Hz, 2H), 3.15 (s, 6H), 3.60 (bm, 4H), 3.99 (m, 2H), 4.10 (m, 6H), 4.41 (m, 2H), 4.51 (m, 4H), 4.71 (m 4H), 7.25 (m, 10H), 7.80 (d, J=8.8 Hz, 2H); MS:(ESI) [M+Na]⁺ 1013.5.
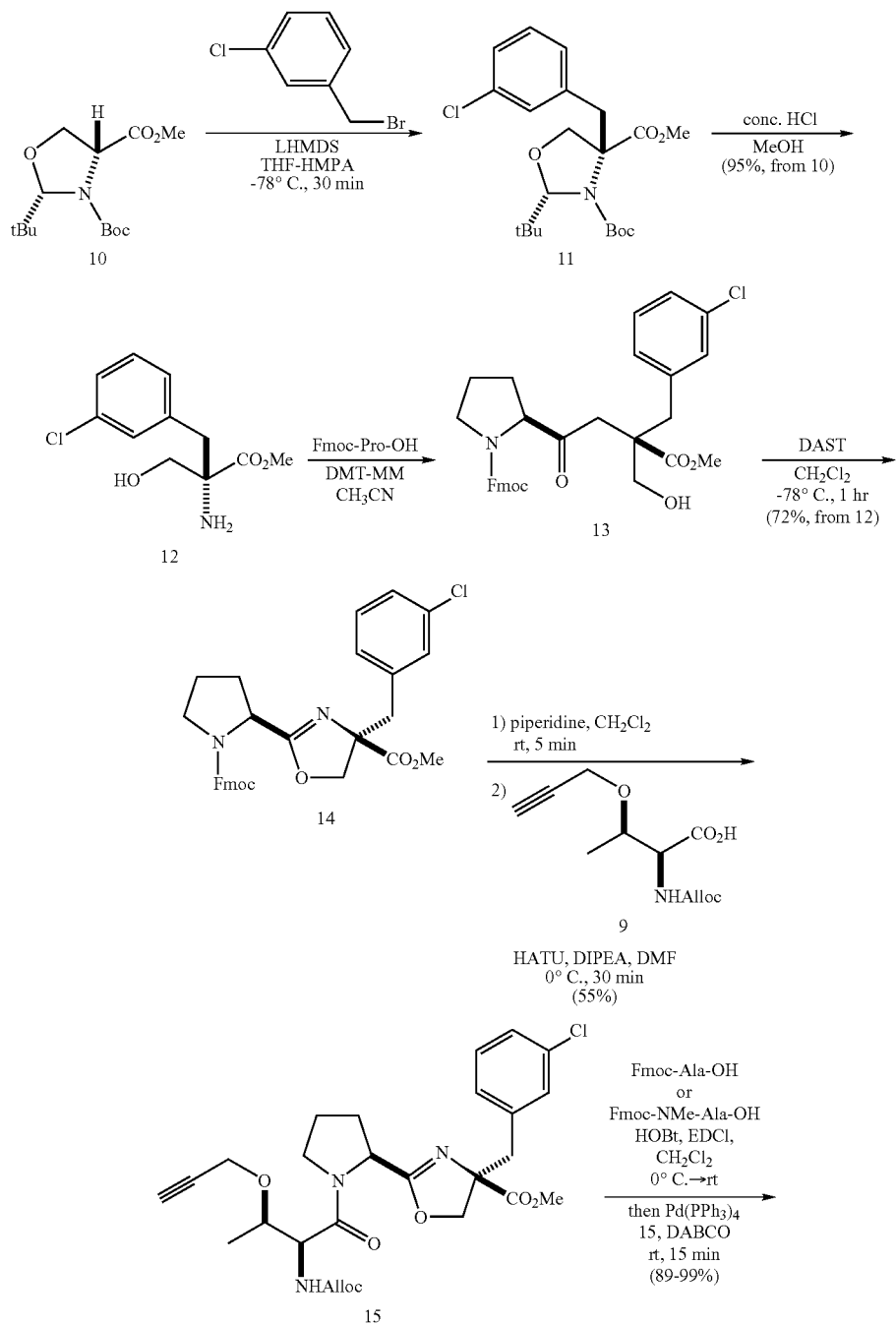

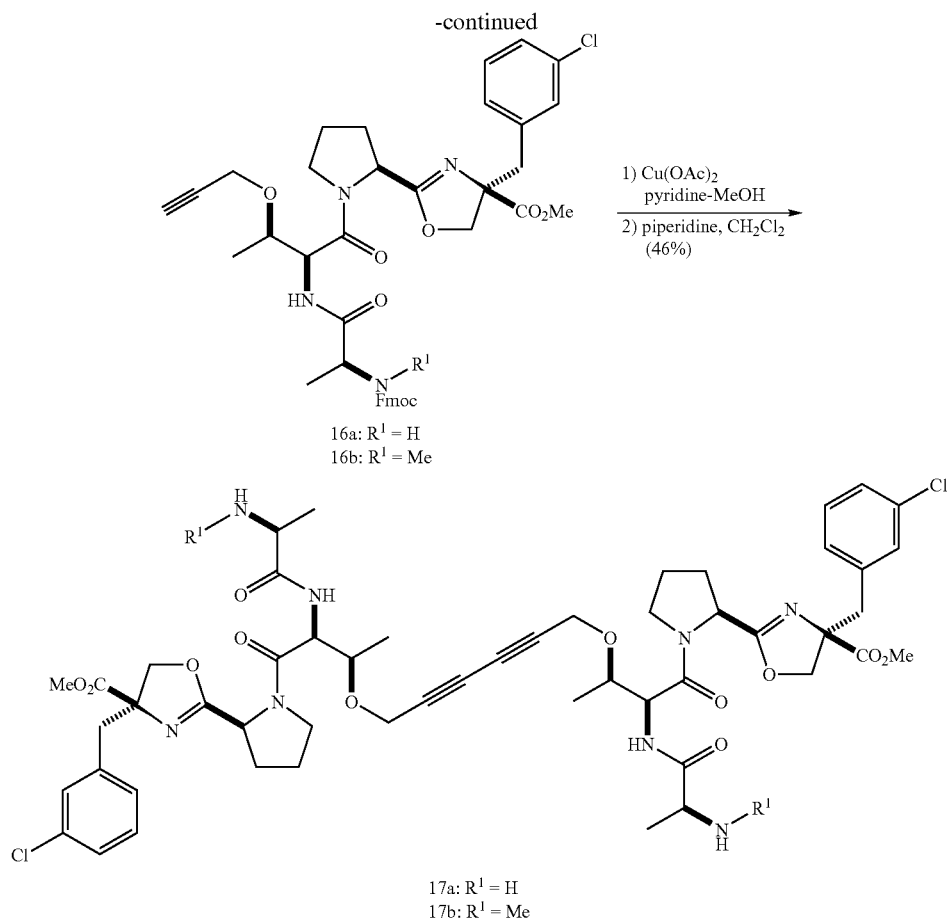

(2S,4R)-2-tert-Butyl-4-(3-chloro-benzyl)-oxazolidine-3,4-dicarboxylic acid 3-tert-butyl ester 4-methyl ester (11)

Under N$_2$, to a solution of 10 [1. Cagnon, J.; Bideau, F.; Marchand-Brynaert, J.; Ghosez, L. *Tetrahedron Lett.*, 1997, 38, 2291; 2. Seebach, D.; Aebi, J. D. *Tetrahedron Lett.* 1984, 25(24), 2545-2548; 3. Seebach, V. D.; Aebi, J.; Gander-Coquoz, M.; Naef, R., *Helvetica Chimica Acta*, 1987, 70, 1194-1216] (1.0 mmol) and 3-chloro benzyl bromide (1.2 mmol) in THF-HMPA (4:1, 10 mL) was added dropwise LHMDS (1.2 mmol) in THF at −78° C. over 30 min. After additional stirring for 30 min at same temperature (−78° C.), the reaction mixture was quenched with sat.NH$_4$Cl (5 mL), and allowed to warm up to room temperature. The separated water phase was extracted with Et$_2$O (3×20 mL). The combined extraction were washed with H$_2$O (20 mL) and Brine (20 mL), dried over MgSO$_4$, filtered and concentrated in vacuo to give the residue. The crude of 11 was used for next step without further purification. A small amount of crude was submitted to silica gel column chromatography with Hexan: EtOAc=20:1 as elute and taken for spectral data. [α]$_D$ −67.3 (c 1.02, CHCl$_3$); $^1$H NMR (CDCl$_3$, 300 MHz) δ 2.74 (d, J=13.2 Hz, 1H), 3.05 (d, J=13.2 Hz, 1H), 3.57 (dd, J=1.5, 10.8 Hz, 1H), 3.73 (s, 3H), 3.87 (d, J=10.8 Hz, 1H), 7.00 (m, 1H), 7.12 (m, 1H), 7.20-7.25 (m, 2H); $^{13}$C NMR (CDCl$_3$, 75 MHz) δ 26.8, 28.3, 38.5, 39.5, 52.6, 69.4, 73.8, 81.5, 97.6, 127.1, 128.4, 129.5, 130.4, 134.0, 138.1, 153.0, 172.0; IR (film): 2976, 1743, 1711, 1359, 1136 cm$^{-1}$; Mass (ESI) 412.19 ([MH]$^+$).

(R)-2-Amino-2-(3-chloro-benzyl)-3-hydroxy-propionic acid methyl ester (12)

Under N$_2$, to a solution of crude of 11 (1 mmol) in dried MeOH (5 mL) was added dropwise conc.HCl (2 mL) over 1 hr then stirred for overnight. After concentration, the residue was basified with NaHCO$_3$ at 0° C. The mixture was extracted with CH$_2$Cl$_2$ (5×20 mL). The combined extraction were dried over MgSO$_4$, filtered and concentrated. The crude was submitted to silica gel column chromatography (CH$_2$Cl$_2$:MeOH: NH$_4$OH=500:9:1-100:9:1) to give 12 (95%, from 10). [α]$_D$ −3.6 (c 1.45, CHCl$_3$); $^1$H NMR (CDCl$_3$, 400 MHz) δ 2.75 (d, J=13 Hz, 1H), 3.05 (d, J=13 Hz, 1H), 3.56 (d, J=10 Hz, 1H), 3.73 (s, 3H), 3.87 (d, J=10 Hz, 1H), 7.02 (m, 1H), 7.13 (m, 1H), 7.22-7.27 (m, 2H). $^{13}$C NMR (CDCl$_3$, 75 MHz) δ 41.5, 52.4, 63.6, 67.7, 127.4, 128.0, 129.8, 129.9, 134.3, 137.5, 175.3; IR (film): 3359, 3300, 3180, 1736, 1083 cm$^{-1}$; Mass (ESI) 244.02 ([MH]$^+$).

(2S,1'R)1-Fmoc-2-[2'-(3"-Chloro-phenyl)-1'-hydroxymethyl-1'-methoxycarbonyl-ethylcarbamoyl]-pyrrolidine (13)

Under N$_2$, to a solution of Fmoc-Pro-OH (1.0 mmol) and amino alcohol 12 (1.0 mmol) in CH$_3$CN (10 mL) was added DMT-MM (1 mmol) then stirred for 3 hr. The reaction mixture was concentrated to half amount. The residue was diluted with $Et_2O$ (30 mL), washed with 5% HCl (20 mL), $H_2O$ (20 mL), 5% NaOH (20 mL), $H_2O$ (20 mL) and Brine (20 mL), dried over $MgSO_4$, filtered and concentrated. The crude was used for next step without further purification. $[\alpha]_D$ −41.8 (c 1.75, $CHCl_3$); $^1H$ ($CDCl_3$, 400 MHz) δ 1.82-1.94 (m, 2H), 2.06-2.30 (m, 2H), 3.02 (d, J=13.4 Hz, 1H), 3.44-3.58 (m, 3H), 3.64 (d, J=13.4 Hz, 1H), 3.77 (s, 3H), 3.84 (t, J=10.1 Hz, 1H), 4.18-4.49 (m, 5H), 6.89 (d, J=6.6 Hz, 1H), 7.05 (s, 2H), 7.16 (m, 2H), 7.30 (t, J=7.3 Hz, 2H), 7.39 (t, J=7.3 Hz, 2H), 7.56 (d, J=7.6 Hz, 2H), 7.75 (d, J=7.6 Hz, 2H). $^{13}C$ ($CDCl_3$, 75 MHz) δ 24.4, 29.3, 36.2, 46.9, 52.9, 62.0, 64.0, 67.6, 68.0, 119.9, 124.9, 125.0, 127.0, 127.5, 127.7, 129.4, 129.7, 133.9, 137.5, 141.1, 141.2, 143.4, 143.8, 156.1, 171.4, 172.0; IR (film): 3392, 1741, 1682, 1418, 758 $cm^{-1}$; Mass (ESI) 585.10 ($[MNa]^+$).

(4R,2'S)-4-(3"-Chloro-benzyl)-2-[1'-Fmoc-pyrrolidin-2'-yl]-4,5-dihydro-oxazole-4-carboxylic acid methyl ester (14)

Under $N_2$, to a cold (−78° C.) solution of 13 (1.0 mmol) in $CH_2Cl_2$ (5 mL) was added DAST (1.2 mmol) dropwise within 10 min at −78° C. then stirred for 1 hr at −78° C. After addition of $K_2CO_3$ (1.5 mmol), the reaction mixture was allowed to warm up to room temperature. The reaction mixture was diluted with sat.$NaHCO_3$ (10 mL) then extracted with $Et_2O$ (3×20 mL). The combined extractions were washed with $H_2O$ (10 mL) and Brine (10 mL), filtered and concentrated in vacuo. The residue was purified by silica gel column chromatography (Hexane:EtOAc=2:1) to afford product 14 (72%, from 14) as white form. $[\alpha]_D$ −61.6 (c 1.90, $CHCl_3$); $^1H$ NMR ($CDCl_3$, 300 MHz, mixture of rotamer) δ 1.77-2.21 (m, 4H), 3.07 and 3.14 (ABq, J=13.7/13.7 Hz, 2H), 3.44-3.72 (m, 2H), 3.56 and 3.70 (s, 3H), 4.03-4.62 (m, 6H), 6.98-7.24 (m, 4H), 7.30 (t, J=7.3 Hz, 2H), 7.39 (t, J=7.3 Hz, 2H), 7.61 (m, 2H), 7.75 (dd, J=5.1, 7.3 Hz, 2H); $^{13}C$ NMR ($CDCl_3$, 75 MHz, mixture of rotamer) δ 23.4 and 24.4, 30.3 and 31.4, 42.6 and 43.0, 46.6 and 47.0, 47.1 and 47.3, 52.6 and 52.6, 54.3 and 54.8, 67.3 and 67.5, 73.3 and 73.3, 77.8 and 78.0, 119.9, 125.0 and 125.1, 125.1 and 125.2, 127.0 and 127.0, 127.2 and 127.3, 127.6, 128.5, 129.5 and 129.5, 130.4 and 130.5, 133.9 and 134.0, 136.9 and 137.2, 141.1 and 141.2, 141.2, 141.2, 143.8 and 143.9, 144.0 and 144.2, 154.4 and 154.6, 169.2 and 169.6, 172.7 and 172.8; IR (film): 2952, 1735, 1705, 1417 $cm^{-1}$; Mass (ESI) 567.15 ($[MNa]^+$).

(2S,3S)-1-Alloc-3-Methyl-aziridine-2-carboxylic acid methyl ester

Under $N_2$, to a solution of known compound (2S,3S)-3-methyl-1-trityl-aziridine-2-carboxylic acid methyl ester [1. Mckeever, B.; Pattenden, G. *Tetrahedron*, 2003, 59, 2713-2727; 2. Wipf, P.; Uto, Y., *J. Org. Chem.*, 2000, 65, 1037-1049] (20 g, 56 mmol) in $CH_2Cl_2$ (100 mL) and MeOH (2.3 mL) was added TFA (8.6 mL, 112 mmol) at 0° C. then stirred for 1 hr. Evaporation of the solvent in vacuo gave a solid residue which was dissolved in $Et_2O$. The solvent was evaporated, and the $Et_2O$ treatment was repeated two additional times to ensure complete removal of TFA. The residue was dissolved in $Et_2O$ and then extracted with $H_2O$ (5×30 mL). To the combined $H_2O$ phase was added portionwise $NaHCO_3$ carefully at 0° C. followed by EtOAc (56 mL) and dropwise Allyl chroloformate (8.9 mL, 84 mmol) at 0° C. then stirred for 16 hr at room temperature. The reaction mixture was extracted with EtOAc (3×100 mL). The combined extraction were washed with $H_2O$ (50 mL) and Brine (50 mL), dried over $MgSO_4$, filtered and concentrated. The crude was purified by silica gel column chromatography with Hexane:EtOAc=10:1 as eluant to give product (59%). $[\alpha]_D$ −81.7 (c 1.02, $CHCl_3$); $^1H$ NMR ($CDCl_3$, 400 MHz) δ 1.36 (d, J=5.7 Hz, 3H), 2.83 (dq, J=5.7, 6.7 Hz, 1H), 3.19 (d, J=6.7 Hz, 1H), 3.79 (s, 3H), 4.61 (m, 2H), 5.26 (dd, J=1.2, 10.4 Hz, 1H), 5.33 (dd, J=1.5, 17.2 Hz, 1H), 5.91 (ddt, J=5.7, 10.4, 17.2 Hz, 1H); $^{13}C$ NMR ($CDCl_3$, 75 MHz) δ 12.8, 38.8, 39.7, 52.3, 67.3, 118.8, 131.5, 161.3, 167.5; IR (film): 1733, 1296, 1282, 1204 $cm^{-1}$; Mass (ESI) 200.10 ($[MH]^+$).

(2S,3R)-2-Alloc-amino-3-prop-2'-ynyloxy-butyric acid methyl ester

Under $N_2$, to a solution of above product (3.2 g, 16 mmol) in propargyl alcohol (186 mL) was added $BF_3.Et_2O$ (4.1 mL, 32 mmol) at room temperature then stirred for 1 hr. The reaction mixture was concentrated in vacuo. The residue was dissolved in $H_2O$ (50 mL) and then extracted with $Et_2O$ (3×40 mL). The combined extraction were washed with $H_2O$ (30 mL) and Brine (30 mL), dried over $MgSO_4$, filtered and concentrated. The crude was purified by silica gel column chromatography with Hexane:AcOEt=10:1 as eluant to give propargyl Threonine derivative (95%). $[\alpha]_D$ 6.9 (c 1.53, $CHCl_3$); $^1H$ NMR ($CDCl_3$, 400 MHz) δ 1.24 (d, J=6.2 Hz, 3H), 2.41 (t, J=2.4 Hz, 1H), 3.77 (s, 3H), 4.12 (qd, J=2.4, 16.1 Hz, 2H), 4.31 (m, 1H), 4.36 (dd, J=2.2, 9.5 Hz, 1H), 4.60 (d, J=5.5 Hz, 2H), 5.22 (dd, J=1.1, 10.4 Hz, 1H), 5.33 (dd, J=1.5, 17.2 Hz, 1H), 5.43 (br d, J=9.3 Hz, 1H), 5.93 (ddt, J=5.5, 10.8, 17.2 Hz, 1H); $^{13}C$ NMR ($CDCl_3$, 75 MHz) δ 15.9, 52.4, 56.0, 58.5, 65.9, 73.8, 74.4, 79.2, 117.7, 132.6, 156.5, 171.0; IR (film): 3292, 1750, 1724, 1517, 1212, 1075 $cm^{-1}$; Mass (ESI) 256.17 ($[MH]^+$).

(2S,3R)-2-Alloc-lamino-3-prop-2'-ynyloxy-butyric acid (9)

Under $N_2$, a solution of above material (1 g, 3.9 mmol) and 0.26N HCl (15 mL) in AcOH (45 mL) was refluxed for 20 hr. The reaction mixture was concentrated. The crude was passed short column chromatography with Hexane:EtOAc=1:1 as eluant to give 9 (95%). $[\alpha]_D$ −1.6 (c 0.99, $CHCl_3$); $^1H$ NMR ($CDCl_3$, 400 MHz) δ 1.27 (d, J=6.4 Hz, 3H), 2.45 (t, J=2.2 Hz, 1H), 4.17 (qd, J=2.2, 15.9 Hz, 2H), 4.34 (m, 1H), 4.41 (d, J=9.2 Hz, 1H), 4.60 (d, J=5.5 Hz, 2H), 5.23 (d, J=10.7 Hz, 1H), 5.32 (d, J=17.2 Hz, 1H), 5.47 (br d, J=9.2 Hz, 1H), 5.92 (ddt, J=5.5, 10.7, 17.2 Hz, 1H); $^{13}C$ NMR ($CDCl_3$, 75 MHz) δ 16.3, 56.5, 58.7, 66.3, 74.2, 75.2, 79.2, 118.1, 132.7, 156.9, 175.8; IR (film): 3293, 1717, 1522, 1076 $cm^{-1}$; Mass (ESI) 242.04 ($[MH]^+$).

(4R,2'S)-2-[1'-Alloc-Thr(propargyl)-pyrrolidin-2'-yl]-4-(3"-chloro-benzyl)-4,5-dihydro-oxazole-4-carboxylic acid methyl ester (15)

14 (634 mg, 1.16 mmol) was treated with 20% piperidine-$CH_2Cl_2$ (10 mL). The reaction mixture was concentrated. The crude was through short column chromatography with $CH_2Cl_2$:MeOH:$NH_4OH$=200:9:1 as elute. The residue was dissolved in DMF and followed by adding 9 (309 mg, 1.28 mmol), DIPEA (404 μL, 2.32 mmol) and HATU (487 mg, 1.28 mmol) at 0° C. then stirred for 30 min. The reaction mixture was diluted with $Et_2O$ and sat.$NaHCO_3$ was added. The aqueous phase was extracted with $Et_2O$. The combined extraction were washed with $H_2O$ and Brine, dried over $MgSO_4$, filtered and concentrated. The crude was purified by silica gel column chromatography with Hexane:EtOAc=1:1 as eluant to give 15 (55%). $^1$H NMR (CDCl$_3$, 400 MHz, mixture of rotamer) δ 1.20 and 1.24 (d, J=6.2/6.2 Hz, 3H), 1.83-2.24 (m, 4H), 2.40 and 2.43 (t, J=2.4/2.4 Hz, 1H), 3.11 and 3.27 (ABq, J=13.7/13.9 Hz, 2H), 3.72-3.75 (s, 3H), 3.50-4.97 (m, 13H), 5.20-5.30 (m, 2H), 5.68 and 5.78 (d, J=8.2/8.4 Hz, 1H), 5.90 (m, 1H), 7.08 (m, 1H), 7.17-7.25 (m, 3H); Mass (ESI) 546.15 ([MH]$^+$), 568.10 ([MNa]$^+$)

(4R,2'S)-2-[1'-Fmoc-Ala-Thr(propargyl)-pyrrolidin-2'-yl]-4-(3"-chloro-benzyl)-4,5-dihydro-oxazole-4-carboxylic acid methyl ester (16)

Under N$_2$, to a solution of Fmoc-Ala-OH (633 mg, 1.9 mmol) and HOBt (305 mg, 1.9 mmol) in CH$_2$Cl$_2$ (40 mL) was added EDCI (369 mg, 1.9 mmol) at 0° C. and then stirred for 1 hr at 0° C. and additional 1 hr at room temperature. To the reaction mixture was added Pd(PPh$_3$)$_4$ (295 mg, 0.26 mmol), a solution of 15 (350 mg, 0.64 mmol) and DABCO (359 mg, 3.2 mmol) and then stirred for 20 min. The reaction mixture was concentrated in vacuo and then submitted to silica gel column chromatography with Hexane:EtOAc=1:1~1:9 as eluent to give 16 (99%). $^1$H NMR (CDCl$_3$, 400 MHz, mixture of rotamer) δ 1.17 and 1.22 (d, J=6.4/6.4 Hz, 3H), 1.40 (br d, J=7.7 Hz, 3H), 1.81-2.16 (m, 4H), 2.31 and 2.38 (t, J=2.4/2.4 Hz, 1H), 3.10 and 3.24 (ABq, J=13.9/13.9 Hz, 2H), 3.72 and 3.74 (s, 3H), 3.70-5.00 (m, 9H), 5.36 (m, 1H), 6.75 (d, J=7.3 Hz, 1H), 7.05-7.70 (m, 10H), 7.76 (d, J=7.5 Hz, 2H); Mass (ESI) 755.15 ([MH]$^+$).

Compound 17a.

Under O$_2$, the mixture of 18 (34 mg, 0.045 mmol), CuI (8.6 mg, 0.045 mmol) and pyridine (11 μL, 0.135 mmol) in THF (0.45 mL) was stirred for 20 hrs. The reaction mixture was diluted with 10% glycine aq and extracted with CH$_2$Cl$_2$ (5×5 mL). The combined extraction were dried over MgSO$_4$, filtered and concentrated. The crude of 19 was treated with 20% piperidine-DMF for 10 min. The reaction mixture was concentrated and purified by preparative TLC with CH$_2$Cl$_2$:MeOH:NH$_4$OH=100:9:1 as eluent to give 17a (46% from 18). $^1$H NMR (CDCl$_3$, 400 MHz, 20 has rotamer, only major rotamer was shown) δ 1.21 (d, J=6.2 Hz, 6H), 1.36 (d, J=7.0 Hz, 6H), 1.80-2.12 (m, 8H), 3.11 (ABq, J=13.7 Hz, 4H), 3.48-3.96 (m), 4.15 (d, J=9.2 Hz, 2H), 4.30 (q, J=16.5 Hz, 4H), 4.58 (d, J=9.2 Hz 2H), 4.61-4.93 (m, ), 7.06-7.10 8 (m, 2H), 7.17-7.24 (m, 6H), 7.94 (d, J=8.4 Hz, 2H); Mass (ESI) 532.38 ([[M$^+$/2]H]$^+$), 1063.61 ([MH]$^+$).

N-Me dimer (R=Me, 17b) was synthesized by same procedure as above described for 17a.

$^1$H NMR (CDCl$_3$, 400 MHz, 17b has rotamer) δ 1.19 and 1.22 (d, J=6.2/6.4 Hz, 6H), 1.29 and 1.31 (d, J=6.6/6.8 Hz, 6H), 1.80-2.12 (m, 8H), 2.40 and 2.42 (s, 6H), 3.10 and 3.28 (ABq, J=13.6/13.8 Hz, 4H), 3.72 and 3.74 (s, 6H), 3.71-3.96 (m, 6H), 4.14 and 4.28 (A of ABq, J=9.2/9.0 Hz, 2H), 4.31 (ABq, J=16.3 Hz, 2H), 4.58 and 4.62 (B of ABq, J=9.2/9.0 Hz, 2H), 4.66-4.94 (m, 2H), 7.06-7.10 (m, 2H), 7.18-7.25 (m, 6H), 7.80 (d, J=8.4 Hz, 2H); Mass (ESI) 546.85 ([[M$^+$/2]H]$^+$), 1113.35 ([MNa]$^+$).

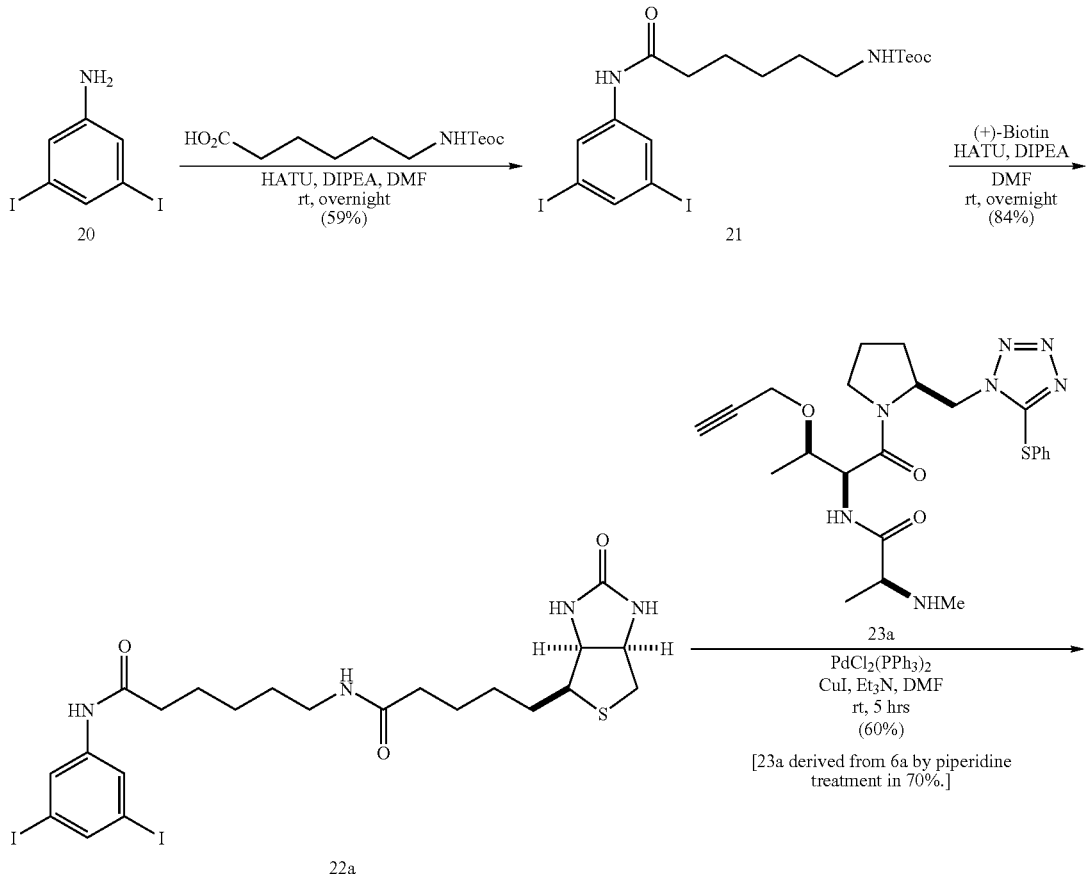

Scheme 7

[23a derived from 6a by piperidine treatment in 70%.]

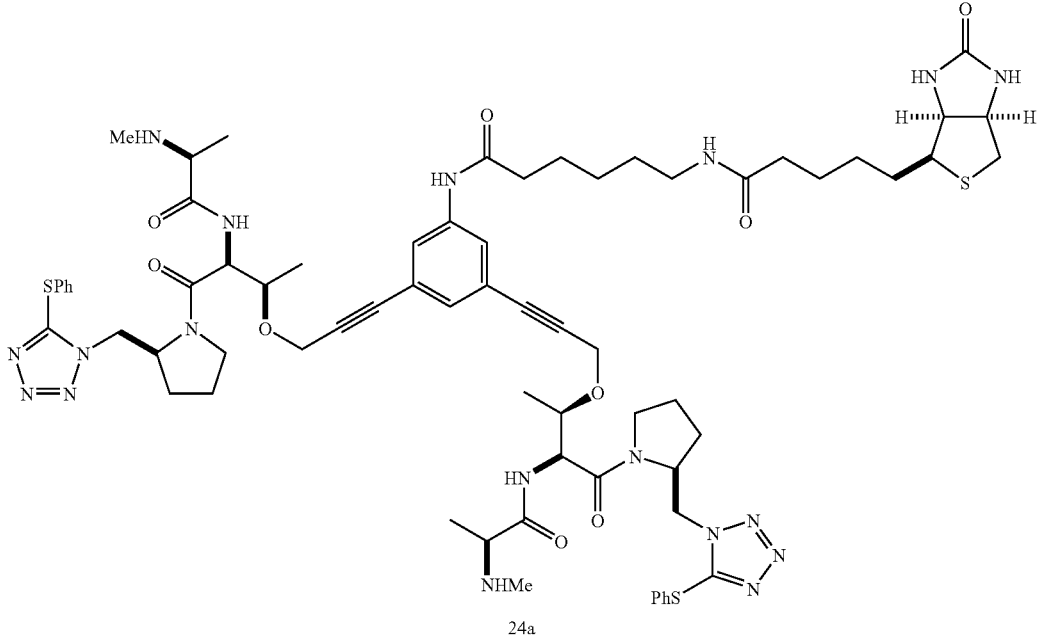

24a

[5-(3,5-Diiodo-phenylcarbamoyl)-pentyl]-carbamic acid 2-trimethylsilanyl-ethyl ester (21)

3,5-Diiodoaniline [Dininno, F.; Guthikonda, R. N.; Schmitt, S. M. 1994 U.S. Pat. No. 5,292,879 A] (1 g, 2.90 mmol), 6-(2-Trimethylsilanyl-ethoxycarbonylamino)-hexanoic acid (1 g, 3.77 mmol) in DMF (12 ml) were added DIPEA (0.9 ml, 5.8 mmol) and HATU (1.65 g, 4.35 mmol). The mixture was stirred for overnight at room temperature. The reaction mixture was diluted with Et$_2$O. To the mixture was added sat.NaHCO$_3$ and then separated. The aqueous phase was extracted with Et$_2$O (3×40 ml). The combined extraction were washed with 5% HCl (30 ml), H$_2$O (50 ml), sat.NaHCO$_3$ (30 ml), and Brine (30 ml), and finally dried over MgSO$_4$, filtered and concentrated in vacuo. The crude was purified by silica gel column with (Hexane:EtOAc=6:4) to afford 21 (1 g, 59%) as a colorless powder. $^1$H NMR (300 MHz, (CD$_3$)$_2$SO): δ 0.09 (S, 9H), 0.84 (t, J=2.1 Hz, 2H), 1.34 (m, 2H), 1.40 (m, 2H), 1.50 (m, 2H), 2.41 (t, J=1.8 Hz, 2H), 2.47 (m, 2H), 2.89 (m, 2H), 4.01 (t, 2H), 6.92 (bt, 1H), 7.68 (m, 1H), 7.99 (m, 2H); $^{13}$C NMR (75 MHz, (CD$_3$)$_2$SO): δ −0.72, 18.0, 25.2, 26.4, 29.9, 36.9, 61.9, 96.4, 127.0, 139.0, 142.3, 156.9, 172.2; IR (film): 3326, 2853, 2361, 1687, 1541, 1450, 1249, 837 cm$^{-1}$; MS:(ESI)) [M+Na]$^+$ 624.9

6-[4-(2-Oxo-hexahydro-thieno[3,4-d]imidazol-6-yl)-butyrylamino]-hexanoic acid(3,5-diiodo-phenyl)-amide (22a)

The above compound 21 (0.37 g, 0.61 mmol) was treated with 50% TFA-CH$_2$Cl$_2$ (4 ml) for 1 hr. The solvent was evaporated to furnish a crude, which was subjected for next step without any further purification.

The salt (0.34 g, 0.59 mmol), (+)-Biotin (0.18 g, 0.76 mmol) in DMF (4 ml) were added DIPEA (0.3 ml, 1.7 mmol) and HATU (0.33 g, 0.88 mmol). The mixture was stirred for overnight at room temperature. The reaction mixture was concentrated in vacuo, The crude was purified by silica gel column with (MeOH:CHCl$_3$:NH$_4$OH=1:9:0.1) to afford 22a (0.3 g, 84%) as flakes. [α]$_D$ +16 (c 1, DMF). $^1$H NMR (400 MHz, (CD$_3$)$_2$SO): δ 1.25-1.60 (m, 12H), 1.95 (t, J=1.8 Hz, 2H), 2.27 (m, 2H), 2.89 (m, 2H), 3.01 (m, 2H), 3.15 (m, 4H), 3.61 (m, 2H), 4.15 (m, 1H), 4.25 (m, 1H), 6.40 (d, 1H), 7.60 (s, 1H), 8.00 (s, 2H); $^{13}$C NMR (75 MHz, (CD$_3$)$_2$SO): 25.2, 26.0, 26.6, 28.6, 28.8, 29.6, 35.8, 36.9, 38.7, 42.4, 54.0, 56.1, 59.7, 96.4, 126.9, 139.0, 142.2; IR (film) 3296, 2930, 1675, 1571, 1201, 719 cm$^{-1}$; MS: (ESI) [M+Na]$^+$ 707.

6-[4-(2-Oxo-hexahydro-thieno[3,4-d]imidazol-6-yl)-butyrylamino]-hexanoic acid(3,5-bis-(3-{1-methyl-2-(1-methylamino-ethylamino)-3-oxo-3-[2-(5-phenylsulfanyl-tetrazol-1-ylmethyl)-pyrrolidin-1-yl]-propoxy}-prop-1-ynyl)-phenyl)-amide (24a)

22a (0.026 g, 0.039 mmol) and 23a (0.038 g, 0.078 mmol) in DMF were added PdCl$_2$(PPh$_3$)$_2$ (2.7 mg, 10 mol %), CuI (1.1 mg, 16 mol %) and Et$_3$N (27 μl, 0.19 mmol). The reaction mixture was stirred for 5 hrs at room temperature. Solvent was evaporated and the resultant mixture was purified by preparative TLC using (CHCl$_3$:MeOH:NH$_4$OH=8:2:0.4) to furnish the desired product 24a in 60% chemical yield. [α]$_D$ +10 (C 1, CHCl$_3$). $^1$H NMR (400 MHz, CDCl$_3$): δ 1.09 (d, J=8.4 Hz, 6H), 1.11 (d, J=6.8 Hz, 6H), 1.45-1.81 (m, 20H), 1.97 (t, J=7.6 Hz, 2H), 2.13 (dd, J=4.4, 12 Hz, 2H), 2.21 (s, 6H), 2.53 (d, J=12.8 Hz, 1H), 2.89 (m, 5H), 3.40 (m, 2H), 3.42-3.60 (m, 4H), 3.95 (m, 2H), 4.15 (m, 2H), 4.19 (ABq, J=19.0 Hz, 4H), 4.37 (m, 2H), 4.45 (dd, J=4.8, 14 Hz, 2H), 4.57 (bd, 2H), 6.95 (s, 1H), 7.22 (m, 6H), 7.38 (m, 4H), 7.78 (s, 2H); $^{13}$CNMR (75 MHz, CDCl$_3$):16.1, 19.6, 24.3, 24.9, 25.5, 26.2, 27.5, 27.7, 29.1, 35.2, 37.1, 39.2, 40.9, 47.8, 48.8, 54.9, 55.7, 56.2, 56.8, 60.3, 61.9, 73.5, 84.8, 85.9, 93.8, 122.1, 127.6, 128.8, 130.0, 133.5, 135.1, 139.8, 163.9, 169.7, 173.4, 185.6; I.R: 3307, 2931, 1651, 1430, 1087, 667 cm$^{-1}$; MS: (ESI) [M+1]$^+$ 1399.9.

Scheme 8
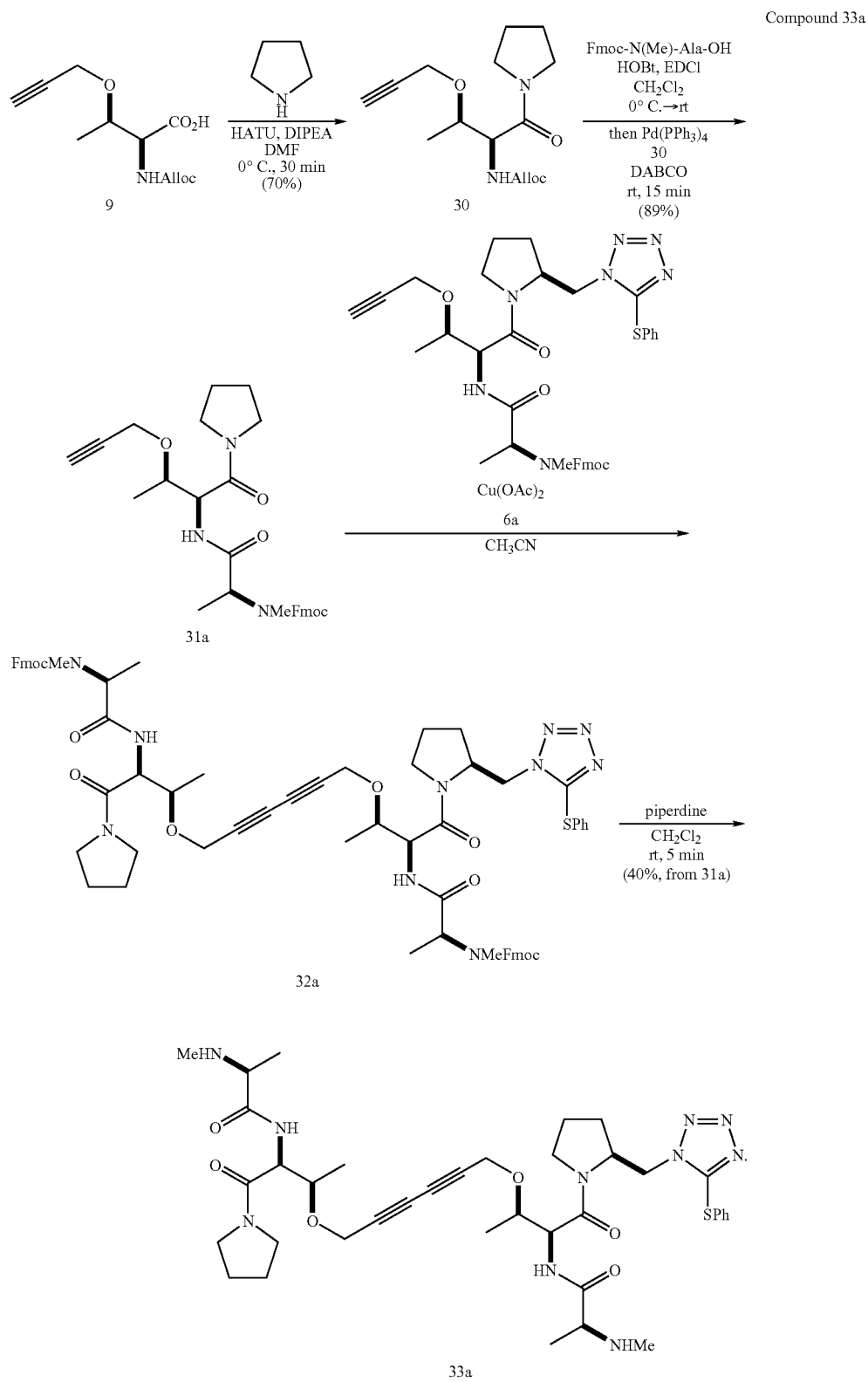
33a was synthesized according to scheme 8.

$^1$H NMR (CDCl$_3$, 400 MHz) δ 1.18 (d, J=6.2 Hz, 3H), 1.23 (d, J=6.3 Hz, 3H), 1.31 (d, J=7.0 Hz, 3H), 1.32 (d, J=7.0 Hz, 3H), 1.75-2.00 (m, 8H), 2.40 (s, 3H), 2.43 (s, 3H), 3.07 (q, J=7.0 Hz, 1H), 3.12 (q, J=7.0 Hz, 1H), 3.40-3.78 (m, 7H), 3.97 (dq, J=4.8, 6.2 Hz, 1H), 4.06 (dq, J=4.4, 6.2 Hz, 1H), 4.21-4.48 (m, 5H), 4.68 (dd, J=4.0, 13.4 Hz, 1H), 4.75 (dd, J=4.4, 8.8 Hz, 1H), 7.40 (m, 3H), 7.62 (m, 2H), 7.81 (bd, J=8.6 Hz, 1H), 7.88 (bd, J=8.6 Hz, 1H); Mass (ESI) [MNa]$^+$ 801.35.

Scheme 9

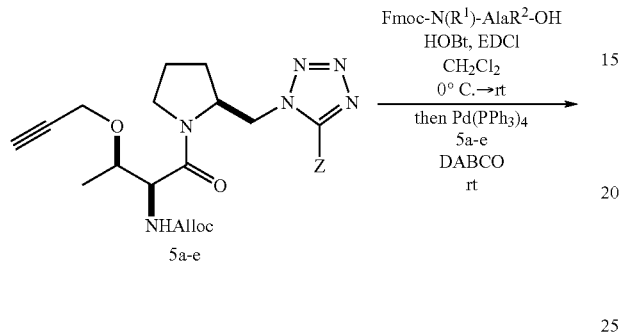

a: R$^1$ = Me, R$^2$ = H, Z = SPh
b: R$^1$ = Me, R$^2$ = H, Z = OPh
c: R$^1$ = Me, R$^2$ = H, Z = OBn
d: R$^1$ = Me, R$^2$ = H, Z = NHBn
e: R$^1$ = Me, R$^2$ = H, Z = NMeBn
f: R$^1$ = H, R$^2$ = H, Z = SPh
g: R$^1$ = H, R$^2$ = H, Z = OPh
h: R$^1$ = H, R$^2$ = H, Z = OBn
i: R$^1$ = H, R$^2$ = H, Z = NHBn
j: R$^1$ = H, R$^2$ = H, Z = NMeBn
k: R$^1$ = H, R$^2$ = Me, Z = SPh
l: R$^1$ = H, R$^2$ = Me, Z = OPh
m: R$^1$ = H, R$^2$ = Me, Z = OBn
n: R$^1$ = H, R$^2$ = Me, Z = NHBn
o: R$^1$ = H, R$^2$ = Me, Z = NMeBn
p: R$^1$ = Me, R$^2$ = Me, Z = SPh
q: R$^1$ = Me, R$^2$ = Me, Z = OPh
r: R$^1$ = Me, R$^2$ = Me, Z = OBn
s: R$^1$ = Me, R$^2$ = Me, Z = NHBn
t: R$^1$ = Me, R$^2$ = Me, Z = NMeBn 6f-t is synthesized same procedure as 6a-e.

Scheme 10

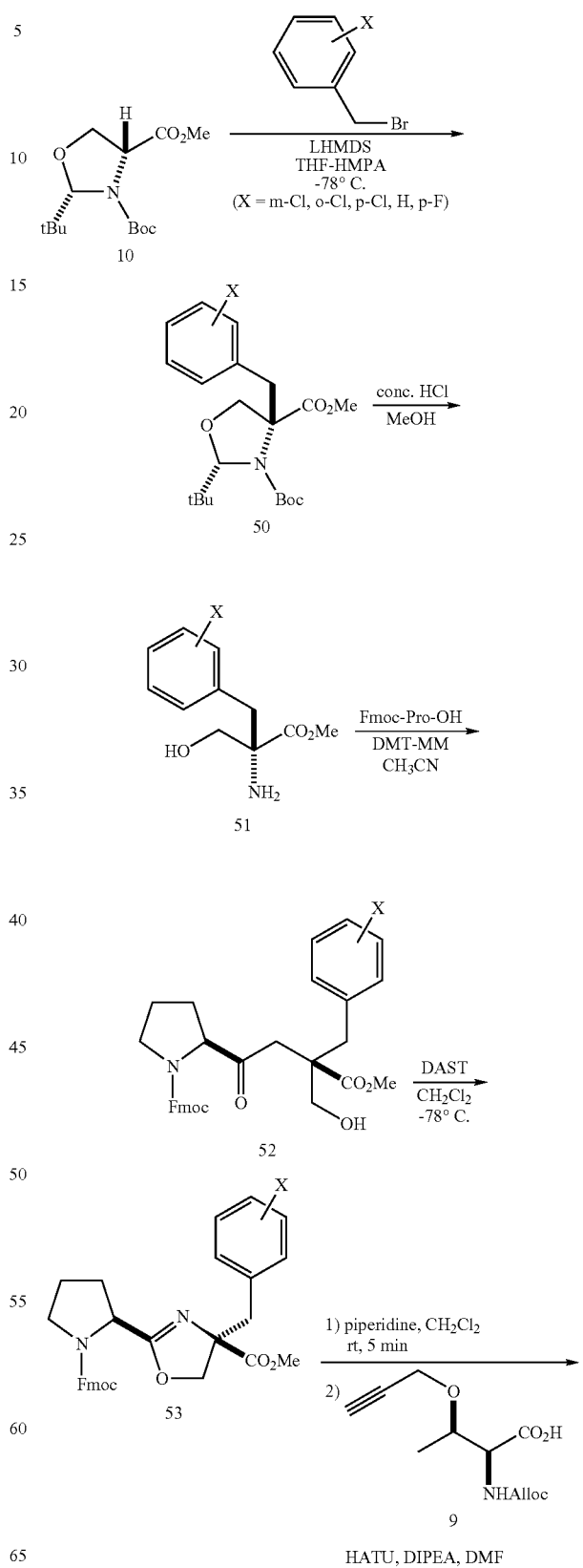

-continued

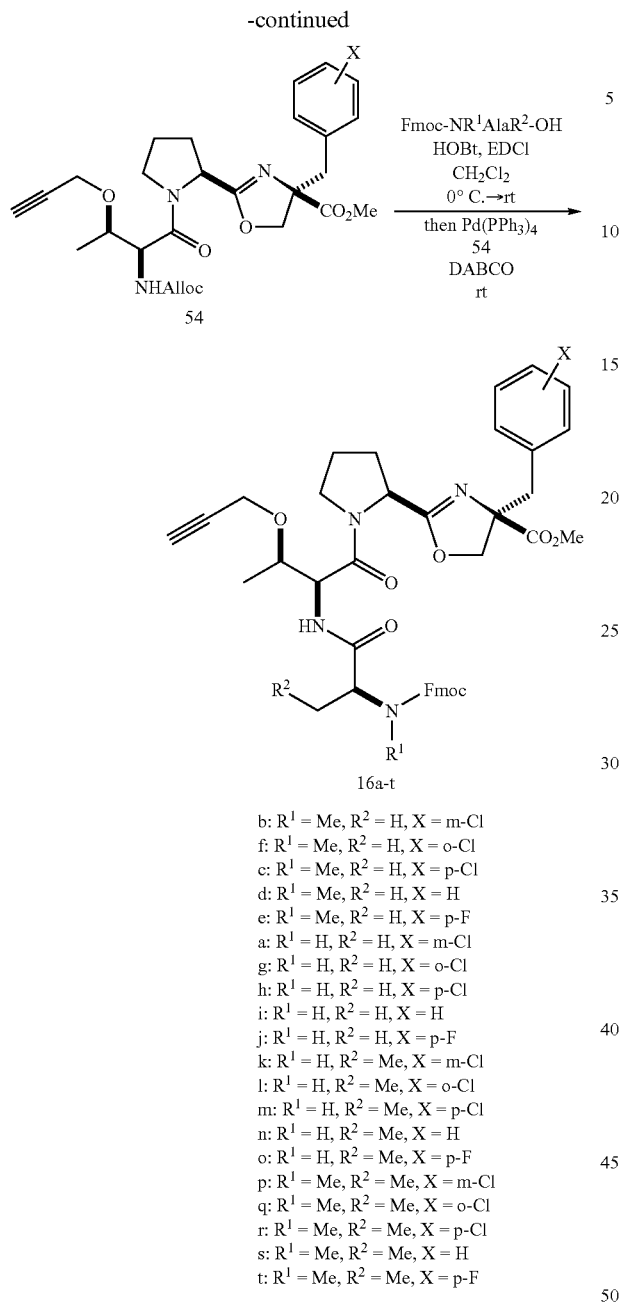

16a-t b: $R^1$ = Me, $R^2$ = H, X = m-Cl
f: $R^1$ = Me, $R^2$ = H, X = o-Cl
c: $R^1$ = Me, $R^2$ = H, X = p-Cl
d: $R^1$ = Me, $R^2$ = H, X = H
e: $R^1$ = Me, $R^2$ = H, X = p-F
a: $R^1$ = H, $R^2$ = H, X = m-Cl
g: $R^1$ = H, $R^2$ = H, X = o-Cl
h: $R^1$ = H, $R^2$ = H, X = p-Cl
i: $R^1$ = H, $R^2$ = H, X = H
j: $R^1$ = H, $R^2$ = H, X = p-F
k: $R^1$ = H, $R^2$ = Me, X = m-Cl
l: $R^1$ = H, $R^2$ = Me, X = o-Cl
m: $R^1$ = H, $R^2$ = Me, X = p-Cl
n: $R^1$ = H, $R^2$ = Me, X = H
o: $R^1$ = H, $R^2$ = Me, X = p-F
p: $R^1$ = Me, $R^2$ = Me, X = m-Cl
q: $R^1$ = Me, $R^2$ = Me, X = o-Cl
r: $R^1$ = Me, $R^2$ = Me, X = p-Cl
s: $R^1$ = Me, $R^2$ = Me, X = H
t: $R^1$ = Me, $R^2$ = Me, X = p-F 16c-t is synthesized adopting similar procedure described for 16a, b.

Scheme 11

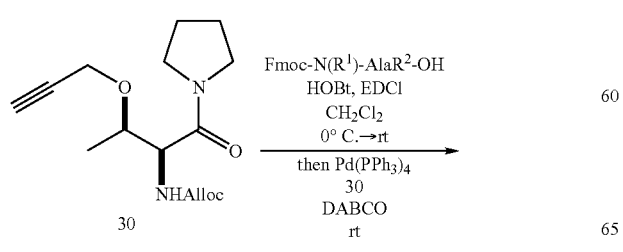

-continued

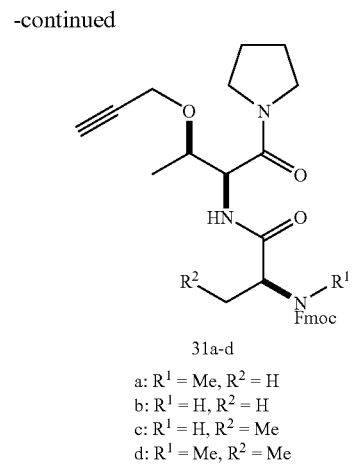

31a-d a: $R^1$ = Me, $R^2$ = H
b: $R^1$ = H, $R^2$ = H
c: $R^1$ = H, $R^2$ = Me
d: $R^1$ = Me, $R^2$ = Me 31b-d is synthesized in a similar procedure described for 31a.

Scheme 12

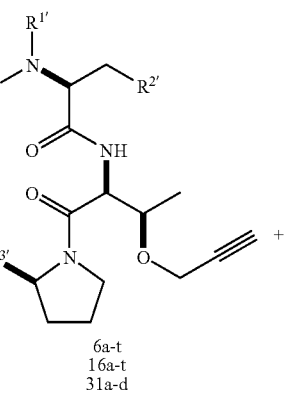

6a-t
16a-t
31a-d

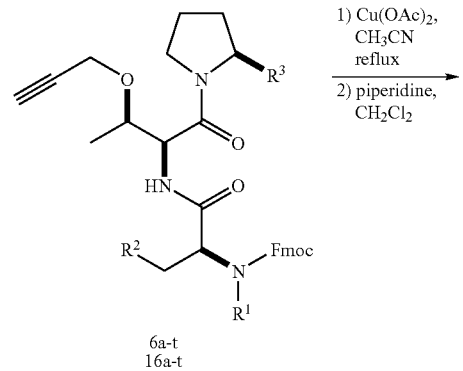

6a-t
16a-t

-continued

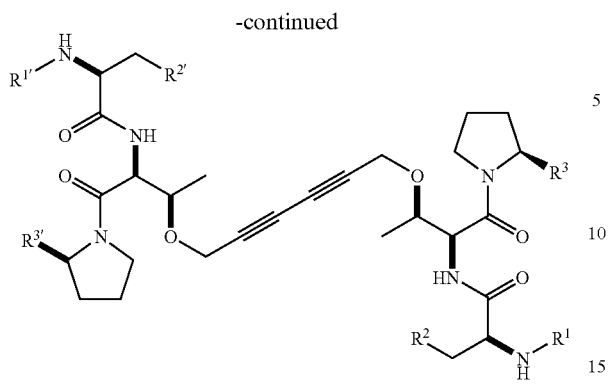

18

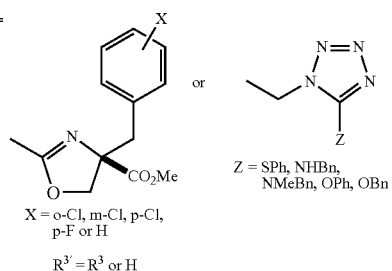

$R^1$, $R^{1'}$ = H or Me $R^2$, $R^{2'}$ = H or Me $R^3$ =

Z = SPh, NHBn, NMeBn, OPh, OBn

X = o-Cl, m-Cl, p-Cl, p-F or H $R^{3'}$ = $R^3$ or H

All homodimeric or heterodimeric combinations of 6a-t or 16a-t with 6a-t or 16a-t or 31a-d.

18 is synthesized in a similar procedure described for 8a-e.

Scheme 13

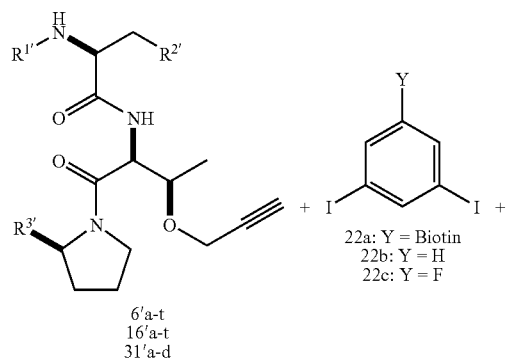

6'a-t
16'a-t
31'a-d

22a: Y = Biotin
22b: Y = H
22c: Y = F

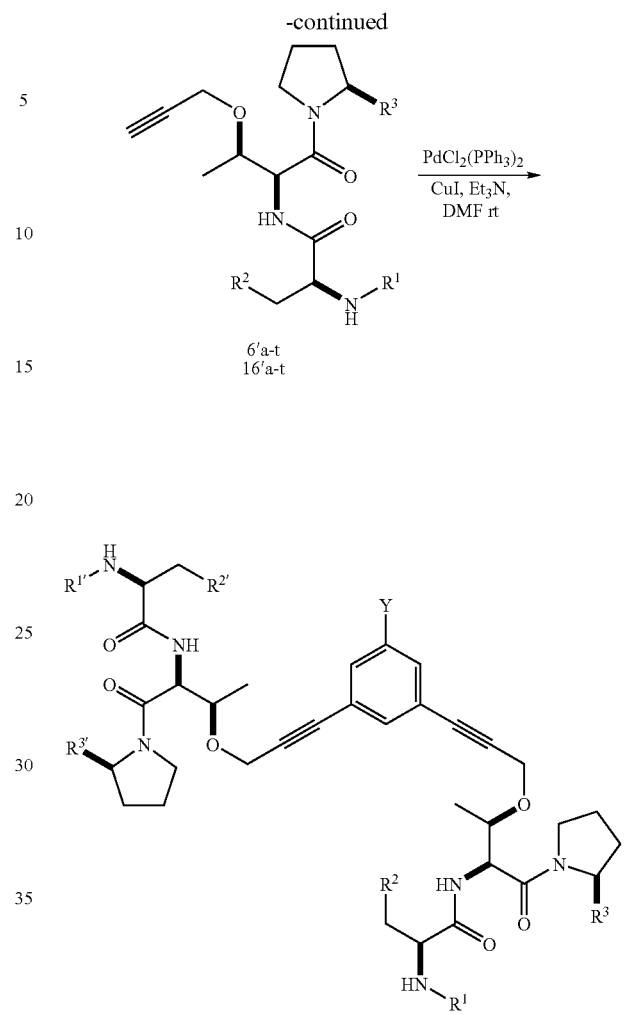

6'a-t
16'a-t

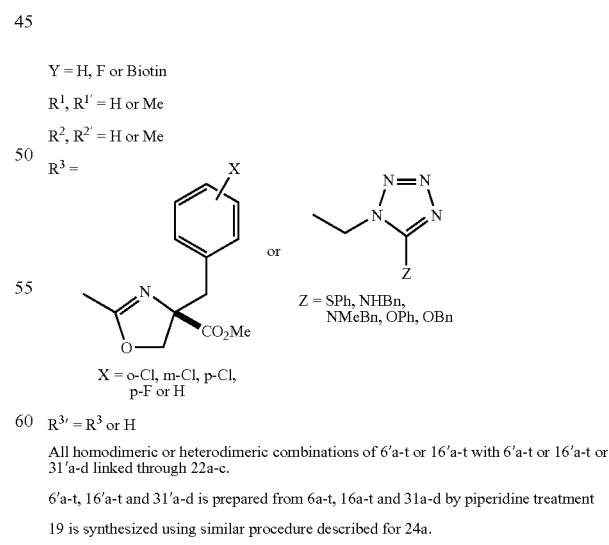

19

Y = H, F or Biotin $R^1$, $R^{1'}$ = H or Me $R^2$, $R^{2'}$ = H or Me $R^3$ =

Z = SPh, NHBn, NMeBn, OPh, OBn

X = o-Cl, m-Cl, p-Cl, p-F or H $R^{3'}$ = $R^3$ or H

All homodimeric or heterodimeric combinations of 6'a-t or 16'a-t with 6'a-t or 16'a-t or 31'a-d linked through 22a-c.

6'a-t, 16'a-t and 31'a-d is prepared from 6a-t, 16a-t and 31a-d by piperidine treatment 19 is synthesized using similar procedure described for 24a.

Scheme 14

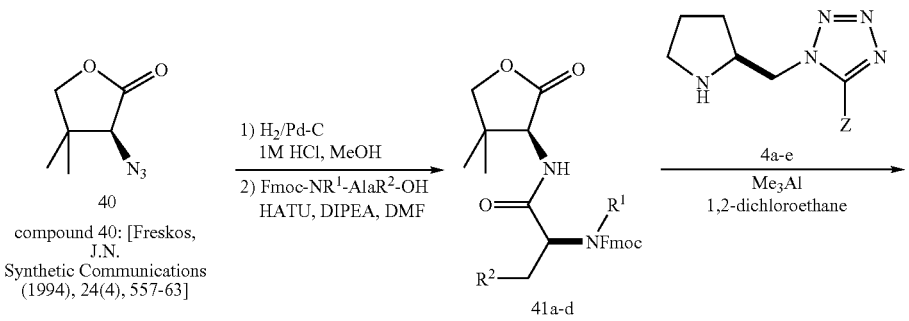

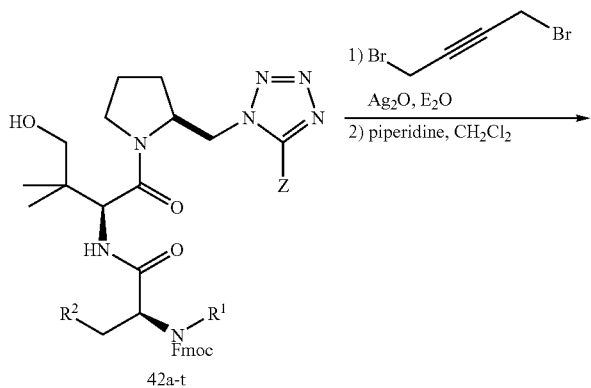

a: $R^1$ = Me, $R^2$ = H, Z = SPh
b: $R^1$ = Me, $R^2$ = H, Z = OPh
c: $R^1$ = Me, $R^2$ = H, Z = OBn
d: $R^1$ = Me, $R^2$ = H, Z = NHBn
e: $R^1$ = Me, $R^2$ = H, Z = NMeBn
f: $R^1$ = H, $R^2$ = H, Z = SPh
g: $R^1$ = H, $R^2$ = H, Z = OPh
h: $R^1$ = H, $R^2$ = H, Z = OBn
i: $R^1$ = H, $R^2$ = H, Z = NHBn
j: $R^1$ = H, $R^2$ = H, Z = NMeBn
k: $R^1$ = H, $R^2$ = Me, Z = SPh
l: $R^1$ = H, $R^2$ = Me, Z = OPh
m: $R^1$ = H, $R^2$ = Me, Z = OBn
n: $R^1$ = H, $R^2$ = Me, Z = NHBn
o: $R^1$ = H, $R^2$ = Me, Z = NMeBn
p: $R^1$ = Me, $R^2$ = Me, Z = SPh
q: $R^1$ = Me, $R^2$ = Me, Z = OPh
r: $R^1$ = Me, $R^2$ = Me, Z = OBn
s: $R^1$ = Me, $R^2$ = Me, Z = NHBn
t: $R^1$ = Me, $R^2$ = Me, Z = NMeBn

R1, R2, R1′, R2′ = H or Me

Z, Z′ = SPh, NHBn, NMeBn, OPh, OBn

All homodimeric or heterodimeric combinations of 42a-t with 42a-t.

60 is obtained by reacting 42a-t with propargyl dibromide in presence of Ag$_2$O in Et$_2$O.

Scheme 15 a: R$^1$ = Me, R$^2$ = H, Z = SPh
b: R$^1$ = Me, R$^2$ = H, Z = OPh
c: R$^1$ = Me, R$^2$ = H, Z = OBn
d: R$^1$ = Me, R$^2$ = H, Z = NHBn
e: R$^1$ = Me, R$^2$ = H, Z = NMeBn
f: R$^1$ = H, R$^2$ = H, Z = SPh
g: R$^1$ = H, R$^2$ = H, Z = OPh
h: R$^1$ = H, R$^2$ = H, Z = OBn
i: R$^1$ = H, R$^2$ = H, Z = NHBn
j: R$^1$ = H, R$^2$ = H, Z = NMeBn
k: R$^1$ = H, R$^2$ = Me, Z = SPh
l: R$^1$ = H, R$^2$ = Me, Z = OPh
m: R$^1$ = H, R$^2$ = Me, Z = OBn
n: R$^1$ = H, R$^2$ = Me, Z = NHBn
o: R$^1$ = H, R$^2$ = Me, Z = NMeBn
p: R$^1$ = Me, R$^2$ = Me, Z = SPh
q: R$^1$ = Me, R$^2$ = Me, Z = OPh
r: R$^1$ = Me, R$^2$ = Me, Z = OBn
s: R$^1$ = Me, R$^2$ = Me, Z = NHBn
t: R$^1$ = Me, R$^2$ = Me, Z = NMeBn 43a-t is synthesized according to similar procedures as above described for 60 using treatment with propargyl bromide and Ag$_2$O in Et$_2$O, followed by standard work-up procedures.

Scheme 16
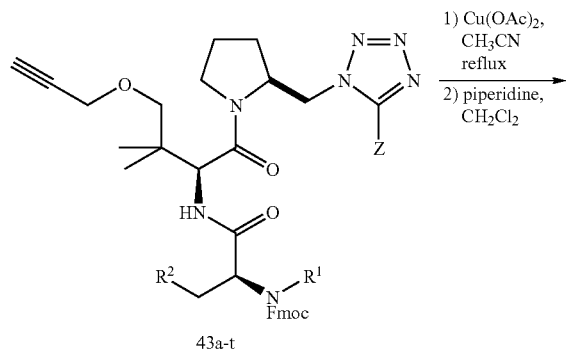
43a-t
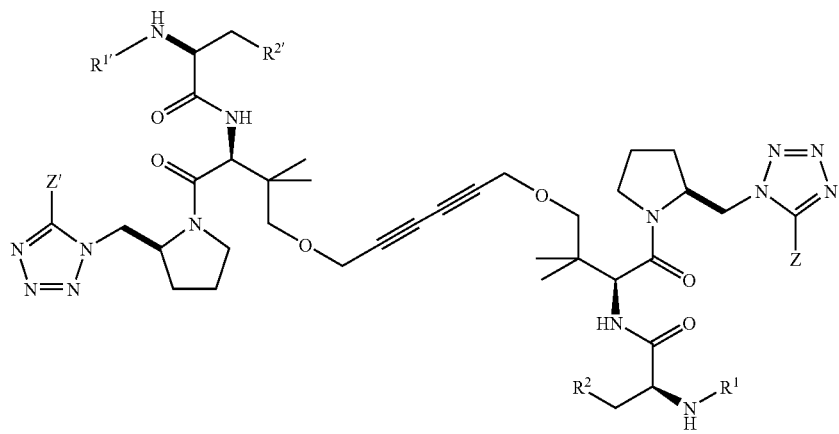
61
R1, R2, R1′, R2′ = H or Me
Z, Z′ = SPh, NHBn, NMeBn, OPh, OBn
All homodimeric or heterodimeric combinations of 43a-t with 43a-t.
61 is synthesized according to similar procedures as described above for 18 using Cu(OAc)$_2$ in CH$_3$CN.
Scheme 17
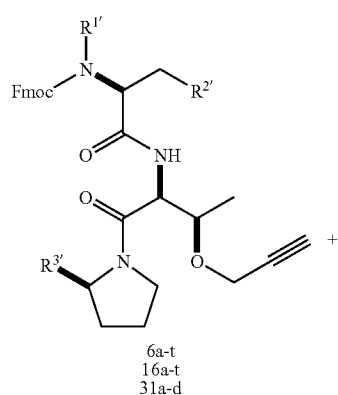
6a-t
16a-t
31a-d
+
-continued
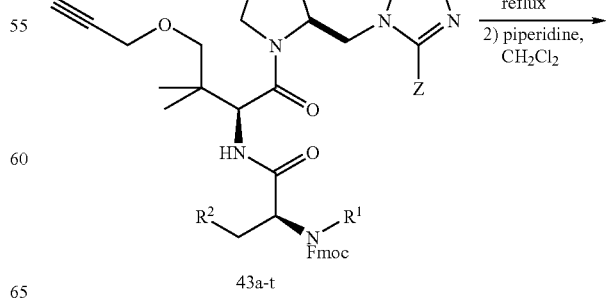
43a-t -continued

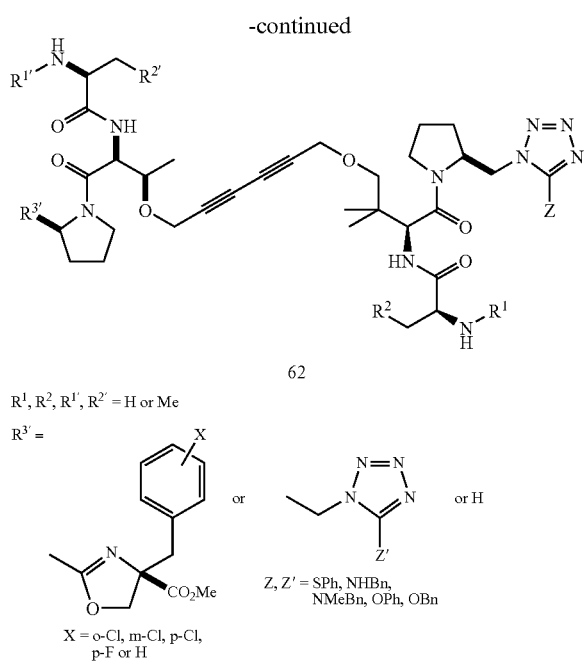

$R^1, R^2, R^{1'}, R^{2'}$ = H or Me $R^{3'}$ =

X = o-Cl, m-Cl, p-Cl, p-F or H

Z, Z' = SPh, NHBn, NMeBn, OPh, OBn

All heterodimeric combinations of 43a-t with 6a-t or 16a-t or 31a-d.

62 may be synthesized according to similar procedures as described above for 18 using Cu(OAc)$_2$ in CH$_3$CN.

What is claimed is:

1. A pro-apoptotic Smac (second mitochondria-derived activator of caspases) peptide mimetic dimeric compound of the general formula M1-L-M2, wherein moieties M1 and M2 are monomeric Smac mimetics and L is a linker covalently linking M1 and M2 in the active dimeric compound, wherein M1-L-M2 is of formula II, formula II

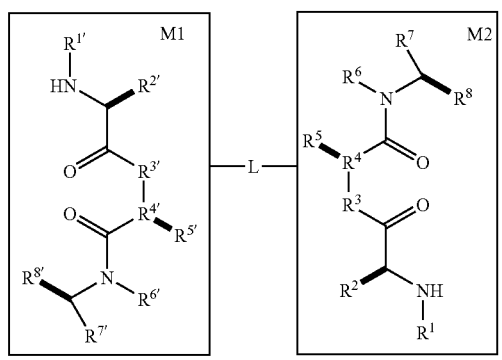

wherein:
R1 and R1' are selected from hydrogen, optionally substituted methyl, and hydroxyl;
R2 and R2' are selected from optionally substituted methyl and optionally substituted ethyl;
R3 and R3' are selected from CH2, NH, O and S;
R4 and R4' are selected from CH and N;
R5-R8, and R5'-R8' are selected from hydrogen, optionally hetero-, optionally substituted alkyl, optionally hetero-, optionally substituted alkenyl, optionally hetero-, optionally substituted alkynyl, optionally hetero-, optionally substituted aryl, wherein optionally either R6 and R7 as well as R6' and R7' or R7 and R8 as well as R7' and R8' are connected in 5- to 8-membered rings; and
L is a contiguous chain of between 2 and 200 atoms, having a MW between 20 D and 2 KD that can incorporate substitution, heteroatoms, unsaturation and cyclic aromatic and heteroaromatic portions, covalently linking any of R2, R5, R6 or R7, with any of R2', R5', R6' or R7', or a pharmaceutically-acceptable salt thereof.

2. The compound of claim 1, wherein R1 and R1' are selected from hydrogen and methyl.

3. The compound of claim 1, wherein R2 and R2' are selected from methyl and ethyl.

4. The compound of claim 1, wherein R3 and R3' are NH.

5. The compound of claim 1, wherein R4 and R4' are CH.

6. The compound of claim 1, wherein R5 and R5' are C1-C3 alkyl.

7. The compound of claim 1, wherein R1 and R1' are selected from hydrogen and methyl, R2 and R2' are selected from methyl and ethyl, R3 and R3' are NH, R4 is CH, and R5 and R5' are C1-C3 alkyl, and L covalently links R5, R6 or R7, with R5', R6' or R7'.

8. The compound of claim 1, wherein either R6 and R7 as well as R6' and R7' or R7 and R8 as well as R7' and R8' are connected in 5- to 8-membered rings.

9. The compound of claim 1, wherein R7 and R8 are connected in a 5- or 6-membered ring.

10. The compound of claim 1, wherein R6 and R7 are connected in a 5- or 6-membered ring.

11. The compound of claim 1, wherein R6 and R7 are connected in a 5-membered ring, and L covalently links the ring with R2', R5', R6' or R7'.

12. The compound of claim 1, wherein R8 comprises a 5- or 6-membered ring.

13. The compound of claim 1, wherein R8 comprises a 5-membered ring, comprising at least one heteroatom, at least one substitution, and at least one unsaturation.

14. The compound of claim 1, wherein R1 and R2, and R1' and R2' are connected in 5-membered rings.

15. The compound of claim 1, wherein L is a contiguous chain of between 4 and 100 atoms, and between 40 D and 1 kD.

16. The compound of claim 1, wherein L is an optionally hetero-, optionally substituted dialkynyl radical.

17. The compound of claim 1, wherein L is substituted with a protonated or alkylated amine wherein the compound is a triamine.

18. The compound of claim 1, wherein the dimer is symmetrical about the linker.

19. The compound of claim 1, wherein the dimer is symmetrical.

20. A pharmaceutical composition comprising the compound of claim 1 and a pharmaceutically acceptable excipient.

21. A pharmaceutical composition comprising the compound of claim 1 and a pharmaceutically acceptable excipient, copackaged with instructions describing use of the composition to treat a disease associated with undesirable caspase activity.

22. The pharmaceutical composition of claim 20 comprising a unit dosage of the compound.

23. The compound of claim 1, comprising a monomer selected from the group consisting of:

97
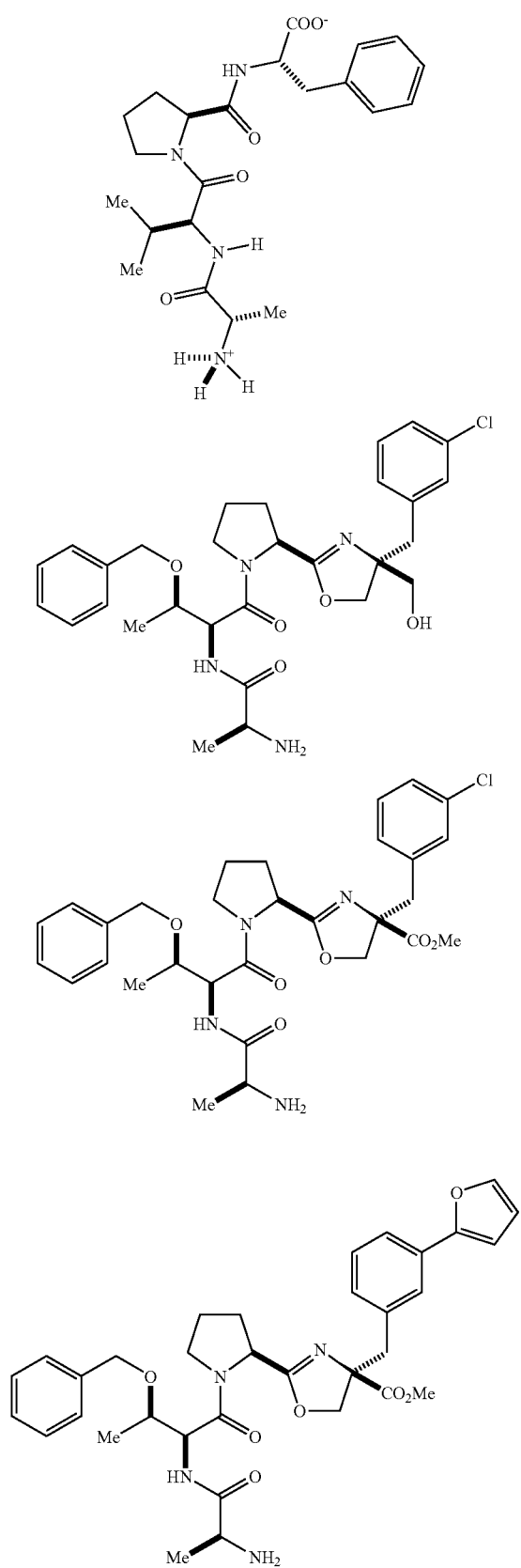
98
-continued
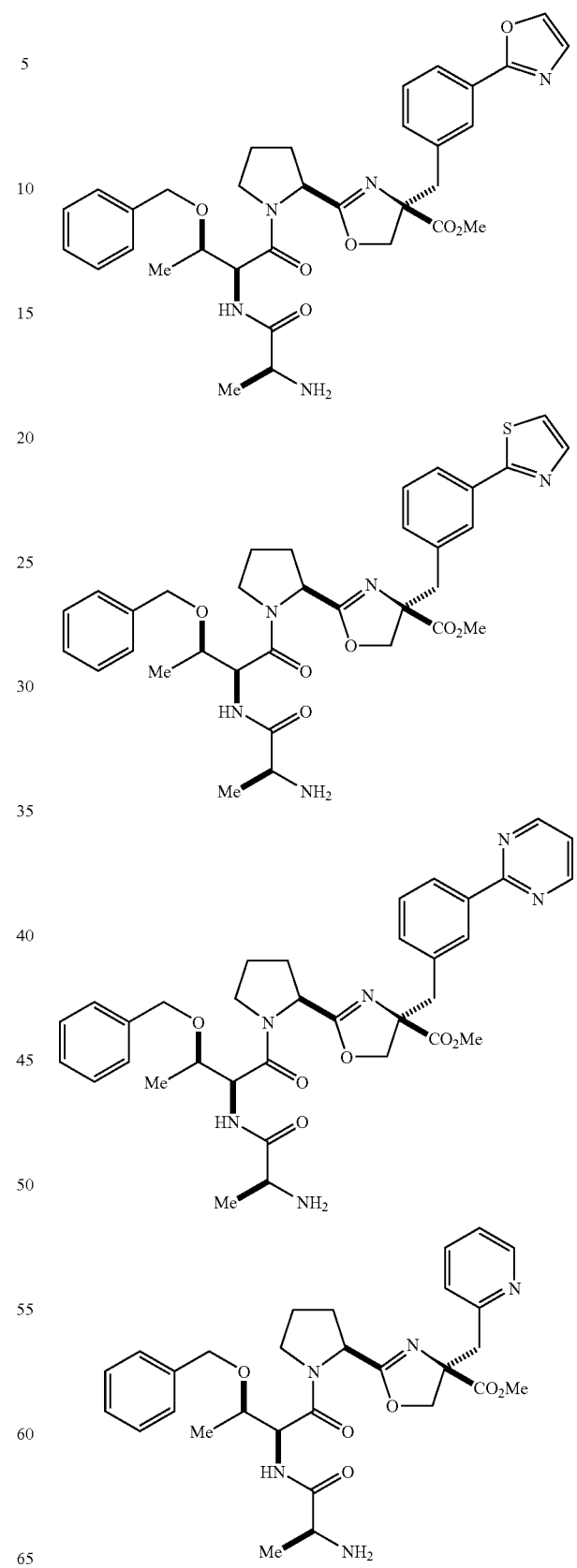

-continued
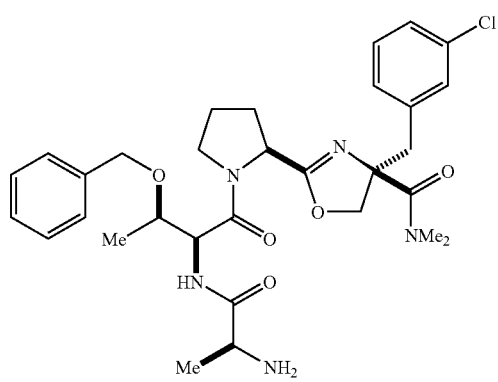
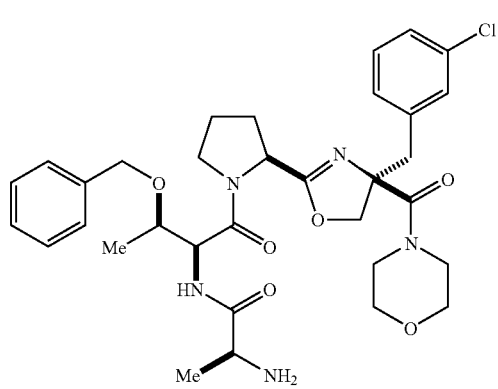
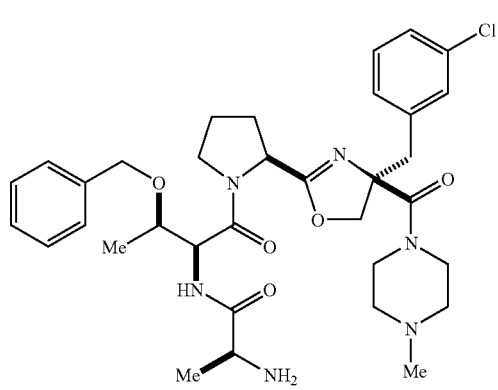
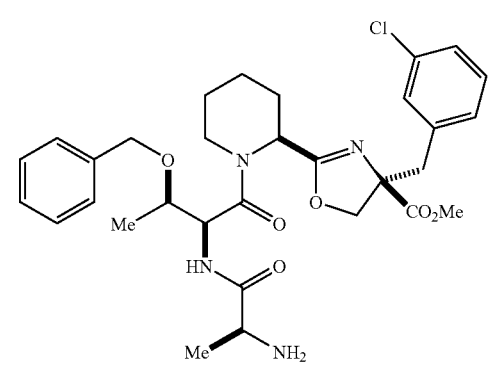
-continued
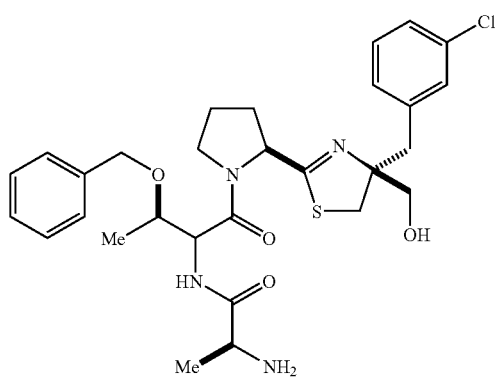
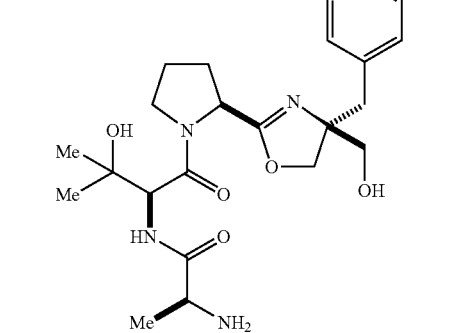
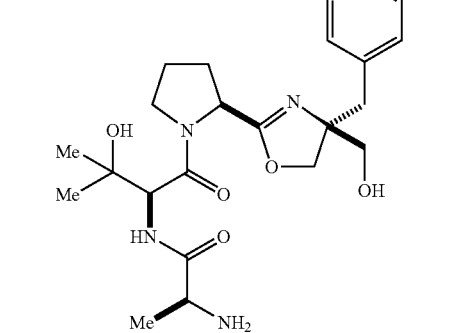
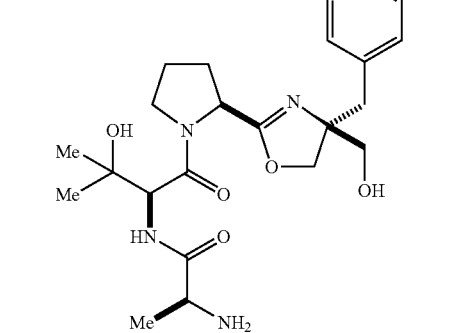
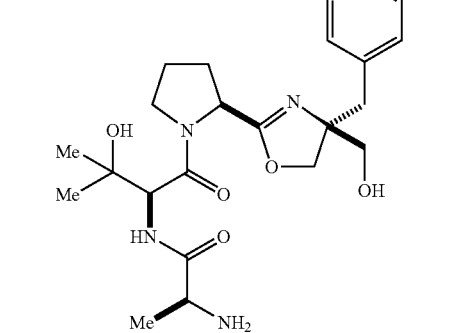

-continued
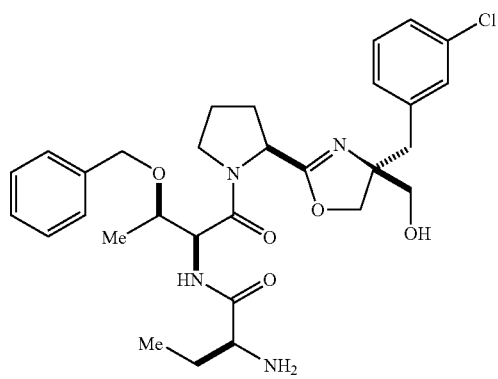
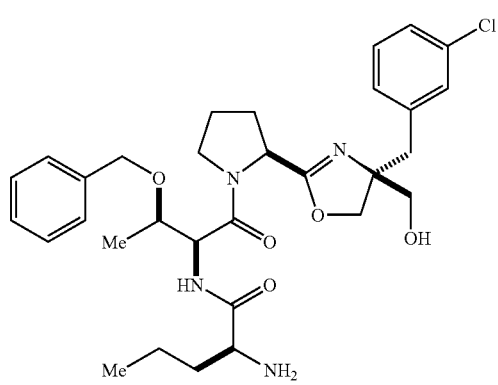
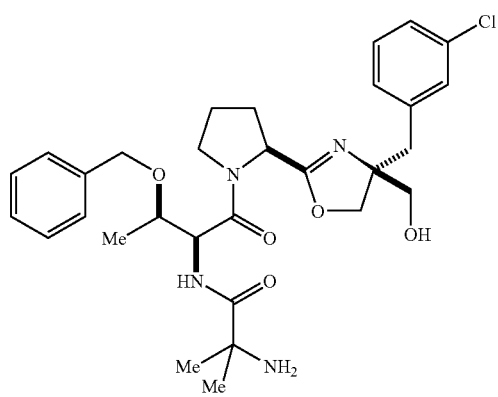
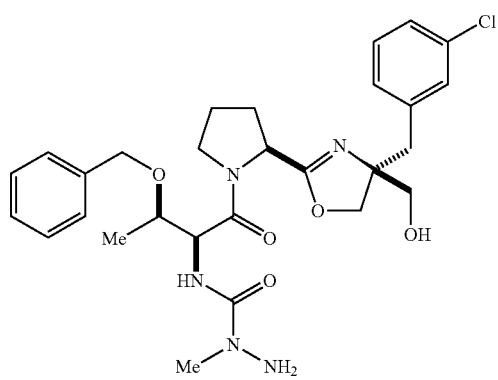
-continued
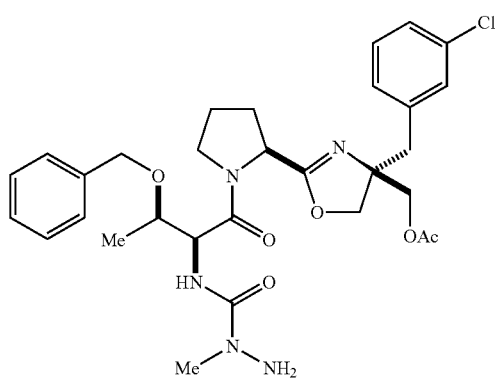
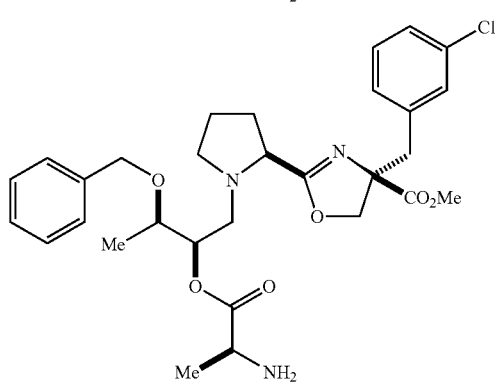
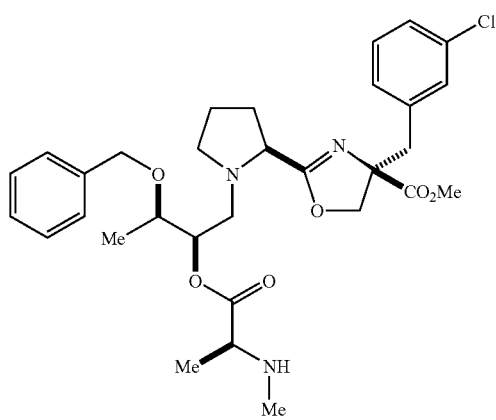
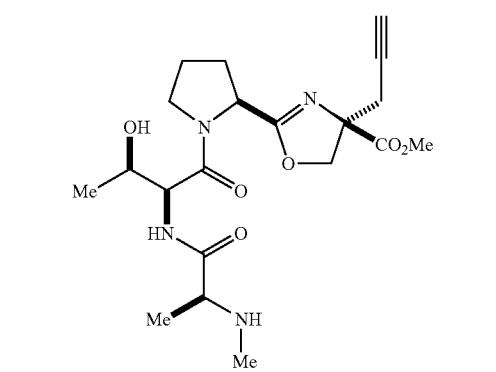

103
-continued
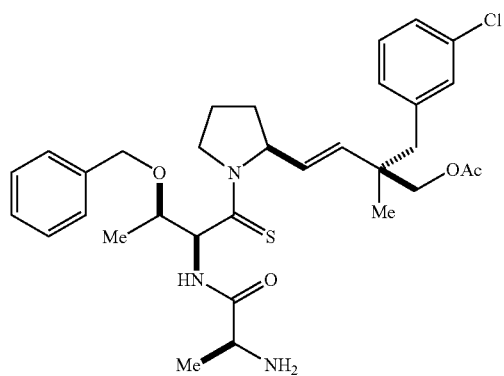
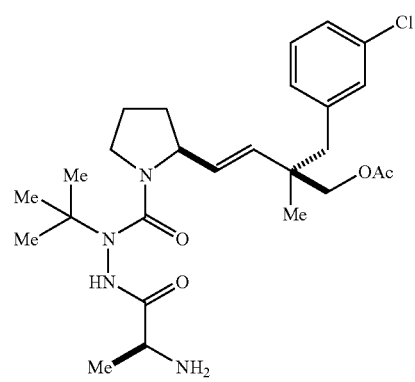
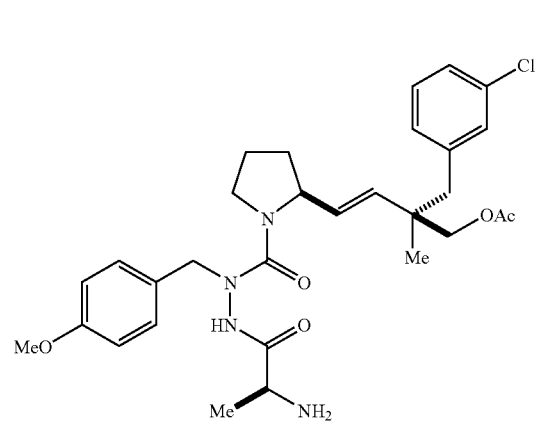
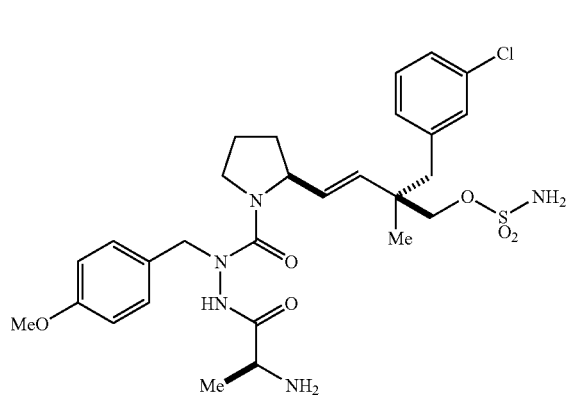
104
-continued
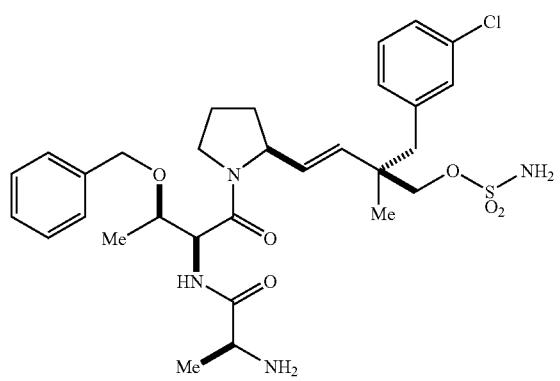
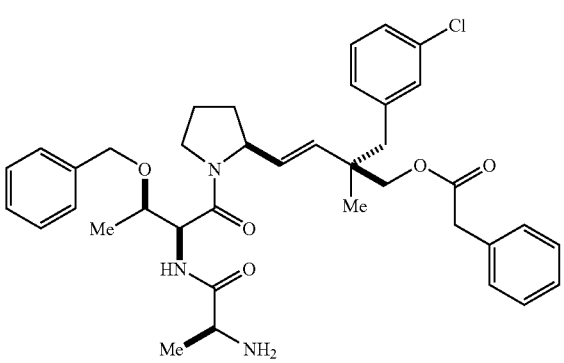
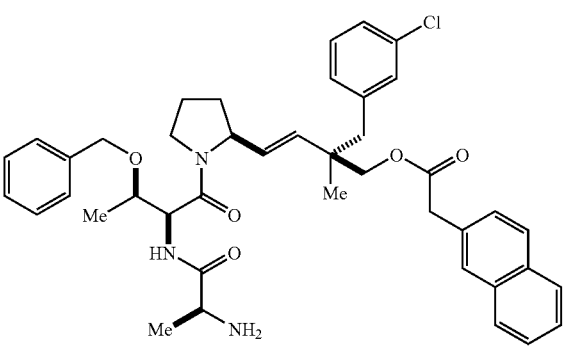
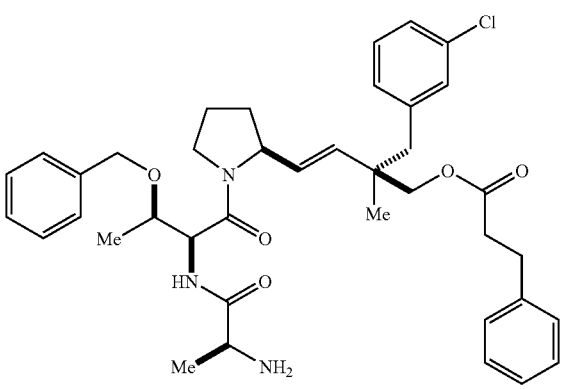

105
-continued
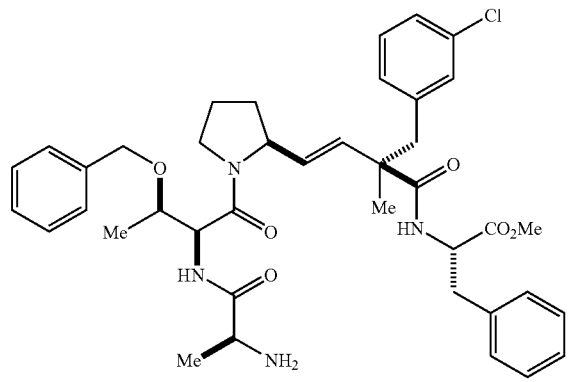
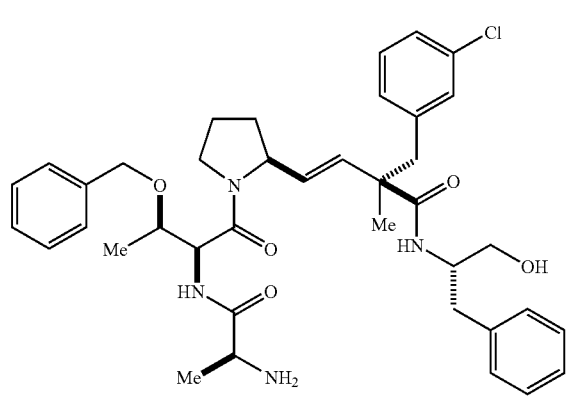
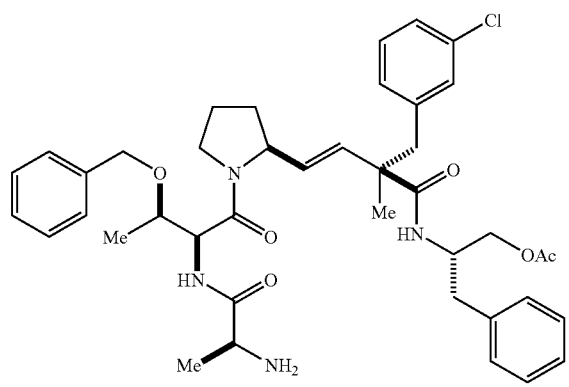
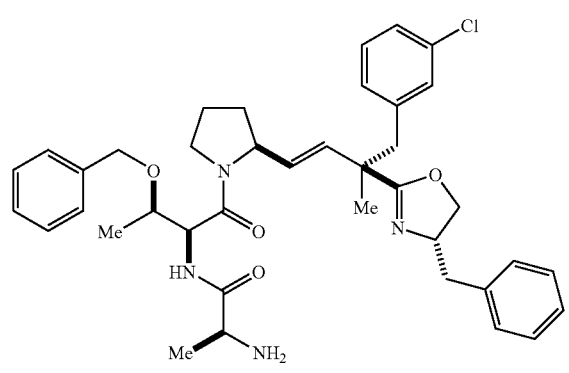
106
-continued
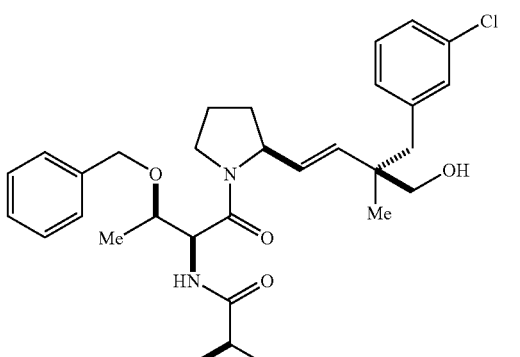
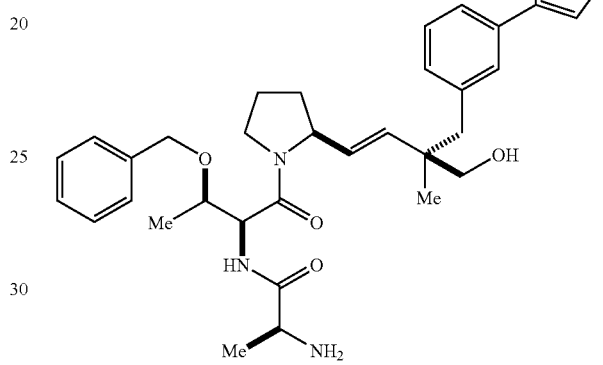
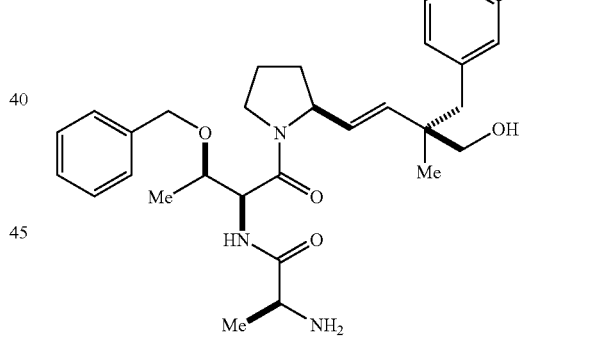
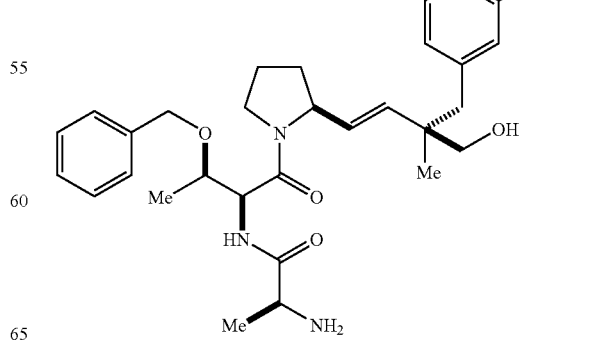

107
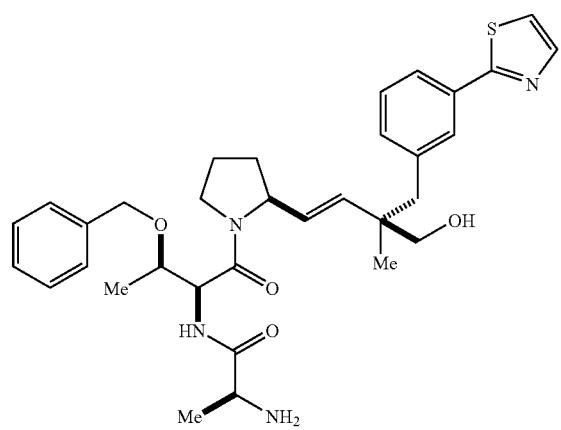
108
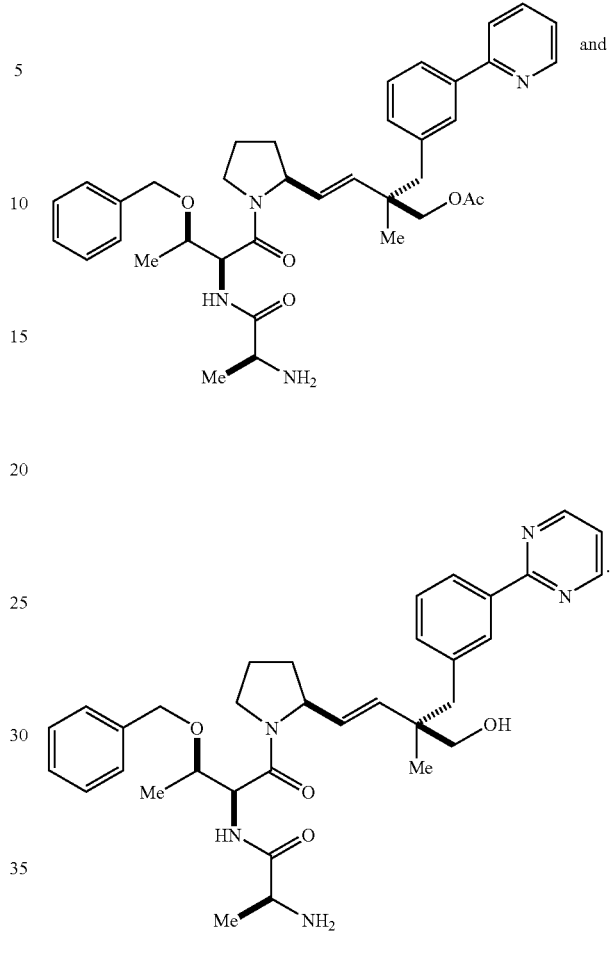
24. The compound of claim 1, wherein R1 and R2, and R1' and R2' are connected in 4-membered rings.
25. The compound of claim 1 of the structure:
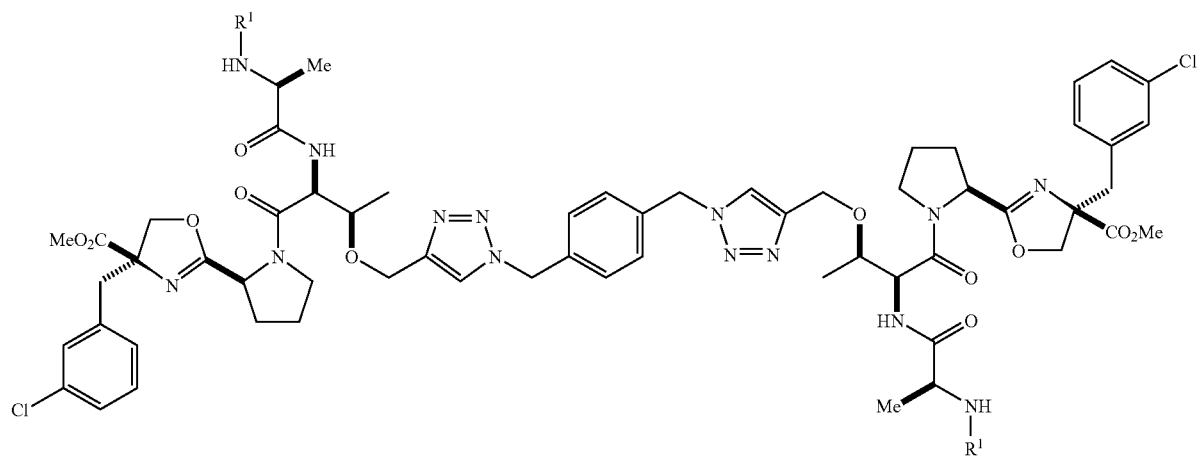
wherein R1 is H or Me.

26. The compound of claim 1 of the structure:

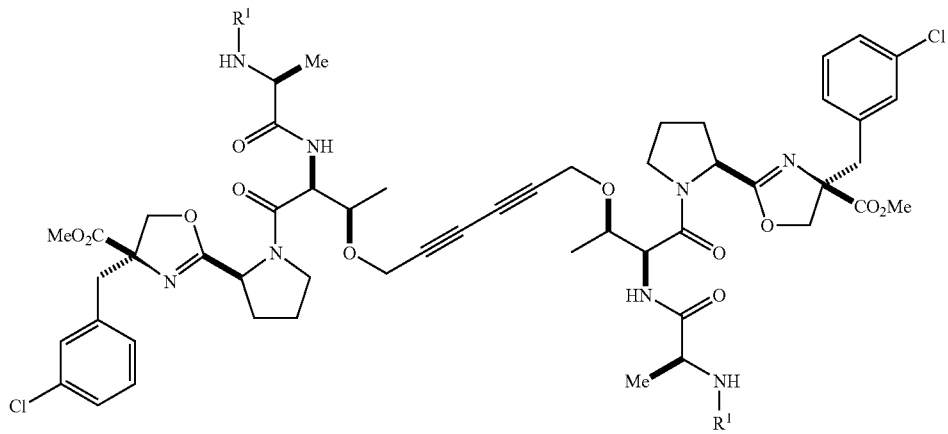

wherein R1 is H or Me.

27. The compound of claim 1 of the structure:

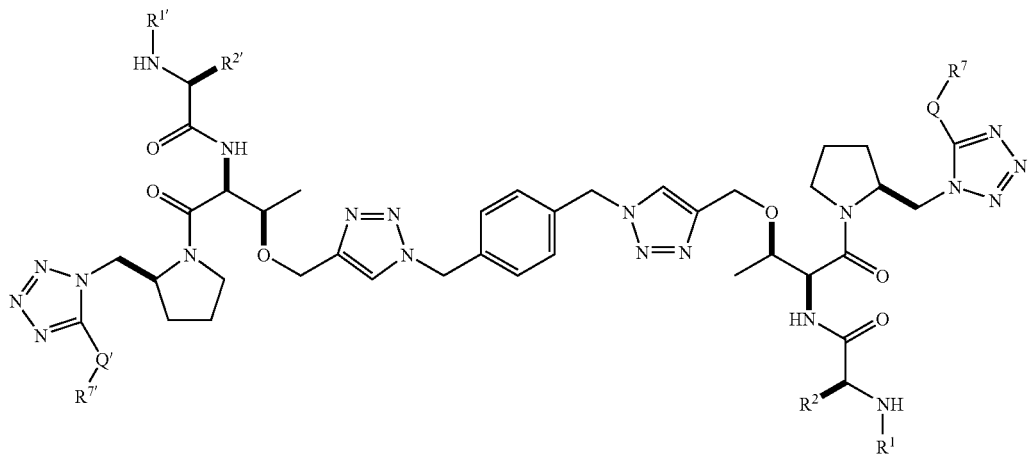

wherein:
R1 and R1' are independently selected from H and Me;
R2 and R2' are independently selected from Me and Et;
R7 and R7' are independently selected from aryl, heteroaryl, CH$_2$aryl, CH$_2$heteroaryl, branched alkyl, cycloalkyl, and functionalized alkyl or cycloalkyl; and
Q and Q' are independently selected from O, S, and NR1.

28. The compound of claim 1 of the structure

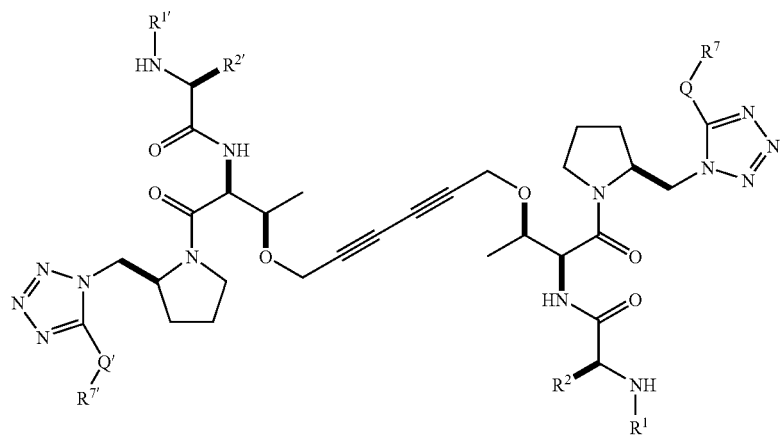

R1 and R1' are independently selected from H and Me;
R2 and R2' are independently selected from Me and Et;
R7 and R7' are independently selected from aryl, heteroaryl, CH$_2$aryl, CH$_2$heteroaryl, branched alkyl, cycloalkyl, and functionalized alkyl or cycloalkyl; and
Q and Q' are independently selected from O, S, and NR1.

29. The compound of claim 1, of the structure:

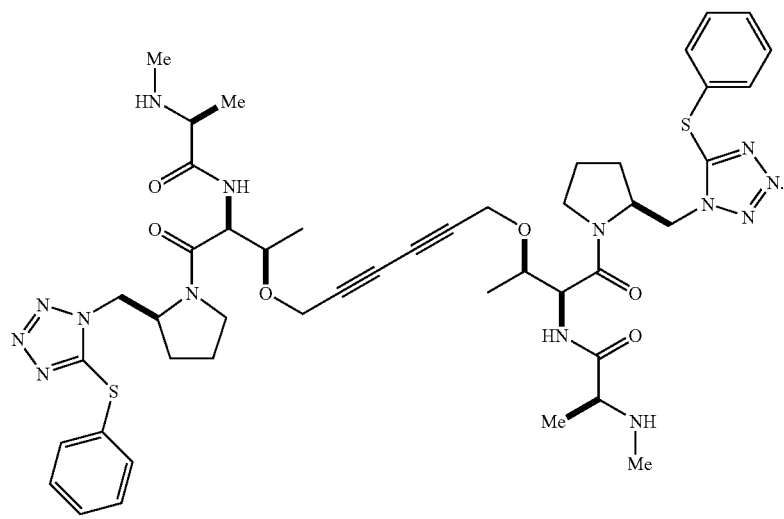

30. The compound of claim 1, of the structure:

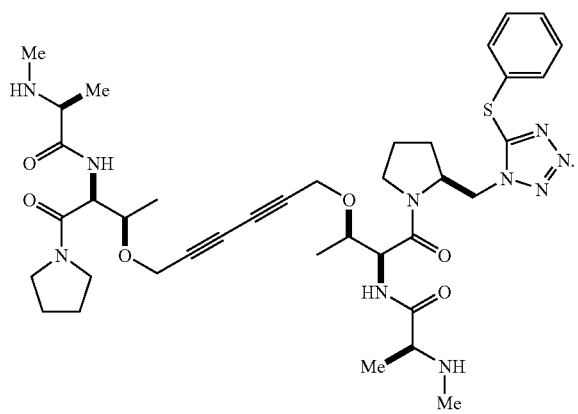

31. The compound of claim 1, of the structure:

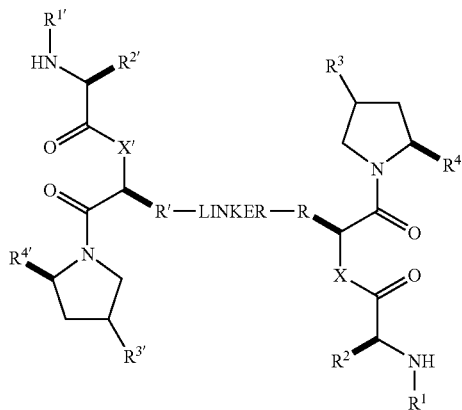

wherein:

R4' is selected from:

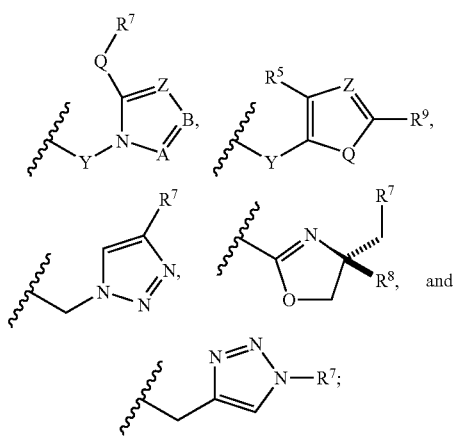

R and R' are independently selected from CH₂, CHMe, CHEt, CMe₂, and 1,1-disubstituted cyclopropyl;

R1 and R1' are independently selected from H and Me;

R2 and R2' are independently selected from Me and Et;

R3 and R3' are independently selected from H, Me, halogen, straight chain or branched alkyl, cycloalkyl, aryl, heteroaryl, functionalized alkyl or cycloalkyl, OR5, and NR5R6;

R4 is selected from R5 and R4';

R5 and R6 are independently selected from H, Me, straight chain alkyl, and any of R7;

R7 is selected from aryl, heteroaryl, branched alkyl, cycloalkyl, and functionalized alkyl or cycloalkyl;

R8 is selected from CH₂OR5, CH₂OC(O)R5, CH₂OC(O)NHR5, CO₂R5, and C(O)NR5R6;

R9 is selected from H, OR5, and NR5R6;

A, B, and Z are independently selected from CH, N, and C—R7;

Q is selected from CH₂, CHMe, 0, S, and NRS;

X and X' are independently selected from NH, O, and CH₂;

Y is selected from CH₂, C(O), C(S), and CHMe;

LINKER is a contiguous chain of between 2 and 200 atoms, having a MW between 20 and 2 KD that can incorporate substitution, heteroatoms, unsaturation and cyclic aromatic and heteroaromatic portions;

or a pharmaceutically-acceptable salt thereof.

32. The compound of claim 31 wherein LINKER is selected from:

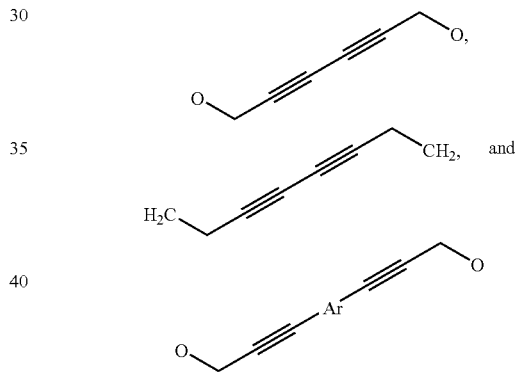

wherein Ar is a 1, 3 or 1,4-linked aromatic or heteroaromatic ring.

33. The compound of claim 31 wherein LINKER is O(CH2)nO wherein n is 5-10.

34. The compound of claim 31 wherein LINKER is (CH2)n wherein n is 6-12.

35. The compound of claim 31 wherein LINKER is unsymmetrical and selected from:

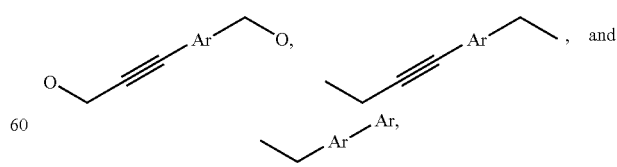

wherein Ar is a 1, 3 or 1,4-linked aromatic or heteroaromatic ring.

36. The compound of claim 31 wherein LINKER is truncated and selected from:

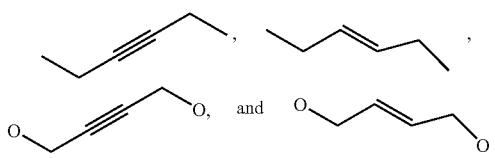

37. The compound of claim 1, of the structure:

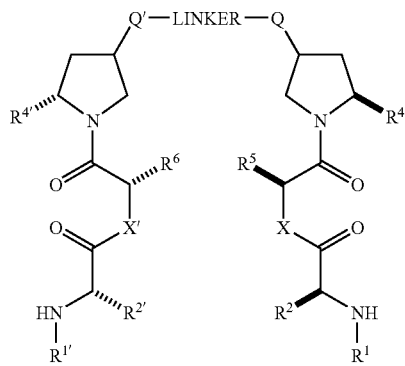

wherein:
R4' is selected from:

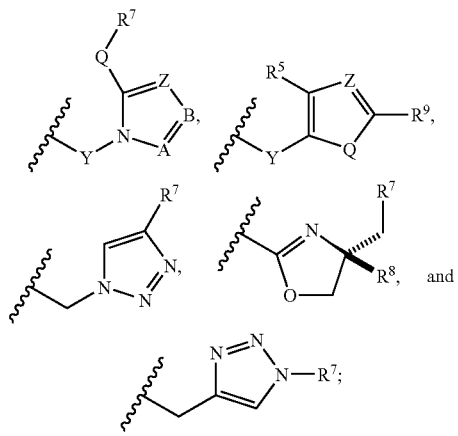

R1 and R1' are independently selected from H and Me;
R2 and R2' are independently selected from Me and Et;
R4 is selected from R5 and R4'
R5 and R6 are independently selected from H, Me, straight chain alkyl, or any of R7;
R7 is selected from aryl, heteroaryl, branched alkyl, cycloalkyl, and functionalized alkyl or cycloalkyl;
R8 is selected from $CH_2OR5$, $CH_2OC(O)R5$, $CH_2OC(O)NHR5$, $CO_2R5$, and $C(O)NR5R6$;
R9 is selected from H, OR5, and NR5R6;
A, B, and Z are independently selected from CH, N, and C—R7;
Q and Q' are independently selected from $CH_2$, CHMe, O, S, and NR5;
X and X' are independently selected from NH, O, and $CH_2$;
Y is selected from $CH_2$, C(O), C(S), and CHMe; and
LINKER is a contiguous chain of between 2 and 200 atoms, having a MW between 20 and 2 KD that can incorporate substitution, heteroatoms, unsaturation and cyclic aromatic and heteroaromatic portions;
or a pharmaceutically-acceptable salt thereof.

38. The compound of claim 37 wherein LINKER is selected from:

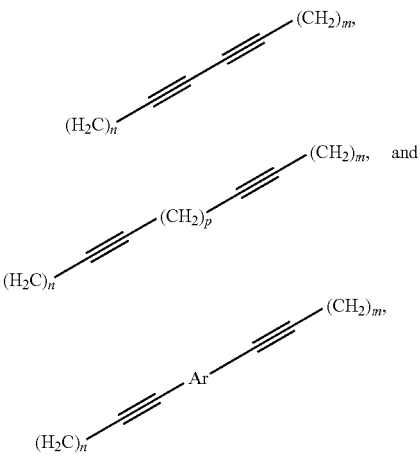

wherein:
n and m are independently 1-6,
p is 0-6, and
Ar is a 1,3 or 1,4-linked aromatic or heteroaromatic ring.

39. The compound of claim 37 wherein LINKER is $(CH_2)_n$ wherein n is 6-12.

40. The compound of claim 1, of the structure:

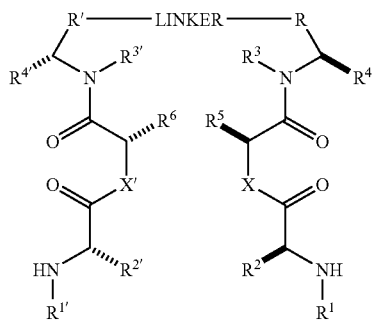

wherein:
R4' is selected from:

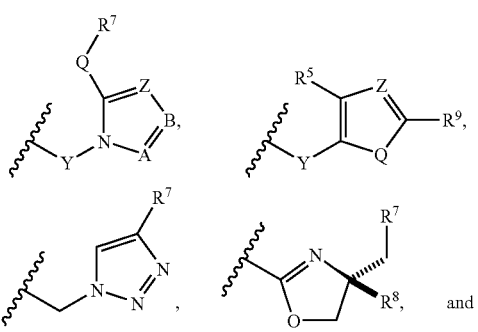

-continued

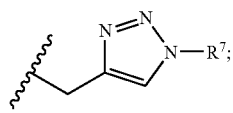

R and R' are independently selected from CH$_2$, CHMe, CHEt, CMe$_2$, and 1,1-disubstituted cyclopropyl;

R1 and R1' are independently selected from H and Me;

R2 and R2' are independently selected from Me and Et;

R3 and R3' are independently selected from H, Me, straight chain or branched alkyl, cycloalkyl, and functionalized alkyl or cycloalkyl;

R4 is selected from R5 and R4';

R5 and R6 are independently selected from H, Me, straight chain alkyl, and any of R7;

R7 is selected from aryl, heteroaryl, branched alkyl, cycloalkyl, and functionalized alkyl or cycloalkyl;

R8 is selected from CH$_2$OR5, CH$_2$OC(O)R5, CH$_2$OC(O)NHR5, CO$_2$R5, and C(O)NR5R6;

R9 is selected from H, OR5, and NR5R6;

A, B, and Z are independently selected from CH, N, and C—R7;

Q is selected from CH$_2$, CHMe, 0, S, and NR5;

X and X' are independently selected from NH, O, and CH$_2$;

Y is selected from CH$_2$, C(O), C(S), CHMe; and

LINKER is a contiguous chain of between 2 and 200 atoms, having a MW between 20 and 2 KD that can incorporate substitution, heteroatoms, unsaturation and cyclic aromatic and heteroaromatic portions;

or a pharmaceutically-acceptable salt thereof.

41. The compound of claim 40 wherein LINKER is selected from:

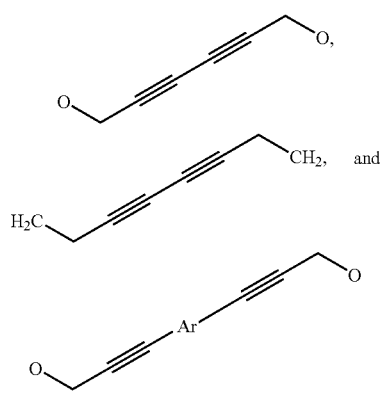

wherein Ar is a 1,3 or 1,4-linked aromatic or heteroaromatic ring.

42. The compound of claim 40 wherein LINKER is O(CH$_2$)$_n$O wherein n is 5-10.

43. The compound of claim 40 wherein LINKER is (CH$_2$)$_n$ wherein n is 6-12.

44. The compound of claim 1, of the structure:

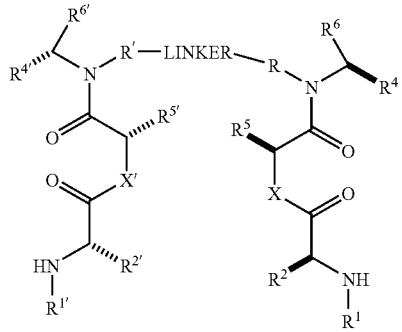

wherein:

R4' is selected from:

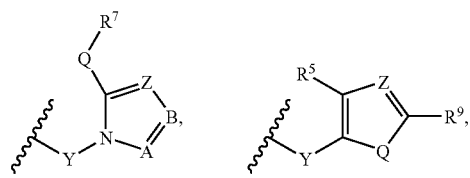

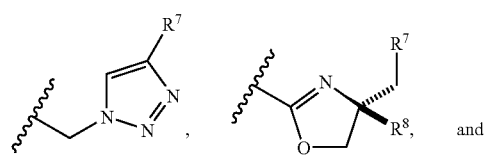

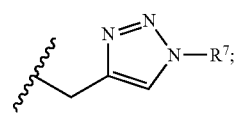

R and R' are independently selected from CH$_2$ and C(O);

R1 and R1' are independently selected from H and Me;

R2 and R2' are independently selected from Me and Et;

R4 is selected from R5 and R4';

R5, R5', R6, R6' are independently selected from H, Me, straight chain alkyl, and any of R7;

R7 is selected from aryl, heteroaryl, branched alkyl, cycloalkyl, and functionalized alkyl or cycloalkyl;

R8 is selected from CH$_2$OR5, CH$_2$OC(O)R5, CH$_2$OC(O)NHR5, CO$_2$R5, and C(O)NR5R6;

R9 is selected from H, OR5, and NR5R6;

A, B, and Z are independently selected from CH, N, and C—R7;

Q is selected from CH₂, CHMe, O, S, and NR5;

X and X' are independently selected from NH, O, and CH₂;

Y is selected from CH₂, C(O), C(S), and CHMe; and

LINKER is a contiguous chain of between 2 and 200 atoms, having a MW between 20 and 2 KD that can incorporate substitution, heteroatoms, unsaturation and cyclic aromatic and heteroaromatic portions;

or a pharmaceutically-acceptable salt thereof.

45. The compound of claim 1, of the structure:

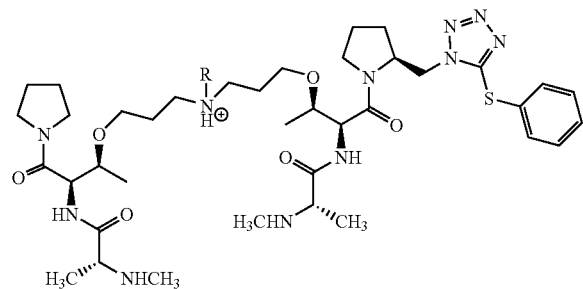

wherein R is selected from H, alkyl and branched alkyl.

46. The compound of claim 1, of the structure:

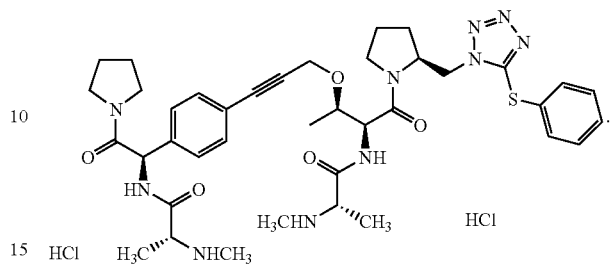

47. The compound of claim 1, of the structure:

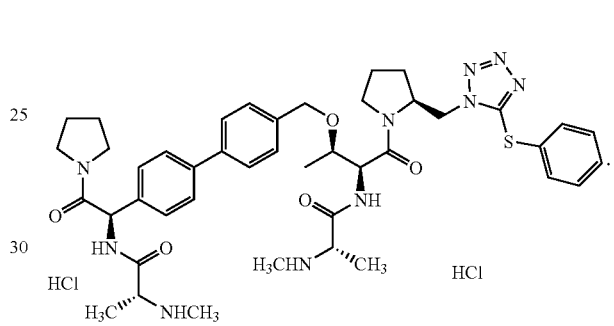

48. The compound of claim 1, of the structure:

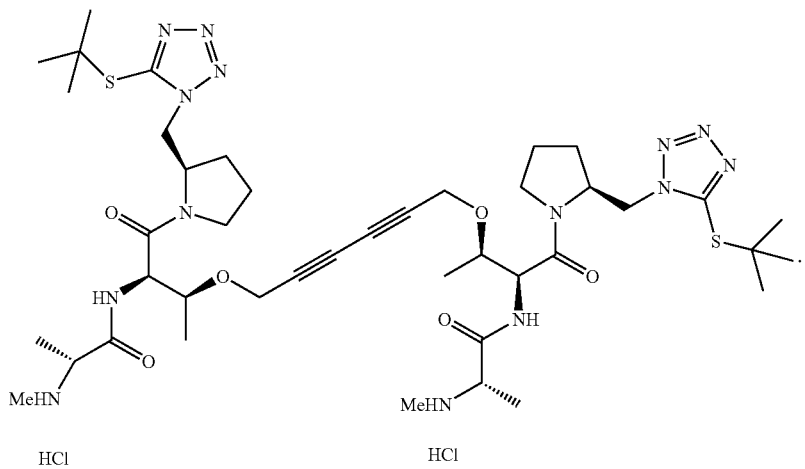

49. The compound of claim 1, of the structure:

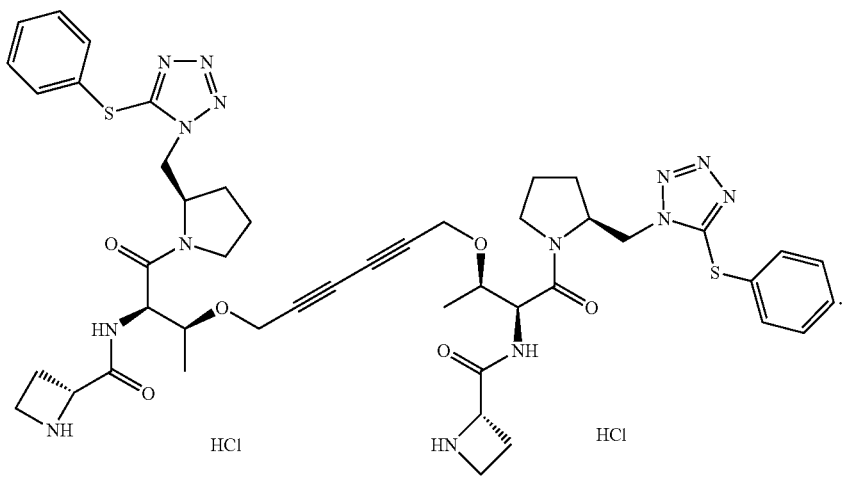

50. The compound of claim 1, wherein:
R1 and R1' are selected from hydrogen and methyl;
R2 and R2' are selected from methyl and ethyl;
R3 and R3' are NH;
R4 and R4' are CH;
R6/R6' and R7/R7', or R7/R7' and R8/R8' are connected in a 5- to 8-membered ring; and
L covalently links R5, R6 or R7, with R5', R6' or R7'.

51. The compound of claim 1, wherein:
R1 and R1' are selected from hydrogen and methyl;
R2 and R2' are selected from methyl and ethyl;
R3 and R3' are NH;
R4 and R4' are CH;
R5 and R5' are C1-C3 alkyl;
R6/R6' and R7/R7', or R7/R7' and R8/R8' are connected in a 5- to 8-membered ring; and
L covalently links R5, R6 or R7, with R5', R6' or R7'.

52. The compound of claim 1, wherein:
R1 and R1' are methyl;
R2 and R2' are methyl;
R3 and R3' are NH;
R4 and R4' are CH;
R5 and R5' are alkyl;
R6 and R6' are ethyl;
R7 and R7' are methyl;
R8 and R8' are substituted alkyl;
R6 and R7, and R6' and R7', are connected in 5-membered (pyrrolidinyl) rings; and
L covalently links R5 with R5', or R6 with R6'.

53. The compound of claim 1, wherein:
R1 and R1' are methyl;
R2 and R2' are methyl;
R3 and R3' are NH;
R4 and R4' are CH;
R5 and R5' are methyl, ethyl, n-propyl, isopropyl, n-butyl, t-butyl, isobutyl, sec-butyl, cyclohexyl, (cyclohexyl)methyl, cyclopropylmethyl, or a homolog or isomer of n-pentyl, n-hexyl, n-heptyl, or n-octyl;
R6 and R6' are ethyl;
R7 and R7' are methyl;
R8 and R8' are substituted alkyl;
R6 and R7, and R6' and R7', are connected in 5-membered (pyrrolidinyl) rings; and
L covalently links R5 with R5', or R6 with R6'.

54. The compound of claim 1, wherein:
R1 and R1' are methyl;
R2 and R2' are methyl;
R3 and R3' are NH;
R4 and R4' are CH;
R5 and R5' are t-butyl or ethyl;
R6 and R6' are ethyl;
R7 and R7' are methyl;
R8 and R8' are substituted alkyl comprising an =O substituent;
R6 and R7, and R6' and R7', are connected in 5-membered (pyrrolidinyl) rings; and
L covalently links R5 with R5', or R6 with R6'.

55. The compound of claim 1, wherein:
R1 and R1' are methyl;
R2 and R2' are methyl;
R3 and R3' are NH;
R4 and R4' are CH;
R5 and R5' are t-butyl or ethyl;
R6 and R6' are ethyl;
R7 and R7' are methyl;
R8 and R8' are substituted alkyl comprising an =O substituent and an —NR'R" substituent, wherein R' is H and R" is selected from hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups;
R6 and R7, and R6' and R7', are connected in 5-membered (pyrrolidinyl) rings; and
L covalently links R5 with R5', or R6 with R6'.

56. The compound of claim 1, wherein:
R1 and R1' are methyl;
R2 and R2' are methyl;
R3 and R3' are NH;
R4 and R4' are CH;
R5 and R5' are t-butyl;
R6 and R6' are ethyl;
R7 and R7' are methyl;

R8 and R8' are substituted alkyl comprising an =O substituent and an —NR'R" substituent, wherein R' is H and R" is selected from hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups;

R6 and R7, and R6' and R7', are connected in 5-membered (pyrrolidinyl) rings; and L covalently links R6 with R6'.

57. The compound of claim 1, wherein:
R1 and R1' are methyl;
R2 and R2' are methyl;
R3 and R3' are NH;
R4 and R4' are CH;
R5 and R5' are ethyl;
R6 and R6' are ethyl;
R7 and R7' are methyl;
R8 and R8' are substituted alkyl comprising an =O substituent and an —NR'R" substituent, wherein R' is H and R" is selected from hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups;
R6 and R7, and R6' and R7', are connected in 5-membered (pyrrolidinyl) rings; and
L covalently links R5 with R5".

58. A method of promoting apoptosis of pathogenic mammalian cells, the method comprising the steps of contacting the cells with an effective amount of the compound of claim 1, and detecting a resultant increase in apoptosis of the cells.

59. The method of claim 58, wherein the cells are cancer cells.

60. The method of claim 58, wherein the cells are in vitro.

61. The method of claim 58, wherein the cells are cancer cells in vitro.

62. The compound of claim 1 wherein L is a contiguous chain of between 2 and 200 atoms, having a MW between 20 D and 2 KD that can incorporate substitution, heteroatoms, unsaturation and cyclic aromatic and heteroaromatic portions.

63. The compound of claim 1 wherein L is selected from:

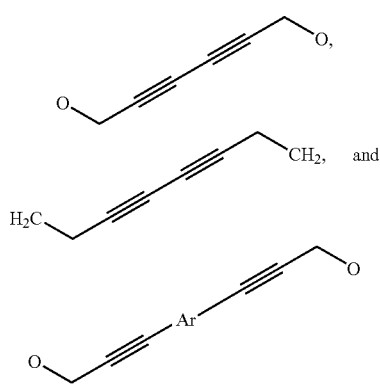

wherein Ar is a 1, 3 or 1,4-linked aromatic or heteroaromatic ring.

64. The compound of claim 1 wherein L is:

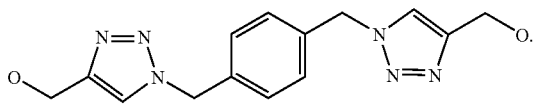

65. A pro-apoptotic Smac (second mitochondria-derived activator of caspases) peptide mimetic dimeric compound of the general formula M1-L-M2, wherein moieties M1 and M2 are monomeric Smac mimetics and L is a linker covalently linking M1 and M2 in the active dimeric compound, wherein M1-L-M2 is of formula II, formula II

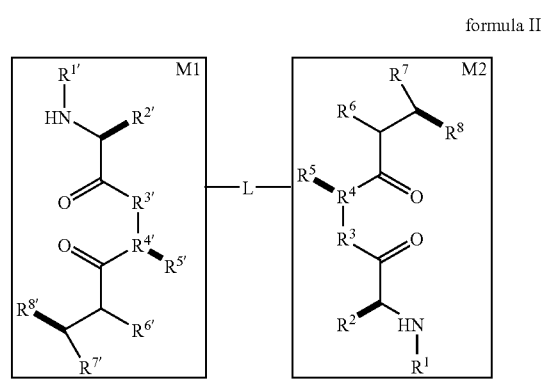

wherein:
R1 and R1' are selected from hydrogen, optionally substituted methyl, and hydroxyl;
R2 and R2' are selected from optionally substituted methyl and optionally substituted ethyl;
R3 and R3' are selected from CH2, NH, O and S;
R4 and R4' are selected from CH and N;
R5-R8, and R5'—R8' are selected from hydrogen, optionally hetero-, optionally substituted alkyl, optionally hetero-, optionally substituted alkenyl, optionally hetero-, optionally substituted alkynyl, optionally hetero-, optionally substituted aryl, wherein optionally either R6 and R7 as well as R6' and R7' or R7 and R8 as well as R7' and R8' are connected in 5- to 8-membered rings; and
L is a contiguous chain of between 2 and 200 atoms, having a MW between 20 D and 2 KD that can incorporate substitution, heteroatoms, unsaturation and cyclic aromatic and heteroaromatic portions, covalently linking R2, R5, R6 or R7, with R2', R5', R6' or R7', respectively, or a pharmaceutically-acceptable salt thereof.

66. The compound of claim 65, wherein R1 and R1' are selected from hydrogen and methyl.

67. The compound of claim 65, wherein R2 and R2' are selected from methyl and ethyl.

68. The compound of claim 65, wherein R3 and R3' are NH.

69. The compound of claim 65, wherein R4 and R4' are CH.

70. The compound of claim 65, wherein R5 and R5' are C1-C3 alkyl.

71. The compound of claim 65, wherein R1 and R1' are selected from hydrogen and methyl, R2 and R2' are selected from methyl and ethyl, R3 and R3' are NH, R4 is CH, and R5 and R5' are C1-C3 alkyl, and L covalently links R5, R6 or R7, with R5', R6' or R7'.

72. The compound of claim 65, wherein either R6 and R7 as well as R6' and R7' or R7 and R8 as well as R7' and R8' are connected in 5- to 8-membered rings.

73. The compound of claim 65, wherein R7 and R8 are connected in a 5- or 6-membered ring.

74. The compound of claim 65, wherein R6 and R7 are connected in a 5- or 6-membered ring.

75. The compound of claim 65, wherein R6 and R7 are connected in a 5-membered ring, and L covalently links the ring with R2', R5', R6' or R7'.

76. The compound of claim 65, wherein R8 comprises a 5- or 6-membered ring.

77. The compound of claim 65, wherein R8 comprises a 5-membered ring, comprising at least one heteroatom, at least one substitution, and at least one unsaturation.

78. The compound of claim 65, wherein R1 and R2, and R1' and R2' are connected in 5-membered rings.

79. The compound of claim 65, wherein L is a contiguous chain of between 4 and 100 atoms, and between 40 D and 1 kD.

80. The compound of claim 65, wherein L is an optionally hetero-, optionally substituted dialkynyl radical.

81. The compound of claim 65, wherein L is substituted with a protonated or alkylated amine wherein the compound is a triamine.

82. The compound of claim 65, wherein the dimer is symmetrical about the linker.

83. The compound of claim 65, wherein the dimer is symmetrical.

84. A pharmaceutical composition comprising the compound of claim 65 and a pharmaceutically acceptable excipient.

85. A pharmaceutical composition comprising the compound of claim 65 and a pharmaceutically acceptable excipient, copackaged with instructions describing use of the composition to treat a disease associated with undesirable caspase activity.

86. The pharmaceutical composition of claim 65 comprising a unit dosage of the compound.

87. A method of promoting apoptosis of pathogenic mammalian cells, the method comprising the steps of contacting the cells with an effective amount of the compound of claim 65, and detecting a resultant increase in apoptosis of the cells.

88. The compound of claim 65, wherein:
R1 and R1' are selected from hydrogen and methyl;
R2 and R2' are selected from methyl and ethyl;
R3 and R3' are NH;
R4 and R4' are CH;
R6/R6' and R7/R7', or R7/R7' and R8/R8' are connected in a 5- to 8-membered ring; and
L covalently links R5, R6 or R7, with R5', R6' or R7', respectively.

89. The compound of claim 65, wherein:
R1 and R1' are selected from hydrogen and methyl;
R2 and R2' are selected from methyl and ethyl;
R3 and R3' are NH;
R4 and R4' are CH;
R5 and R5' are optionally substituted alkyl;
R6/R6' and R7/R7', or R7/R7' and R8/R8' are connected in a 5- to 8-membered ring; and
L covalently links R5, R6 or R7, with R5', R6' or R7', respectively.

90. The compound of claim 65, wherein:
R1 and R1' are selected from hydrogen and methyl;
R2 and R2' are selected from methyl and ethyl;
R3 and R3' are NH;
R4 and R4' are CH;
R5 and R5' are alkyl;
R6/R6' and R7/R7', or R7/R7' and R8/R8' are connected in a 5- to 8-membered ring; and
L covalently links R5, R6 or R7, with R5', R6' or R7', respectively.

91. The compound of claim 65, wherein:
R1 and R1' are selected from hydrogen and methyl;
R2 and R2' are selected from methyl and ethyl;
R3 and R3' are NH;
R4 and R4' are CH;
R5 and R5' are methyl, ethyl, propyl or butyl;
R6/R6' and R7/R7', or R7/R7' and R8/R8' are connected in a 5- to 8-membered ring; and
L covalently links R5, R6 or R7, with R5', R6' or R7', respectively.

92. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are substituted alkyl;
R7 and R7' are methyl;
R8 and R8' are H; and
R6/R6' and R7/R7' are connected in a 5- to 8-membered ring; and
L covalently links R5, R6 or R7, with R5', R6' or R7', respectively.

93. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are substituted ethyl;
R7 and R7' are methyl;
R8 and R8' are H
R6 and R7, and R6' and R7', are connected in 5-membered pyrrolidinyl rings; and
L covalently links R5, R6 or R7, with R5', R6' or R7', respectively.

94. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl substituted with CONR'R" wherein R' and R" are independently selected from hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups;
R7 and R7' are methyl;
R8 and R8' H;
R6 and R7, and R6' and R7', are connected in 5-membered pyrrolidinyl rings; and
L covalently links R6 or R7 with R6' or R7', respectively.

95. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl substituted with CONR'R" wherein R' is H and R" is selected from hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups;
R7 and R7' are methyl;
R8 and R8' H;
R6 and R7, and R6' and R7', are connected in 5-membered pyrrolidinyl rings; and
L covalently links R6 or R7 with R6' or R7', respectively.

96. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is unsubstituted aryl;
R7 and R7' are methyl;
R8 and R8' H;
R6 and R7, and R6' and R7', are connected in 5-membered pyrrolidinyl rings; and
L covalently links R6 or R7 with R6' or R7', respectively.

97. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is an aryl selected from: phenyl, 1-naphthyl, 2-naphthyl, 4-biphenyl and 1,2,3,4-tetrahydronaphthyl;
R7 and R7' are methyl;
R8 and R8' H;
R6 and R7, and R6' and R7', are connected in 5-membered pyrrolidinyl rings; and
L covalently links R6 or R7 with R6' or R7', respectively.

98. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is 1,2,3,4-tetrahydronaphthyl;
R7 and R7' are methyl;
R8 and R8' H;
R6 and R7, and R6' and R7', are connected in 5-membered pyrrolidinyl rings; and
L covalently links R7 with R7'.

99. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is 1,2,3,4-tetrahydronaphthyl;
R7 and R7' are methyl;
R8 and R8' H;
R6 and R7, and R6' and R7', are connected in 5-membered pyrrolidinyl rings; and
L covalently links R7 with R7'.

100. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is 1,2,3,4-tetrahydronaphthyl;
R7 and R7' are methyl;
R8 and R8' H;
R6 and R7, and R6' and R7', are connected in 5-membered pyrrolidinyl rings; and
L covalently links R6 with R6'.

101. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is aryl-(C1-C4)alkyl;
R7 and R7' are methyl;
R8 and R8' H;
R6 and R7, and R6' and R7', are connected in 5-membered pyrrolidinyl rings; and
L covalently links R5, R6 or R7 with R5', R6' or R7', respectively.

102. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is an aryl-(C1-C4)alkyl selected from benzyl, phenylethyl and pyridylmethyl;
R7 and R7' are methyl;
R8 and R8' H;
R6 and R7, and R6' and R7', are connected in 5-membered pyrrolidinyl rings; and
L covalently links R7 with R7'.

103. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl substituted with CONR'R" wherein R' is H and R" is phenylethyl;
R7 and R7' are methyl;
R8 and R8' H;
R6 and R7, and R6' and R7', are connected in 5-membered pyrrolidinyl rings; and
L covalently links R7 with R7'.

104. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted alkyl comprising an =O substituent and an —NR'R" substituent, wherein R' and R" are independently selected from hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups;
R6 and R7, and R6' and R7', are connected in 5-membered pyrrolidinyl rings; and
L covalently links R6 or R7 with R6' or R7', respectively.

105. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted methyl comprising an =O substituent and an —NR'R" substituent, wherein R' is H, and R" is selected from hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups;
R6 and R7, and R6' and R7', are connected in 5-membered pyrrolidinyl rings; and
L covalently links R6 or R7 with R6' or R7', respectively.

106. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted methyl comprising an =O substituent and an —NR'R" substituent, wherein R' is H and R" is an unsubstituted aryl;
R6 and R7, and R6' and R7', are connected in 5-membered pyrrolidinyl rings; and
L covalently links R6 or R7 with R6' or R7', respectively.

107. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted alkyl comprising an =O substituent and an —NR'R" substituent, wherein R' is H and R" is an aryl selected from: phenyl, 1-naphthyl, 2-naphthyl, 4-biphenyl and 1,2,3,4-tetrahydronaphthyl;
R6 and R7, and R6' and R7', are connected in 5-membered pyrrolidinyl rings; and
L covalently links R6 or R7 with R6' or R7', respectively.

108. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted alkyl comprising an =O substituent and an —NR'R" substituent, wherein R' is H and R" is 1,2,3,4-tetrahydronaphthyl;
R6 and R7, and R6' and R7', are connected in 5-membered pyrrolidinyl rings; and
L covalently links R6 or R7 with R6' or R7', respectively.

109. The compound of claim 65, wherein:
R1 and R1' are methyl;
R2 and R2' are methyl;
R3 and R3' are NH;
R4 and R4' are CH;
R5 and R5' are t-butyl;
R6 and R6' are ethyl;
R7 and R7' are methyl;
R8 and R8' are substituted alkyl comprising an =O substituent and an —NR'R" substituent, wherein R' is H and R" is 1,2,3,4-tetrahydronaphthyl;
R6 and R7, and R6' and R7', are connected in 5-membered pyrrolidinyl rings; and
L covalently links R6 with R6'.

110. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted methyl comprising an =O substituent and an —NR'R" substituent, wherein R' is H and R" is aryl-(C1-C4)alkyl;
R6 and R7, and R6' and R7', are connected in 5-membered pyrrolidinyl rings; and
L covalently links R6 or R7 with R6' or R7', respectively.

111. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted alkyl comprising an =O substituent and an —NR'R" substituent, wherein R' is H and R" is an aryl-(C1-C4)alkyl selected from benzyl, phenylethyl and pyridylmethyl;
R6 and R7, and R6' and R7', are connected in 5-membered pyrrolidinyl rings; and
L covalently links R6 or R7 with R6' or R7', respectively.

112. The compound of claim 65, wherein:
R1 and R1' are methyl;
R2 and R2' are methyl;
R3 and R3' are NH;
R4 and R4' are CH;
R5 and R5' are methyl, ethyl, propyl or butyl;
R6 and R6' are ethyl;
R7 and R7' are methyl;
R8 and R8' are substituted alkyl comprising an =O substituent and an —NR'R" substituent, wherein R' is H and R" is phenylethyl;
R6 and R7, and R6' and R7', are connected in 5-membered pyrrolidinyl rings; and
L covalently links R6 with R6'.

\* \* \* \* \*